United States Patent
Yamamoto et al.

(10) Patent No.: US 11,851,681 B2
(45) Date of Patent: Dec. 26, 2023

(54) CELL PREPARATION METHOD

(71) Applicant: KYOTO PREFECTURAL PUBLIC UNIVERSITY CORPORATION, Kyoto (JP)

(72) Inventors: Kenta Yamamoto, Kyoto (JP); Tsunao Kishida, Kyoto (JP); Yoshihiro Sowa, Kyoto (JP); Toshiro Yamamoto, Kyoto (JP); Osam Mazda, Kyoto (JP)

(73) Assignee: KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 791 days.

(21) Appl. No.: 15/769,595

(22) PCT Filed: Oct. 20, 2016

(86) PCT No.: PCT/JP2016/081187
§ 371 (c)(1),
(2) Date: Sep. 17, 2018

(87) PCT Pub. No.: WO2017/069222
PCT Pub. Date: Apr. 27, 2017

(65) Prior Publication Data
US 2019/0024054 A1 Jan. 24, 2019

(30) Foreign Application Priority Data
Oct. 21, 2015 (JP) .................................. 2015-207529

(51) Int. Cl.
*C12N 5/077* (2010.01)
*C12N 5/0775* (2010.01)

(52) U.S. Cl.
CPC ......... *C12N 5/0656* (2013.01); *C12N 5/0653* (2013.01); *C12N 5/0654* (2013.01); *C12N 5/0655* (2013.01); *C12N 5/0658* (2013.01); *C12N 5/0663* (2013.01); *C12N 2501/15* (2013.01)

(58) Field of Classification Search
CPC .. C12N 5/0656; C12N 5/0653; C12N 5/0655; C12N 2501/115; C12N 5/0654; C12N 5/0658; C12N 5/0663; C12N 2501/15; C12N 2501/01; C12N 2501/11; C12N 2501/33; C12N 2501/39; C12N 2501/395; C12N 2501/415; C12N 2501/727; C12N 2506/1307; C12N 2506/1384; C12N 5/0662; C12N 5/0018; C12N 5/0622; C12N 5/0652; C12N 5/0684; C12N 2501/385
See application file for complete search history.

(56) References Cited

U.S. PATENT DOCUMENTS

| | | |
|---|---|---|
| 8,298,825 B1 | 10/2012 | Hochedlinger et al. |
| 8,603,818 B1 | 12/2013 | Hochedlinger et al. |
| 2009/0117439 A1 | 5/2009 | Fujinami et al. |
| 2010/0233804 A1 | 9/2010 | Zhou et al. |
| 2010/0267141 A1 | 10/2010 | Shi et al. |
| 2011/0110899 A1 | 5/2011 | Shi et al. |
| 2013/0273536 A1 | 10/2013 | Shi et al. |
| 2014/0120621 A1 | 5/2014 | Hochedlinger et al. |
| 2016/0186141 A1 | 6/2016 | Cao et al. |
| 2016/0369244 A1 | 12/2016 | Shi et al. |
| 2017/0081640 A1 | 3/2017 | Shi et al. |
| 2018/0002671 A1 | 1/2018 | Shi et al. |
| 2018/0171303 A1 | 6/2018 | Shi et al. |
| 2018/0216076 A1* | 8/2018 | Hebrok ................ C12N 5/0676 |

FOREIGN PATENT DOCUMENTS

| | | | |
|---|---|---|---|
| WO | 2009/117439 | 9/2009 | |
| WO | WO-2015011031 A1 * | 1/2015 | ............. A61P 21/00 |
| WO | 2015/038704 | 3/2015 | |

OTHER PUBLICATIONS

Zhu et al. Direct conversion of porcine embryonic fibroblasts into adipocytes by chemical molecules. Cellular Reprogramming 14.2 (2012): 99-105 (Year: 2012).*
Ifkovits et al. "Inhibition of TGFβ signaling increases direct conversion of fibroblasts to induced cardiomyocytes." PloS one 9.2 (2014): e89678 (Year: 2014).*
Massagué et al. "Controlling TGF-β signaling." Genes & development 14.6 (2000): 627-644 (Year: 2000).*
Supplementary European Search Report, dated Jul. 9, 2019 in corresponding European Patent Application No. EP 16 85 7535.
Yamamoto et al., "Direct conversion of human fibroblasts into functional osteoblasts by defined factors", PNAS, 112(19): pp. 6152-6157 (2015).
Petito et al., "Transforming Growth Factor-β1 May Be a Key Mediator of the Fibrogenic Properties of Neural Cells in Leprosy", J Neuropathol Exp Neurol, 72(4): pp. 351-365 (2013).
Li et al., "Small-Molecule-Driven Direct Reprogramrning of Mouse Fibroblasts into Functional Neurons", Cell Stem Cell, 17: pp. 195-203 (2015).
Valyasevi et al., "Stimulation of Adipogenesis, Peroxisome Proliferator-Activated Receptor-γ (PPARγ), and Thyrotropin Receptor by PPARγ Agonist in Human Orbital Preadipocyte Fibroblasts", Journal of Clinical Endocrinology & Metabolism, 2002, vol. 87, No. 5, pp. 2352-2358, 7 pages.

* cited by examiner

*Primary Examiner* — Janet L Epps-Smith
*Assistant Examiner* — Alexander W Nicol
(74) *Attorney, Agent, or Firm* — Wenderoth, Lind & Ponack, L.L.P.

(57) ABSTRACT

Provided is a method of preparing a somatic cell including converting a differentiated somatic cell of a mammal to other somatic cell by culturing the differentiated somatic cell in a medium for inducing differentiation of the somatic cell other than the differentiated somatic cell in the presence of a TGF-β pathway inhibitor.

1 Claim, 49 Drawing Sheets

|  | 1 | 2 | 3 | 4 | 5 |
|---|---|---|---|---|---|
| D4476 (2 μM) |  |  | + |  |  |
| ALK5IHII (2 μM) |  |  |  | + |  |
| SB431542 (2 μM) |  |  |  |  | + |
| general medium | + |  |  |  |  |
| induction medium (10%FBS) |  | + | + | + | + |

|  | 1 | 2 | 3 | 4 |
|---|---|---|---|---|
| D4476 (2 μM) |  | + |  |  |
| ALK5IHII (2 μM) |  |  | + |  |
| SB431542 (2 μM) |  |  |  | + |

Fig. 6
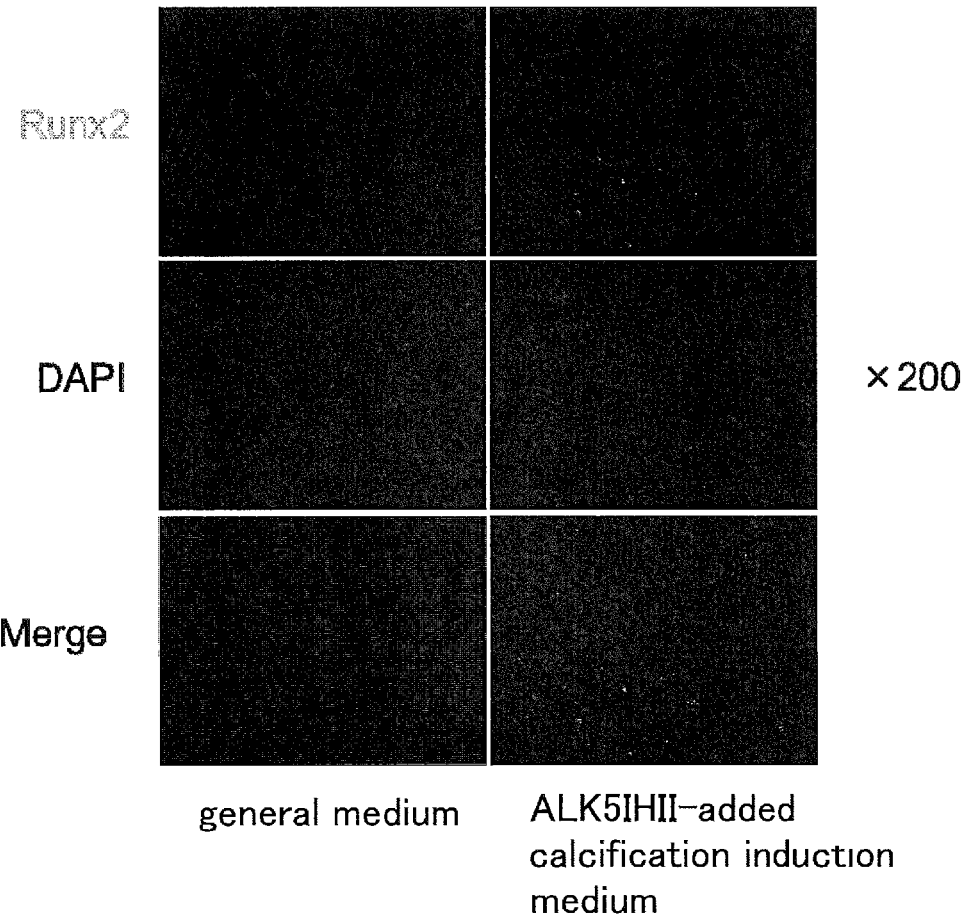
general medium | ALK5IHII-added calcification induction medium
×200
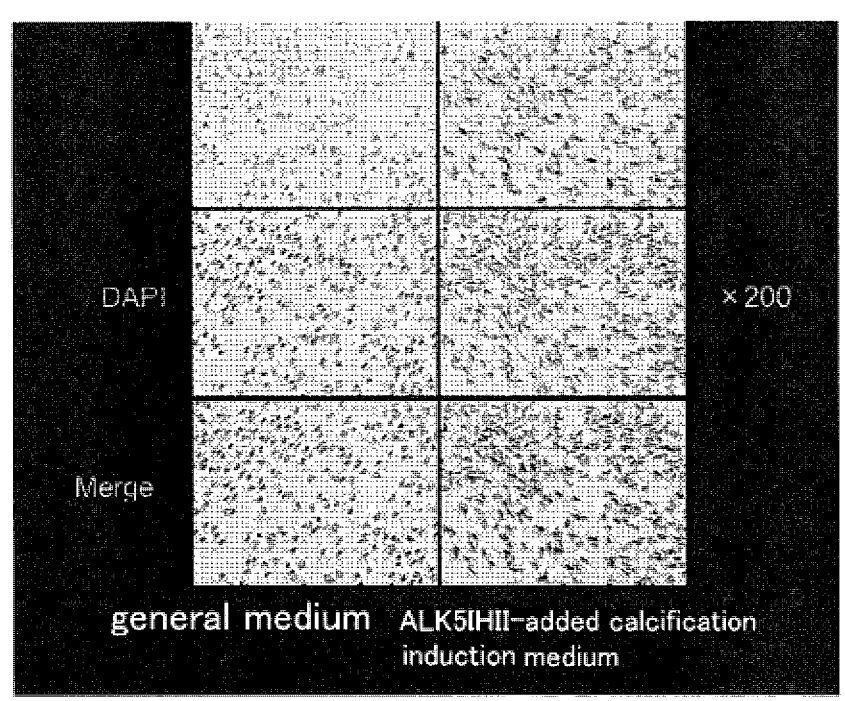

|  | 1 | 2 | 3 | 4 | 5 | 6 |
|---|---|---|---|---|---|---|
| T3 |  |  | + | + | + | + |
| Rosiglitazone |  |  | + | + | + | + |
| D4476 |  |  |  | + |  |  |
| SB431542 |  |  |  |  | + |  |
| ALK5IH |  |  |  |  |  | + |
| general medium | + |  |  |  |  |  |
| adipocyte induction medium |  | + | + | + | + | + |

|  | 1 | 2 | 3 | 4 | 5 | 6 |
|---|---|---|---|---|---|---|
| T3 |  |  | + | + | + | + |
| Rosiglitazone |  |  | + | + | + | + |
| D4476 |  |  |  | + |  |  |
| SB431542 |  |  |  |  | + |  |
| ALK5IH |  |  |  |  |  | + |
| general medium | + |  |  |  |  |  |
| adipocyte induction medium |  | + | + | + | + | + | quoted from
: Bernhard Schmierer & Caroline S. Hill, Nature Reviews Molecular Cell Biology 8, 970-982 (December 2007)

quoted from
  Y E. Zhang, "Non-smad pathways in TGF-β signaling" Cell Research 19: 128, 2009 quoted from
: Y. E. Zhang, "Non-smad pathways in TGF-β signaling" Cell Research 19: 128, 2009 quoted from
: Y. E. Zhang, "Non-smad pathways in TGF-β signaling" Cell Research 19: 128, 2009

Real-time RT-PCR $*p<0.05$ and $**p<0.01$ vs. the chon medium. $\#p<0.05$ and $\#\#p<0.01$ vs. ADSC.
Values are means ± S.D. (n=4).

ALP staining (day 10)

Alizarin red S staining (day 15)

| 1 | Control medium | - | - |
| 2 | WA medium | - | - |
| 3 | WA medium | - | Rosiglitazone (1 μM) |
| 4 | WA medium | ALK5 i II (8 μM) | - |
| 5 | WA medium | ALK5 i II (16 μM) | - |
| 6 | WA medium | ALK5 i II (8 μM) | Rosiglitazone (1 μM) |
| 7 | WA medium | ALK5 i II (16 μM) | Rosiglitazone (1 μM) | ical field, spinal cord injury, coxarthrosis, gon-

CELL PREPARATION METHOD

CROSS-REFERENCE TO THE RELATED APPLICATION

The present invention claims priority to Japanese Patent Application No. 2015-207529 filed on Oct. 21, 2015, which is incorporated herein by reference in their entireties.

TECHNICAL FIELD

The present invention mainly relates to a preparation method of a cell. More specifically, the present invention relates to a method for generating a cell by direct reprogramming. The present invention also relates to an inducer for converting a differentiated somatic cell to other somatic cell.

BACKGROUND ART

In recent years, a regenerative medicine technique that complements abnormality in function and morphology by transplanting cells into a patient to treat diseases has been attracting attention.

As for osteoblasts, for example, transplantation of osteoblasts to an affected area to repair a bone defect due to a bone tumor, trauma, osteomyelitis, etc., or a bone defect after curettage of a bone tumor or the like, can be expected to promote bone formation and to improve functional and morphological prognosis. In fact, for example, treatment performed by autologous transplantation of bone marrow cells collected from the cancellous bone of a patient has been carried out, and the effectiveness of the treatment is known. In this case, osteoblasts obtained by differentiation induction from mesenchymal stem cells contained in autologous bone marrow cells are considered to contribute to bone formation and remodeling. On the other hand, the prevalence of osteoporosis has been increasing in step with the aging of the population, and bone fractures of elderly persons may lead to prolonged bed rest. Transplantation of osteoblasts is considered to be capable of promoting the healing of bone fracture due to osteoporosis, external injury, or the like; intractable bone fracture; and pseudofracture. In addition, the transplantation of the osteoblasts may also be useful for, for example, rheumatoid arthritis, idiopathic osteonecrosis of the femoral head, arthrosis deformans, lumbar spondylosis deformans, spinal canal stenosis, disc herniation, spondylolysis, spondylolytic spondylolisthesis, scoliosis, cervical spondylotic myelopathy, ossification of posterior longitudinal ligament, spinal cord injury, coxarthrosis, gonarthrosis, slipped capital femoral epiphysis, osteomalacia, bone repair after surgery (such as breastbone repair after cardiac surgery), repair of a defect associated with artificial ankle joint surgery, osteomyelitis, and osteonecrosis.

On the other hand, periodontal disease is also referred to as a fourth lifestyle-related disease, occurs at a very high prevalence in persons, and causes various systemic diseases. As periodontal disease progresses, bone resorption of the alveolar bone occurs. Therefore, if osteoblasts can be supplied to a local bone resorption site with high efficiency, it will lead to regenerative treatment of the alveolar bone.

When transplantation of osteoblasts is combined with bone transplantation, artificial bone transplantation, artificial joints, or implants, therapeutic effects may be enhanced.

In regenerative medicine technique, a means of supply of the cells to be used is one of the problems.

For example, as osteoblasts for transplantation purposes, bone marrow mesenchymal stem cells, bone marrow cells including bone marrow mesenchymal stem cells, and the like have been used.

However, collection of the bone marrow is problematic. For example, the collection is highly invasive to a patient, and a sufficient number of bone marrow cells cannot be supplied in some cases. Alternatively, using human embryonic stem cells (ES cells) does not require the collection of bone marrow from a patient, and may supply a sufficient number of osteoblasts. However, in addition to ethical issues, it may cause a risk of tumorigenesis of residual ES cells after transplantation. Alternatively, using iPS cells does not require the collection of bone marrow from a patient, and may supply a sufficient number of osteoblasts. However, it may cause a risk of tumorigenesis of residual iPS cells after transplantation.

There is a similar problem for other cells as well.

Non-patent document 1 discloses introduction of a lentivirus vector including Osterix into human ES cells, and differentiation induction into osteoblasts in an osteogenic medium. Non-patent documents 2 and 3 disclose obtaining of osteoblasts from mouse iPS cells through conversion into MSCs by differentiation induction in an osteogenic medium.

Non-patent document 4 discloses obtaining of osteoblasts by introducing an adenovirus vector including Runx2 into mouse iPS cells, and subjecting the cells to differentiation induction in an osteogenic medium. As disclosed in non-patent documents 1 to 4, osteoblasts are generated from pluripotent stem cells, such as ES cells and iPS cells, by differentiation induction; therefore, the methods require long-term culture, and incur the risk of carcinogenesis.

When a gene group of a tissue-specific transcription factor is introduced into somatic cells, direct differentiation induction into tissue cells can be achieved without conversion into iPS cells (direct conversion (direct reprogramming)). Regarding this, for example, the following has been reported:

mouse fibroblast→chondrocyte (SOX9+Klf4+c-Myc genes were introduced);

mouse fibroblast→cardiac muscle cell (GATA4+Mef2c+Tbx5 genes were introduced);

mouse fibroblast→liver cell (Hnf4α+(Foxa1, Foxa2, or Foxa3) genes were introduced);

mouse fibroblast→neural stem cell (for example, Sox2+FoxG1 genes were introduced); and mouse or human cell→hematopoietic stem cell, and the like.

Patent document 1 discloses a method for efficiently generating an osteoblast having functionality by introducing a group of specific genes into somatic cells (direct conversion). However, in the method for introducing genes, cells may become tumorous due to the influence of the introduced gene or vector. There is also a problem of cost and time required for verification of safety. Therefore, a technique for inducing cells for transplantation without introducing a gene has been demanded.

DOCUMENT LIST

Patent Documents patent document 1: WO 2015/012377

Non-Patent Document non-patent document 1: Karner E et al. J Cell Physiol. 2009.
non-patent document 2: Li F et al. J Cell Biochem. 2010.

non-patent document 3: Biloussova G et al. Stem cells. 2011.
non-patent document 4: Tashiro K et al. Stem cells. 2009.

SUMMARY OF THE INVENTION

Problems to be Solved by the Invention

The present invention mainly aims to provide a cell preparation method, particularly a technique for converting a differentiated somatic cell to other somatic cell without gene transfer (technique of direct conversion (direct reprogramming)).

Means of Solving the Problems

The present inventor has found that a somatic cell as a starting material can be converted to a somatic cell other than the starting material by culturing a differentiated somatic cell of a mammal in the presence of a TGF-β pathway inhibitor in medium having various compositions.

There is no report of direct conversion (direct reprogramming) using a TGF-β pathway inhibitor.

The present invention encompasses the following preparation method of osteoblast, osteoblast inducer and a kit.

item 1. A method of preparing a somatic cell comprising converting a differentiated somatic cell of a mammal to other somatic cell by culturing the differentiated somatic cell in a medium for inducing differentiation of a somatic cell other than the aforementioned differentiated somatic cell in the presence of a TGF-β pathway inhibitor.

item 2. The method of item 1, wherein the TGF-β pathway inhibitor is a TGF-β/SMAD pathway inhibitor.

item 3. The method of item 1 or 2, wherein the TGF-β pathway inhibitor is a D4476, SB431542, LY2157299, SD208 or ALK5 inhibitor II.

item 4. The method of any one of items 1 to 4, wherein the TGF-β pathway inhibitor is an ALK5 inhibitor II.

item 5. The method of any one of items 1 to 4, wherein the fibroblast is converted to a mesenchymal cell.

item 6. The method of any one of items 1 to 4, wherein the fibroblast or keratinocyte is converted to an osteoblast.

item 7. The method of any one of items 1 to 4, wherein the fibroblast or peripheral blood mononuclear cell is converted to a white adipocyte.

item 8. The method of any one of items 1 to 4, wherein the fibroblast or keratinocyte is converted to a brown adipocyte.

item 9. The method of item 7 or 8, wherein the medium for inducing differentiation of the somatic cell comprises a Peroxisome Proliferator-Activated Receptor-γ (PPAR-γ) agonist.

item 10. The method of any one of items 1 to 4, wherein the fibroblast is converted to a chondrocyte.

item 11. The method of any one of items 1 to 4, wherein the fibroblast is converted to a myoblast.

item 12. The method of any one of items 1 to 4, wherein the fibroblast is converted to a Schwann cell.

item 13. The method of any one of items 1 to 4, wherein the keratinocyte is converted to a urothelial cell.

item 14. The method of any one of items 1 to 4, wherein the fibroblast is converted to a mesenchymal stem cell.

item 15. An inducer for converting a differentiated somatic cell to other somatic cell, comprising a TGF-β pathway inhibitor.

item 16. A kit for converting a differentiated somatic cell to other somatic cell, comprising a TGF-β pathway inhibitor and a medium for inducing differentiation of the aforementioned other somatic cell.

Effect of the Invention

In the present invention, other somatic cell can be provided in a short time from somatic cells differentiated by the action of a low-molecular-weight compound. The obtained somatic cells (e.g., mesenchymal stem cell and osteoblast) can be induced easily from somatic cells of a person who undergoes transplantation. Accordingly, when somatic cells themselves or tissues prepared from the cells are transplanted, problems, such as an immunological rejection response, do not occur. In addition, somatic cells can be induced directly from somatic cells without conversion into iPS cells or ES cells, and hence problems due to pluripotent stem cells, such as carcinogenesis, can be avoided. On the other hand, it is also possible to produce the cells in advance to storage in a bank and use the cells therefrom for allotransplantation or xenotransplantation to patients.

BRIEF DESCRIPTION OF THE DRAWINGS

FIG. 6 shows the results of immunostaining of Runx2 (staining Figure).

FIG. 4, FIG. 6 and FIG. 7 also show an inverted color image.

DESCRIPTION OF EMBODIMENTS

Figure 1:
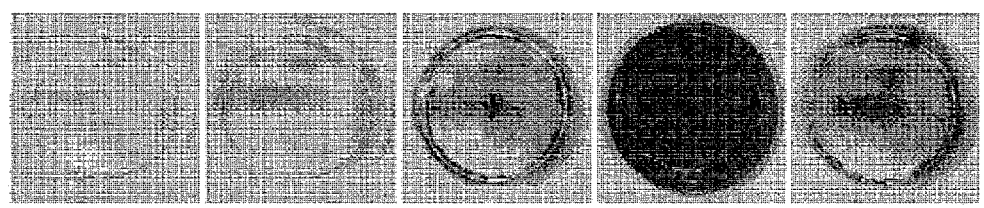
FIG. 1 shows the results of Alizarin Red S staining (staining Figure).

The present invention relates to a method for preparing other somatic cell by using a differentiated somatic cell of a mammal as a starting material. In other words, the present invention relates to a method for converting a differentiated somatic cell of a mammal to other somatic cell. The term "convert" herein means changing a somatic cell into a desired somatic cell. One preferred embodiment of the method of the present invention provides a method of converting a somatic cell into other somatic cell without reprogramming of cells, such as production of iPS cells, which is also called "direct conversion" or "direct reprogramming." It can also be said a method for directly converting a somatic cell to other somatic cell.

In a preferred embodiment of the method of the present invention, a somatic cell is converted to other somatic cell without introducing a gene. The term "without introducing a gene" means that a somatic cell is converted to another somatic cell with no change of the original genomic sequence of the somatic cell (this mainly means the nucleotide sequence of DNA) Alternatively, the term "without introducing a gene" means that a somatic cell is converted to another somatic cell based on the function of the original endogenous gene.

Differentiated Somatic Cell (Starting Material)

A differentiated somatic cell of a mammal to be used as a starting material of the method of the present invention is not particularly limited as long as it is derived from a mammal. The somatic cell means a cell other than reproductive cells from among the cells.

Examples of the kind of the somatic cell include fibroblast, epithelial cell (skin epidermal cell, mouth cavity mucosal epithelial cell, airway mucosal epithelial cell, intestinal mucosal epithelial cell and the like), epidermal cell, gingiva cell (e.g., gingiva fibroblast, gingiva epithelial cell), pulp cell, white adipocyte, subcutaneous fat, visceral fat, muscle, blood cell (e.g., peripheral blood mononuclear cell) and the like, with preference given to fibroblast, gingiva cell, mouth cavity mucosal epithelial cell, pulp cell, adipocyte, epidermal keratinocyte (keratinocyte), blood cell and the like.

In addition, somatic cells produced by inducing differentiation of or dedifferentiating or reprogramming somatic stem cells such as mesenchymal stem cell (MSC), neural stem cell, hepatic stem cell, intestinal stem cell, skin stem cell, hair follicle stem cell, pigment cell stem cell and the like can also be mentioned. In addition, different somatic cells produced by inducing differentiation of or dedifferentiating or reprogramming various somatic cells can also be mentioned. In addition, somatic cells produced by inducing differentiation of or dedifferentiating or reprogramming germline cells can also be mentioned.

Cultured cells are also recited and somatic cells induced by differentiation induction or dedifferentiation or reprogramming of cultured cells can also be mentioned.

Examples of the mammal include mouse, rat, hamster, human, dog, cat, monkey, rabbit, bovine, horse, swine and the like. Somatic cell is particularly preferably derived from human. The age of the individual from which the somatic cell is derived is not limited, and the individual may be adult, infant or fetal. In the present specification, cells derived from fetus and cells derived from placenta, amniotic membrane, umbilical cord and the like are also encompassed in the "somatic cell".

When generated somatic cells are transplanted to the body, somatic cells derived from the test subject who receives transplantation (autologous cells) are preferably used to reduce the risk of infection, rejection and the like. However, instead of autologous cells, somatic cells produced from somatic cells of other people or other animal can be used for transplantation. Alternatively, other somatic cells may be produced from somatic cells produced in advance from other people or other animals and used for transplantation.

Alternatively, somatic cells produced in advance from somatic cells of other people or other animals can be used for transplantation. That is, a somatic cell bank or a bank of somatic cell progenitor cells may be produced and used for transplantation purposes. In this case, to reduce the risk of rejection response and the like, blood type and MHC can be typed in advance. In addition, it is possible to confirm in advance the characters, tumorigenicity and the like of the somatic cells for transplantation.

Other Somatic Cell to be Prepared

Other somatic cell to be prepared by the method of the present invention is a somatic cell other than the somatic cell to be used as a starting material. The somatic cell to be differentiated under physiological conditions (particularly, in vivo) from a somatic cell to be used as a starting material is not included in "other somatic cell". For example, when a mesenchymal stem cell is used as a starting material, the osteoblast does not fall under "other somatic cell", since a mesenchymal stem cell is differentiated into an osteoblast in vivo.

Examples of the kind of the somatic cell to be prepared include mesenchymal stem cell (MSC), osteoblast, adipocyte (brown adipocyte or white adipocyte), chondrocyte, myoblast, urothelial cell, bone marrow stromal cell, tendon cell, hepatocyte, biliary epithelial cell, glial cell such as Schwann cell and the like, nerve cell, myocardial cell, smooth muscle cell, vascular endothelial cell, lymphatic endothelial cell and the like.

Furthermore, epidermal cell, pigment cell, hair follicle cell, nail matrix cell, connective tissue cell, lung and airway cell (airway epithelial cell, alveolar epithelial cell etc.), intestinal epithelial cell, glandular cell, hematopoietic stem cell, lymphocyte, granulocyte, monocyte, macrophage, mast cell, megakaryocyte, platelet, erythroblast, erythrocyte, lymphoreticular cell, antigen presenting cell, mammary gland epithelial cell, kidney cell (urinary tract system cell such as glomerulosa cell, renal tubular epithelial cell, urothelial cell and the like, etc.), reproductive system cell, corneal cell, conjunctivial cell, retinal cell, synovial cell, endocrine cell, pancreatic islet cell (insulin-producing cell (p cell) etc.), exocrine cell, hapatic stem cell, pancreatic stem cell, the intestinal stem cell, salivary gland stem cell and the like can be mentioned.

A combination of the somatic cell to be used as a starting material and the somatic cell to be prepared is not particularly limited.

In view of the high efficiency of preparation of a somatic cell, the somatic cell to be used as a starting material and the other somatic cell to be prepared are each preferably a somatic cell belonging to mesenchymal and differentiated from a mesenchymal stem cell.

Examples of the cell belonging to mesenchymal include mesenchymal stem cell (MSC), fibroblast, osteoblast, adipocyte, chondrocyte, myoblast, bone marrow stromal cell, tendon cell and the like. In addition, a cell known to be possibly differentiated from a mesenchymal stem cell such as hepatocyte, biliary epithelial cell, glial cell, nerve cell, myocardial cell, smooth muscle cell, vascular endothelial cell, lymphatic endothelial cell and the like is also encompassed in the "cell belonging to mesenchymal".

Osteoblast includes preosteoblasts, immature osteoblasts, mature osteoblasts, bone cells, and the like. Adipocyte includes white adipocyte and brown adipocyte, and white adipocyte includes adipose-derived stem cell, preadipocyte, mature adipocyte, hypertrophic adipocyte and the like. The brown adipocyte includes Beige cell, Brite cell and the like. Chondrocyte includes immature chondrocyte, mature chondrocyte, hypertrophic chondrocyte and the like. Myoblast includes muscle satellite cell, immature myoblast, mature myoblast, muscle cell, myotube cell, myofiber and the like. Similarly, the cells described in the present specification all includes cell lines represented by their names and showing different degrees of differentiation.

Specific examples of the embodiment of the present invention include a method of converting a fibroblast into a mesenchymal stem cell (MSC), a method of converting a fibroblast into an osteoblast, a method of converting a fibroblast into an adipocyte (e.g., a method of converting a fibroblast into a white adipocyte, a method of converting a fibroblast into a brown adipocyte and the like), a method of converting a fibroblast into a chondrocyte, a method of converting a fibroblast into a myoblast, a method of converting a keratinocyte into a urothelial cell, a method of converting a blood cell (e.g., peripheral blood mononuclear cell) into a white adipocyte and the like.

In addition, a method of converting a gingiva cell, oral mucosal epithelial cell, pulp cell, adipocyte, blood cells or the like as a starting material into a mesenchymal stem cell (MSC), osteoblast, adipocyte, chondrocyte or myoblast, and the like can be recited as an example.

The present invention also includes once converting a starting material into an intermediate cell (e.g., MSC, MSC-like cell, other somatic stem cell and the like) and then differentiating the intermediate cell into the final object cell (osteoblast, adipocyte, chondrocyte, myoblast and the like). Since intermediate cells and the like are among the somatic cells, direct conversion in the present specification includes going through them.

Medium

In the method of the present invention, a differentiated somatic cell is cultured in a medium for inducing a somatic cell other than the differentiated somatic cell (differentiation induction medium). As the differentiation induction medium, a known differentiation induction medium can be used according to the targeted somatic cell to be prepared.

The "medium for inducing other somatic cell other than differentiated somatic cell", "differentiation induction medium" refers to a medium containing components that mainly allow pluripotent stem cells (such as embryonic stem (ES) cells or iPS cells) to differentiate into the somatic cells.

For example, as the medium for inducing osteoblasts, for example, a general liquid medium added with one or more kinds of components such as ascorbic acid (e.g., concentration about 0.1 to 1000 µg/ml, preferably about 1 to 100 µg/ml); β-glycerophosphate (e.g., concentration about 0.1 to 1000 mM, preferably about 1 to 100 mM)β; glucocorticoid such as dexamethasone (about 1 nM to about 10 mM, preferably about 10 to 1000 mM) and hydrocortisone can be recited. Specific examples thereof include, but are not limited to, a medium obtained by adding 50 µg/ml ascorbic acid, 10 mM β-glycerophosphate, and about 100 nM dexamethasone (all of the concentrations are final concentrations) to a general medium, such as DMEM added with 10% FBS and 5% HS.

As a medium for inducing white adipocyte, a general medium added with one or more kinds of components such as insulin (e.g., concentration about 0.01-100 µg/mL, preferably about 0.1-10 µg/mL); 3-isobutyl-1-methylxanthine; IBMX) (e.g., concentration about 0.01-100 mM, more preferably about 0.1-10 mM); and dexamethasone (e.g., concentration about 0.01-100 M, more preferably about 0.1-10 µM) can be recited. Specific examples thereof include, but are not limited to, 10% FBS-added DMEM+MDI medium (0.5 mM 3-isobutyl-1-methylxanthine (IBMX), 0.5 µM dexametazone, and 1 µg/mL Insulin are added, 10% FBS-added DMEM).

In view of the high conversion efficiency to white adipocyte, a Peroxisome Proliferator-Activated Receptor-γ (PPAR-γ) agonist (e.g., concentration about 0.01-100 µM, more preferably about 0.1-10 µM) is preferably further added.

Examples of the PPAR-γ agonist include thiazolidinedione compounds such as Rosiglitazone, Ciglitazone, GW1929, nTZDpa, Pioglitazone Hydrochloride, Troglitazone and the like.

As a medium for inducing brown adipocyte, a general medium added with insulin (Insulin) (e.g., concentration about 0.01-100 µg/mL, more preferably about 0.1-10 µg/mL); 3-isobutyl-1-methylxanthine (IBMX) (e.g., concentration about 0.01-100 mM, more preferably about 0.1-10 mM); dexamethasone (Dexametazone) (e.g., concentration about 0.01-100 µM, more preferably about 0.1-10 µM) can be recited. In addition, indomethacin (Indometacin) (e.g., concentration about 0.001-10 mM, more preferably about 0.01-1 mM) may be added.

In view of the high conversion efficiency to brown adipocyte, it is preferable to further add a thyroid hormone (e.g., concentration about 0.01-100 nM, more preferably about 0.1-10 nM) and/or Peroxisome Proliferator-Activated Receptor-γ (PPAR-γ) agonist (e.g., concentration about 0.01-100 µM, more preferably about 0.1-10 µM), more preferably the both, to the medium.

Examples of the thyroid hormone include triiodothyronine (T3), thyroxine (T4) and the like.

Examples of the PPAR-γ agonist include thiazolidinedione compounds such as Rosiglitazone, Ciglitazone, GW1929, nTZDpa, Pioglitazone Hydrochloride, Troglitazone and the like.

Specific examples of the medium for inducing brown adipocyte include [1] DMEM medium added with FBS 10%, 0.5 mM IBMX, 125 nM Indomethacin, 1 microM Dexamethasone, 850 nM insulin, thyroid hormone such as 1 nM triiodothyronine (Triiodothyronine, T3) and 1 µM Rosiglitazone, and [2] DMEM medium added with 10% FBS, 850 nM insulin, 1 nM T3 and 1 µM Rosiglitazone. It is possible to use [1] on day 1-day 2 and [2] on day 3 and thereafter.

In addition, as a medium for inducing brown adipocyte from fibroblast, DMEM added with 1 nM T3, 1 µM Rosiglitazone, 0.5 mM isobutyl-1-methylxanthine (IBMX), 0.5 µM dexamethasone, 1 µg/mL Insulin and 10% FBS can be used. As a medium for inducing brown adipocyte from keratinocyte, HuMedia-KG2 added with 1 nM T3, 1 µM Rosiglitazone, 0.5 mM isobutyl-1-methylxanthine (IBMX), 0.5 µM dexamethasone and 1 µg/mL Insulin can be used.

However, the medium is not limited thereto.

Examples of the PPAR-γ agonist include thiazolidinedione compounds such as Rosiglitazone, Ciglitazone, GW1929, nTZDpa, Pioglitazone Hydrochloride, Troglitazone and the like.

As a medium for inducing mesenchymal stem cell, the media described in the following documents (1-1)-(1-4) can be used, but the medium is not limited thereto.

(1-1) M. D. Hoffman and D. S. W. Benoit, J Tissue Eng Regen Med. 2013 Apr. 1. doi: 10.1002/term.1736
(1-2) C-Y Li, et al., Stem Cell Res Ther. 2015 Apr. 13; 6:55. doi: 10.1186/s13287-015-0066-5.
(1-3) B. Gharibi and F. J. Hughes, Stem Cells Transl Med. 2012 November; 1(11):771-82. doi: 10.5966/sctm.2010-0031. Epub 2012 Oct. 23
(1-4) S. K. Both et al. Tissue Eng. 2007 January; 13(1):3-9.
(1-5) F. Ng et al., Blood. 2008 Jul. 15; 112(2):295-307. doi: 10.1182/blood-2007-07-103697. Epub 2008 Mar. 10.
(1-6) Hynes K. et al., J Dent Res. 2013 September; 92(9): 833-9.

As a medium for inducing chondrocyte, a known one can be used. The media described in the following documents (2-1)-(2-4) can be used, but the medium is not limited thereto.

(2-1) H. Outani, et al., PLOS One, 8(10): e77365. doi: 10.1371/journal.pone.0077365
(2-2) G.-I. Im, et al. Tissue Engineering. March 2006, 12(3): 527-536. doi: 10.1089/ten. 2006. 12. 527.
(2-3) H-J. Kim and G.-I. Im, Journal of Orthopaedic Research, Volume 27, Issue 5, pages 612-619, May 2009
(2-4) A. M. Ibrahim et al., Microscopy Research and Technique, Volume 78, Issue 8, pages 667-675, August 2015.

As a medium for inducing myoblast, a known one can be used. For example, Ham's/F10 medium added with 5% FBS, 50 microG/ml Bovine Fetuin, 10 nG/ml hEGF, 1 nG/ml bFGF, 10 microG/ml Insulin, 0.4 microG Dexamethasone; DMEM medium added with 10% FBS, 10 microM 5-azacytidine, 10 ng/mL VEGF, 10 ng/mL IGF-1, 10 ng/mL bFGF; bMEM medium added with 5% Horse serum, 10 ng/mL and the like can be used. For example, the medium described in a document: Int J Mol Med. 2014 January; 33(1):160-70. doi: 10.3892/ijmm.2013.1555. Epub 2013 Nov. 13. can be used. However, the medium is not limited thereto.

As a medium for inducing nerve cell, a known one can be used. For example, [1] DMEM medium added with 1 microM Retinoic acid (RA), 5 microM FSK, [2] DMEM medium added with 1 microM RA, 5 microM FSK, 10 ng/mL bFGF, [3] DMEM medium added with 1 microM RA, 1 microM FSK, 10 ng/mL bFGF, 100 ng/mL SHH are used, wherein [1] can be used on days 1 to 3, [2] can be used on days 4 and 5, and [3] can be used on day 6 and the following. In addition, for example, the medium described in a document: Yan Y. et al., Stem Cells Transl Med. 2013 November; 2(11):862-70. However, the medium is not limited thereto.

As a medium for inducing glial cell and nerve cell, a known one can be used. For example, the media described in documents: L. Hook et al., Neurochemistry International. Volume 59, Issue 3, September 2011, Pages 432-444 and Selvaraj V. et al., Front Biosci (Landmark Ed). 2012 Jan. 1; 17:65-89. can be used. However, the medium is not limited thereto.

As a medium for inducing glial cell, a known one can be used. For example, the medium described in a document: Duan L. et al., Stem Cells Transl Med. 2015 May; 4(5):437-47. can be used. However, the medium is not limited thereto.

As a medium for inducing Schwann cell, a known one can be used. For example, a general medium such as DMEM medium (Dulbecco's modified Eagle medium) added with 10% FBS (fetal bovine serum) and the like added with one or more kinds (preferably, all) of components such as about 1-20 μM (particularly, about 5 μM) of forskolin; about 2-50 ng/ml (particularly, about 10 ng/ml) of bFGF (basic fibroblast growth factor); about 2-50 ng/ml (particularly, about 10 ng/ml) of PDGF (Platelet-Derived Growth Factor); about 50-1000 ng/ml (particularly, about 200 ng/ml) of human neuregulin-β1 (alias, heregulin, GGF (Glial growth factor)) and the like, (Schwann cell induction medium), can be used (the following concentrations are all final concentrations). In one embodiment, the media described in the following documents (3-1)-(3-2) (medium capable of inducing Schwann cell from undifferentiated adypocyte-derived stem cell) can be used.

(3-1) Kingham P J, DF Kalbermatten, D Mahay, et al: Adipose-derived stem cells differentiate into a Schwann cell phenotype and promote neurite outgrowth in vitro. ExpNeurol, 2007; 207:267-274.

(3-2) Liu Y, Zhang Z, Qin Y, Wu H, Lv Q, Chen X, Deng W: A new method for Schwann-like cell differentiation of adipose derived stem cells. Neurosci Lett. 2013 Sep. 13; 551:79-83.

As a medium for inducing myocardial cell, a known one can be used. For example, the medium described in a document: Y. J. Nam et al., Proc Natl Acad Sci USA. 2013 Apr. 2; 110(14):5588-93. doi: 10.1073/pnas.1301019110. Epub 2013 Mar. 4. can be used. However, the medium is not limited thereto.

As a medium for inducing vascular endothelial cell, a known one can be used. For example, DMEM added with 10% FBS, 100 ng/mL VEGF can be used. In addition, the method described in Chatterjee I. et al., Methods Mol Biol. 2015 Feb. 17. PMID:25687301 can be performed. However, the medium is not limited thereto.

As a medium for inducing smooth muscle cell, a known one can be used. For example, the method described in Wang Y. et al., Biomaterials. 2014 October; 35(32):8960-9. can be performed. However, the medium is not limited thereto.

As a medium for inducing mast cell, a known one can be used. For example, [1] DMEM medium added with 15% FBS, 20 ng/mL VEGF, [2] IDMD medium added with 10% FBS, 10 ng/mL IL-3, 100 ng/mL IL-6, 10 ng/mL Flt3 L, 10 ng/mL TPO, 10 ng/mL VEGF, [3] IDMD added with 10% Stem span, 100 ng/mL SCF, 100 ng/mL IL-6, 10 ng/mL Flt3 L, 10 ng/mL TPO, 10 ng/mL VEGF are used, wherein [1] can be used on days 1 to 8, [2] can be used on days 9 to 18, and [3] can be used on day 19 and the following. However, the medium is not limited thereto.

As a medium for inducing β cell (insulin-producing cell), a known one can be used. For example, DMEM added with 15% FBS, 100 ng/mL Activin A, 10 nM GLP-1, 10 mM Nicotinamide, 20 ng/mL EGF, 10 ng/mL bFGF, ITS can be used. In addition, the media described in Shahjalal H M et al., J Mol Cell Biol. 2014 October; 6(5):394-408. and Noguchi H. et al., Curr Diabetes Rev. 2010 May; 6(3):184-90. can be used. However, the medium is not limited thereto.

As a medium for inducing hepatocyte, a known one can be used. For example, the medium described in Y. Yu et al., Stem Cell Res. 2012 November; 9(3):196-207 can be used. However, the medium is not limited thereto.

As a medium for inducing gastrointestinal tract cell, a known one can be used. For example, the media described in Spence J R. et al. Nature. 2011 Feb. 3; 470(7332):105-9. and Wells J M and Spence J R. Development. 2014 February; 141(4):752-60. can be used. However, the medium is not limited thereto.

As a medium for inducing lung and airway cells, a known one can be used. For example, the medium described in Ghaedi M. et al., J Clin Invest. 2013 November; 123(11): 4950-62. can be used. However, the medium is not limited thereto.

As a medium for inducing urothelial cell, a known one can be used. For example, the media described in Osborn S. L. et al., Stem Cells Transl Med. 2014; 3(5): 610-619. and Kang M. et al., Int. J. Mol. Sci. 2014, 15(5), 7139-7157 can be used. However, the medium is not limited thereto.

As a medium for inducing kidney cell, a known one can be used. For example, the media described in Lam A Q, et al. Semin Nephrol. 2014 July; 34(4):445-61. and Lam A Q, and Bonventre J V. Curr Opin Organ Transplant. 2015 April; 20(2):187-92. can be used. However, the medium is not limited thereto.

As a medium for inducing hematopoietic stem cell, a known one can be used. For example, the medium described in Wang Y, et al., Proc Natl Acad Sci USA. 2005; 102: 19081-6. can be used. However, the medium is not limited thereto.

As a medium for inducing blood cell, a known one can be used. For example, the medium described in Nakayama N. et al., Blood. 1998 Apr. 1; 91(7):2283-95. can be used. However, the medium is not limited thereto.

As a medium for inducing lymphocyte, a known one can be used. For example, the media described in Carpenter L. et al., Blood. 2011 Apr. 14; 117(15):4008-11. and Vodyanik M A, et al., Blood. 2005; 105:617-26. can be used. However, the medium is not limited thereto.

As a medium for inducing erythroblast, a known one can be used. For example, the medium described in Lu S J, et al., Blood. 2008; 112:4475-84. can be used. However, the medium is not limited thereto.

As a medium for inducing megakaryocyte, a known one can be used. For example, the medium described in Takayama N. and Eto K. Methods Mol Biol. 2012; 788:205-17. can be used. However, the medium is not limited thereto.

As a medium for inducing dendritic cell and macrophage, a known one can be used. For example, the medium described in Senju S. et al., Gene Ther. 2011 September; 18(9):874-83. can be used. However, the medium is not limited thereto.

As a medium for inducing granulocyte, a known one can be used. For example, the medium described in Morishima T. et al., J Cell Physiol. 2011 May; 226(5):1283-91. can be used. However, the medium is not limited thereto.

As a medium for inducing retinal cell, a known one can be used. For example, the medium described in Maeda T. et al., J Biol Chem. 2013 Nov. 29; 288(48):34484-93 can be used. However, the medium is not limited thereto.

As a medium for inducing corneal cell, a known one can be used. For example, the medium described in Yu D. et al., Cell Biol Int. 2013 January; 37(1):87-94. can be used. However, the medium is not limited thereto.

As a general medium, general liquid media such as Dulbecco's Modified Eagle's Medium, EMEM (Eagle's minimal essential medium) and the like can be used. Where necessary, components such as serum components (Fetal Bovine Serum (FBS), Human Serum (Serum)), antibiotics such as streptomycin, penicillin and the like, Non-Essential Amino Acid and the like can be added.

TGF-β Pathway Inhibitor

In the method of the present invention, cultivation is performed in a medium for inducing other somatic cell in the presence of a TGF-β pathway inhibitor.

The "TGF-β pathway inhibitor" encompasses a TGF-β/SMAD pathway inhibitor, a TGF-β/Erk pathway inhibitor, a TGF-β/JNK pathway inhibitor, a TGF-β/p38 pathway inhibitor and a TGF-β/RhoA pathway inhibitor. That is, an inhibitor that suppresses any one or more of a molecule of TGF-β receptor family, cytokine of TGF-β super family to be a ligand thereof, and molecules constituting TGF-β/SMAD pathway, TGF-β/Erk pathway, TGF-β/JNK pathway, TGF-β/p38 pathway, TGF-β/RhoA pathway at the downstream of the molecule of TGF-β receptor family is the TGF-β inhibitor of the present invention.

The "TGF-β pathway inhibitor" encompasses not only low-molecular-weight compounds which are inhibitors in the narrow sense but also cytokine-neutralizing antibody; receptor antagonist; soluble receptor; antibody, aptamer and peptide that bind to a protein of a pathway and have an activity to inhibit action thereof; variant protein, peptide and analog thereof that act as dominant negatives; siRNA, shRNA and microRNA that suppress expression of a protein of a pathway and the like.

TGF-β/SMAD Pathway Inhibitor

Figure 16:
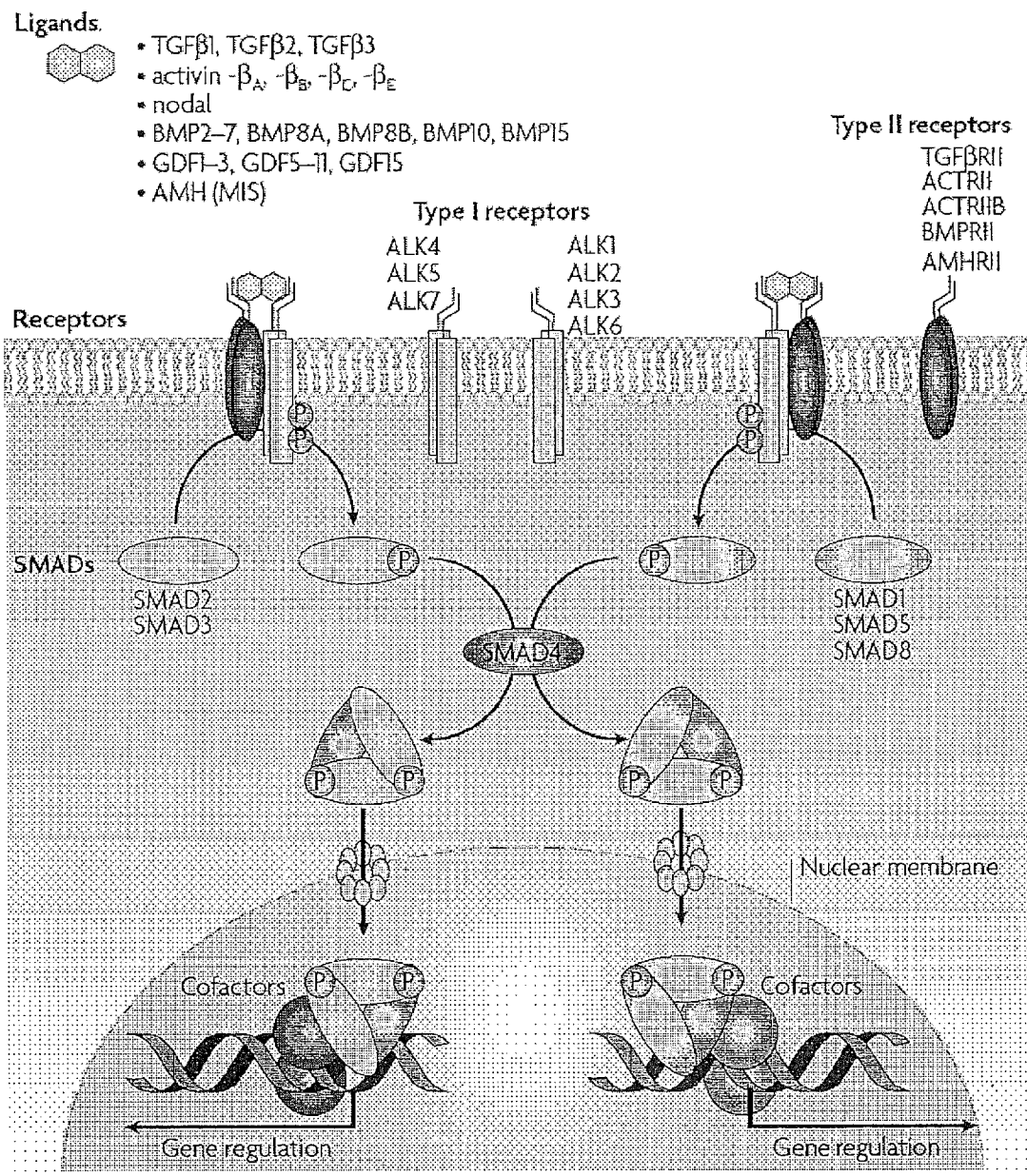
FIG. 16 schematically shows a TGF-β/SMAD pathway.

TGF-β/SMAD pathway inhibitor means a compound capable of inhibiting the activity of a protein belonging to the TGF-β/SMAD pathway. The TGF-β/SMAD pathway is a signal pathway known to those of ordinary skill in the art and is schematically shown in FIG. 16 (quoted from Chen G et al, Int J Biol Sci, 2012).

The TGF-β/SMAD pathway is mainly constituted of a ligand constituted of protein belonging to the TGF-β superfamily (TGF-β1, TGF-β2, TGF-β3, activin-βA, activin-βB, activin-βC, activin-βE, nodal, BMP2, BMP3, BMP4, BMP5, BMP6, BMP7, BMP8A, BMP8B, BMP10, BMP15, GDF1, GDF2, GDF3, GDF5, GDF6, GDF7, GDF8, GDF9, GDF10, GDF11, GDF15, AMH (MIS) and the like), a protein belonging to the TGF-β type I receptor family and a protein belonging to the TGF-β type II receptor family constituting heterodimeric receptors, and protein belonging to the SMAD family and is an intracellular signaling molecule (effector) (particularly SMAD2, SMAD3, SMAD4, SMAD1, SMAD5 or SMAD8).

In the TGF-β/SMAD pathway, when the ligand binds to a dimeric receptor, TGF-β type I receptor protein, which is a kinase type receptor, phosphorylates the SMAD protein and transmits a signal downstream. In the present specification, therefore, a molecule that suppresses any of the cytokine of TGF-β superfamily and the proteins of TGF-β type I receptor family, TGF-β type II receptor family and SMAD family (particularly SMAD2, SMAD3, SMAD4, SMAD1, SMAD5 or SMAD8) is called a TGF-β/SMAD pathway inhibitor.

As one of the embodiments of the TGF-β/SMAD pathway inhibitor, an inhibitor (ALK inhibitor) of ALK proteins (ACVRL1 (ALK1), ACVR1 (ALK2), BMPR1A (ALK3), ACVR1B (ALK4), TGFBR1 (ALK5), BMPR1B (ALK6), ACVR1C (ALK7)) belonging to the TGF-β type I receptor family (also referred to as Activin receptor like kinase (ALK) family) is recited. Also, an inhibitor of a protein (ACVR2A (ACTRII), ACVR2B (ACTRIIB), TGFBRII (AAT3), BMPR2 (PPH1)) belonging to the TGF-β type II receptor family is recited.

Specific examples include D4476 (4-[4-(2,3-dihydro-1,4-benzodioxin-6-yl)-5-(2-pyridinyl) 1H-imidazol-2-yl]-benzamide), ALK5 Inhibitor II (2-(3-(6-Methylpyridin-2-yl)-1H-pyrazol-4-yl)-1,5-naphthyridine; alias RepSox), GW7-88388, SD-208 (2-(5-Chloro-2-fluorophenyl)-4-[(4-pyridyl)amino]pteridine) as inhibitors of ALK5; LY2109761, LY2157299 (Galunisertiv, 4-[5,6-dihydro-2-(6-methyl-2-pyridinyl)-4H-pyrrolo[1,2-b]pyrazol-3-yl]-6-quinolinecarboxamide), LY364947 (4-[3-(2-pyridinyl)-1H-pyrazol-4-yl]-quinoline) as inhibitors of ALK5 and TGFβRII (AAT3); SM16 (4-(5-(benzo[d][1,3]dioxol-5-yl)-4-(6-methylpyridin-2-yl)-1H-imidazol-2-yl)bicyclo[2.2.2]octane-1-carboxamide), EW-7197, SB525334 ((6-[2-tert-butyl-5-(6-methylpyridin-2-yl)-1H-imidazol-4-yl]-quinoxaline) as inhibitors of ALK4 and ALK5; SB431542 (4-[4-(1,3-Benzodioxol-5-yl)-5-(pyridin-2-yl)-1H-imidazol-2-yl]benzamide), SB505124, A83-01 as inhibitors of ALK4, ALK5 and ALK7; LDN-193189, PKC-412, Apigenin, DMH1, ML347 as inhibitors of ALK2 and ALK3; LDN-214117 as inhibitor of ALK1 and ALK2; LDN-212854 as inhibitor of ALK1, ALK2 and ALK3; and K02288 as inhibitor of ALK1, ALK2, ALK3 and ALK6.

As a TGF-β/SMAD pathway inhibitor, a compound represented by the following formula (1) or (2) or a salt thereof described in Gellibert, F et al. J. Med. Chem. 2004, 47, 4494-4506 can also be used.

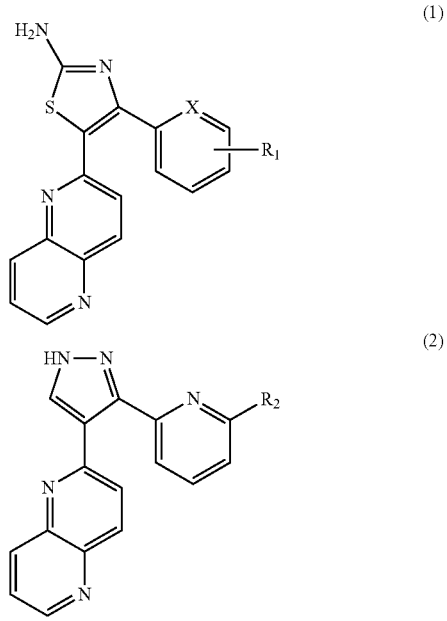

wherein X is CH or N,
R₁ is H, a methyl group or halogen (e.g., fluorine, chlorine, bromine or iodine), and
R₂ is H or a methyl group.

As the ALK inhibitor, one having at least an inhibitory activity against ALK5 (ALK5 inhibitor) is preferable in view of the high effect. One having a specific inhibitory activity against ALK4 and ALK5, or ALK5 (of ALK proteins, one having remarkably high inhibitory activity against the protein) is preferable in view of the particularly high effect.

Specific examples of preferable ALK inhibitor include D4476, SB431542, SD208, LY2157299 and ALK5 Inhibitor II, and ALK5 Inhibitor II is particularly preferable. D4476, SB431542, SD208 and ALK5 Inhibitor II are highly efficient in converting fibroblast to osteoblast. LY2157299 and ALK5 Inhibitor II are highly efficient in converting fibroblast to brown adipocyte.

Another embodiment of the TGF-β/SMAD pathway inhibitor is, for example, an SMAD protein inhibitor. Among others, inhibitors of SMAD2 and SMAD3, further SMAD4 at the downstream of ALK5 are preferable.

TGF-β/ERK Pathway Inhibitor

Figure 17:
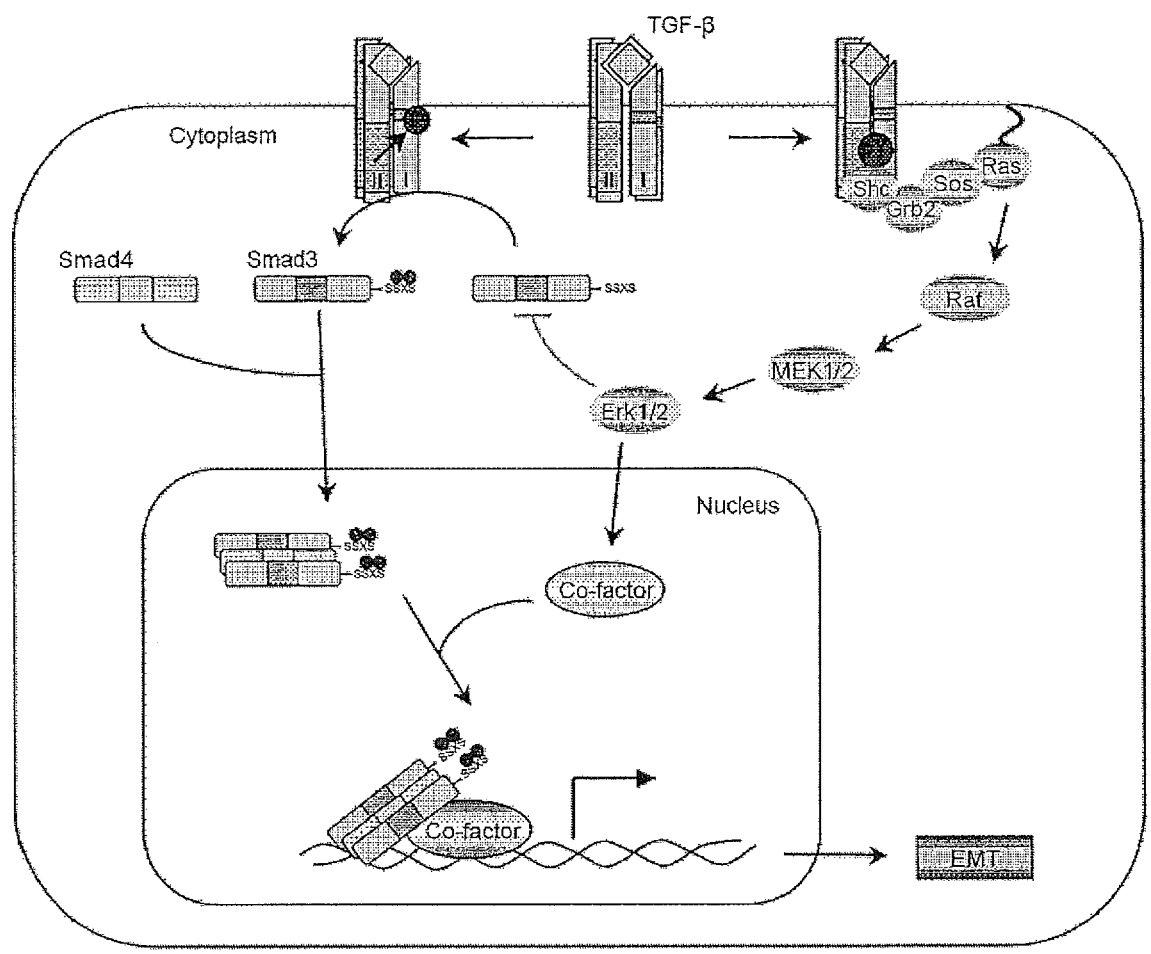
FIG. 17 schematically shows a TGF-β/SMAD pathway and a TGF-β/ERK pathway.

TGF-β/ERK pathway inhibitor means a compound capable of inhibiting the activity of protein belonging to the TGF-β/ERK pathway. TGF-β/ERK pathway is a signal pathway known to those of ordinary skill in the art and is schematically shown in FIG. 17 (quoted from Y. E. Zhang, "Non-smad pathways in TGF-β signaling" Cell Research 19: 128, 2009).

The TGF-β/Erk pathway is mainly comprised of a ligand constituted of protein belonging to the TGF-β superfamily (TGF-β1, TGF-β2, TGF-β3, activin-βA, activin-βB, activin-βC, activin-βE, nodal, BMP2, BMP3, BMP4, BMP5, BMP6, BMP7, BMP8A, BMP8B, BMP10, BMP15, GDF1, GDF2, GDF3, GDF5, GDF6, GDF7, GDF8, GDF9, GDF10, GDF11, GDF15, AMH and the like), protein belonging to the TGF-β type I receptor family and protein belonging to the TGF-β type II receptor family constituting heterodimeric receptors, and Raf, MEK1/2, Erk1/2 proteins which are intracellular signal transduction molecules.

In the TGF-β/Erk pathway, when the ligand binds to a dimeric receptor, a signal is transmitted to downstream; Raf, MEK1/2, Erk1/2. In the present specification, therefore, a molecule that suppresses any of the cytokine of TGF-β superfamily, TGF-β type I receptor family, TGF-β type II receptor family, Raf, MEK1/2 and Erk1/2 is called a TGF-β/SMAD pathway inhibitor.

As one embodiment of the TGF-β/Erk pathway inhibitor, for example, the aforementioned inhibitor of ALK protein can be recited.

As another embodiment of the TGF-β/Erk pathway inhibitor, for example, inhibitors such as an inhibitor of Raf, an inhibitor of MEK1, an inhibitor of MEK2, an inhibitor of Erk1 and an inhibitor of Erk2 can be recited. Of these, an inhibitor of Erk1 and an inhibitor of Erk2 are preferable.

TGF-β/JNK Pathway Inhibitor

Figure 18:
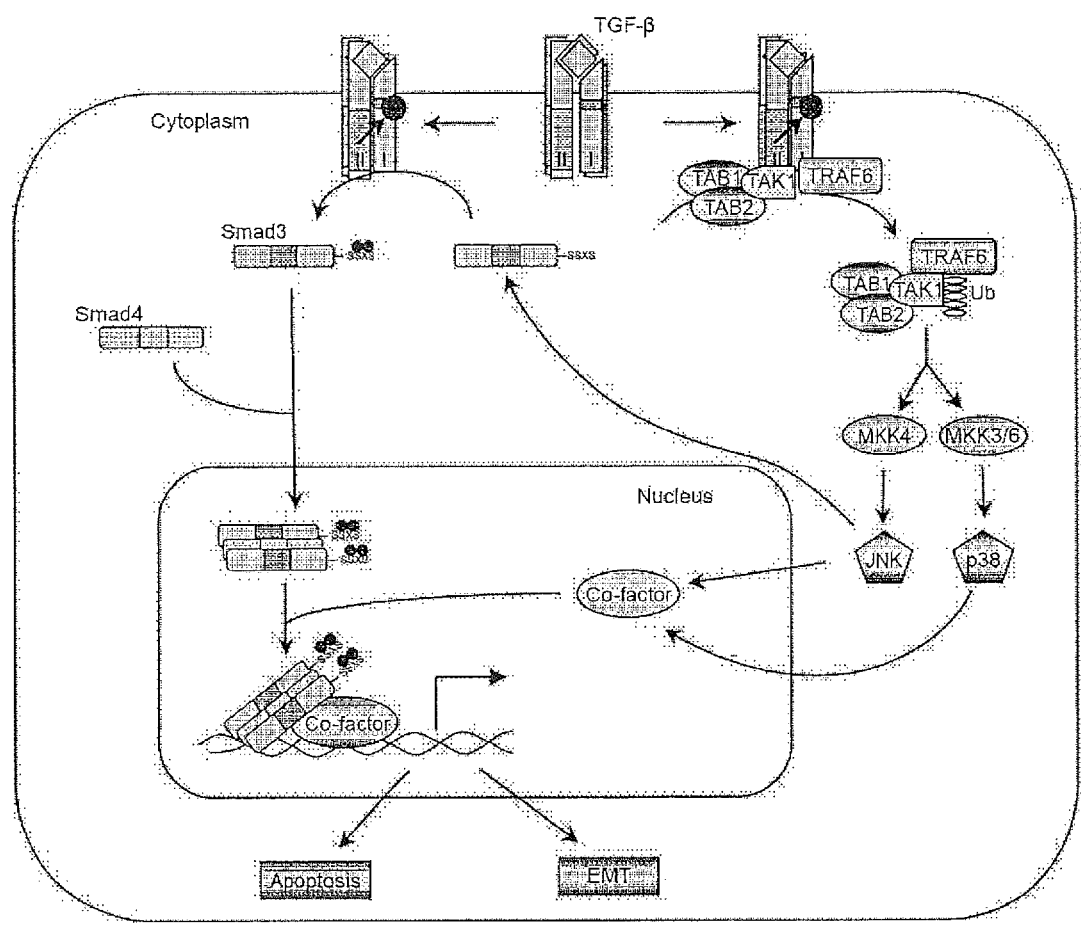
FIG. 18 schematically shows a TGF-β/SMAD pathway, a TGF-β/JNK pathway and a TGF-β/p38 pathway.

TGF-β/JNK pathway inhibitor means a compound capable of inhibiting the activity of a protein belonging to the TGF-β/JNK pathway. The TGF-β/JNK pathway is a signal pathway known to those of ordinary skill in the art and is schematically shown in FIG. 18 (quoted from Y. E. Zhang, "Non-smad pathways in TGF-β signaling" Cell Research 19: 128, 2009).

TGF-β/JNK pathway is mainly comprised of a ligand constituted of a protein belonging to the TGF-β superfamily (TGF-β1, TGF-β2, TGF-β3, activin-3A, activin-βB, activin-βC, activin-βE, nodal, BMP2, BMP3, BMP4, BMP5, BMP6, BMP7, BMP8A, BMP8B, BMP10, BMP15, GDF1, GDF2, GDF3, GDF5, GDF6, GDF7, GDF8, GDF9, GDF10, GDF11, GDF15, AMH and the like), a protein belonging to the TGF-β type I receptor family and a protein belonging to the TGF-β type II receptor family constituting a heterodi-meric receptors, and TAB1/2, TAK1, TRAF6, MKK4, JNK proteins, which are intracellular signal transduction molecules.

In the TGF-β/JNK pathway, when the ligand binds to a dimeric receptor, a signal is transmitted to downstream; TAB1/2, TAK1, TRAF6, MKK4, JNK. In the present specification, therefore, a molecule that suppresses any of cytokine of TGF-β superfamily, TGF-β type I receptor family, TGF-β type II receptor family, TAB1/2, TAK1, TRAF6, MKK4 and JNK is called a TGF-β/JNK pathway inhibitor.

As one embodiment of the TGF-β/JNK pathway inhibitor, for example, the aforementioned inhibitor of ALK protein can be recited.

As another embodiment of the TGF-β/JNK pathway inhibitor, for example, inhibitors such as an inhibitor of TAK1, an inhibitor of MKK4 and an inhibitor of JNK can be recited. Of these, an inhibitor of JNK is preferable.

TGF-β/p38 Pathway Inhibitor

In the method of the present invention, cultivation is performed in a medium for inducing other somatic cell in the presence of a TGF-β/p38 pathway inhibitor.

TGF-β/p38 pathway inhibitor means a compound capable of inhibiting the activity of a protein belonging to the TGF-β/p38 pathway. The TGF-β/p38 pathway is a signal pathway known to those of ordinary skill in the art and is schematically shown in FIG. 18 (quoted from Y. E. Zhang, "Non-smad pathways in TGF-β signaling" Cell Research 19: 128, 2009).

The TGF-β/p38 pathway is mainly comprised of a ligand constituted of a protein belonging to the TGF-β superfamily (TGF-β1, TGF-β2, TGF-β3, activin-βA, activin-βB, activin-βC, activin-βE, nodal, BMP2, BMP3, BMP4, BMP5, BMP6, BMP7, BMP8A, BMP8B, BMP10, BMP15, GDF1, GDF2, GDF3, GDF5, GDF6, GDF7, GDF8, GDF9, GDF10, GDF11, GDF15, AMH and the like), a protein belonging to the TGF-β type I receptor family and a protein belonging to the TGF-β type II receptor family constituting a heterodimeric receptors, and TAB1/2, TAK1, TRAF6, MKK3, MKK6, a protein belonging to the p38 family, which are intracellular signal transduction molecules.

In the TGF-β/p-38 pathway, when the ligand binds to a dimeric receptor, a signal is transmitted to downstream; TAK, MKK3 or MKK6, p-38 family (particularly p-38α, p-38β). In the present specification, therefore, a molecule that suppresses any of the cytokine of TGF-β superfamily, TGF-β type I receptor family, TGF-β type II receptor family, TAB1/2, TAK1, TRAF6, MKK3, MKK6, p38 family protein (particularly p38α, p38β) is called a TGF-β/SMAD pathway inhibitor.

As one embodiment of the TGF-β/p38 pathway inhibitor, for example, the aforementioned inhibitor of ALK protein can be recited.

As another embodiment of the TGF-β/p38 pathway inhibitor, for example, an inhibitor of TAK1, an inhibitor of MKK3, an inhibitor of MKK6 and an inhibitor of p38 can be recited. Of these, an inhibitor of p38 is preferable.

TGF-β/RhoA Pathway Inhibitor

In the method of the present invention, cultivation is performed in a medium for inducing other somatic cell in the presence of a TGF-β/RhoA pathway inhibitor.

Figure 19:
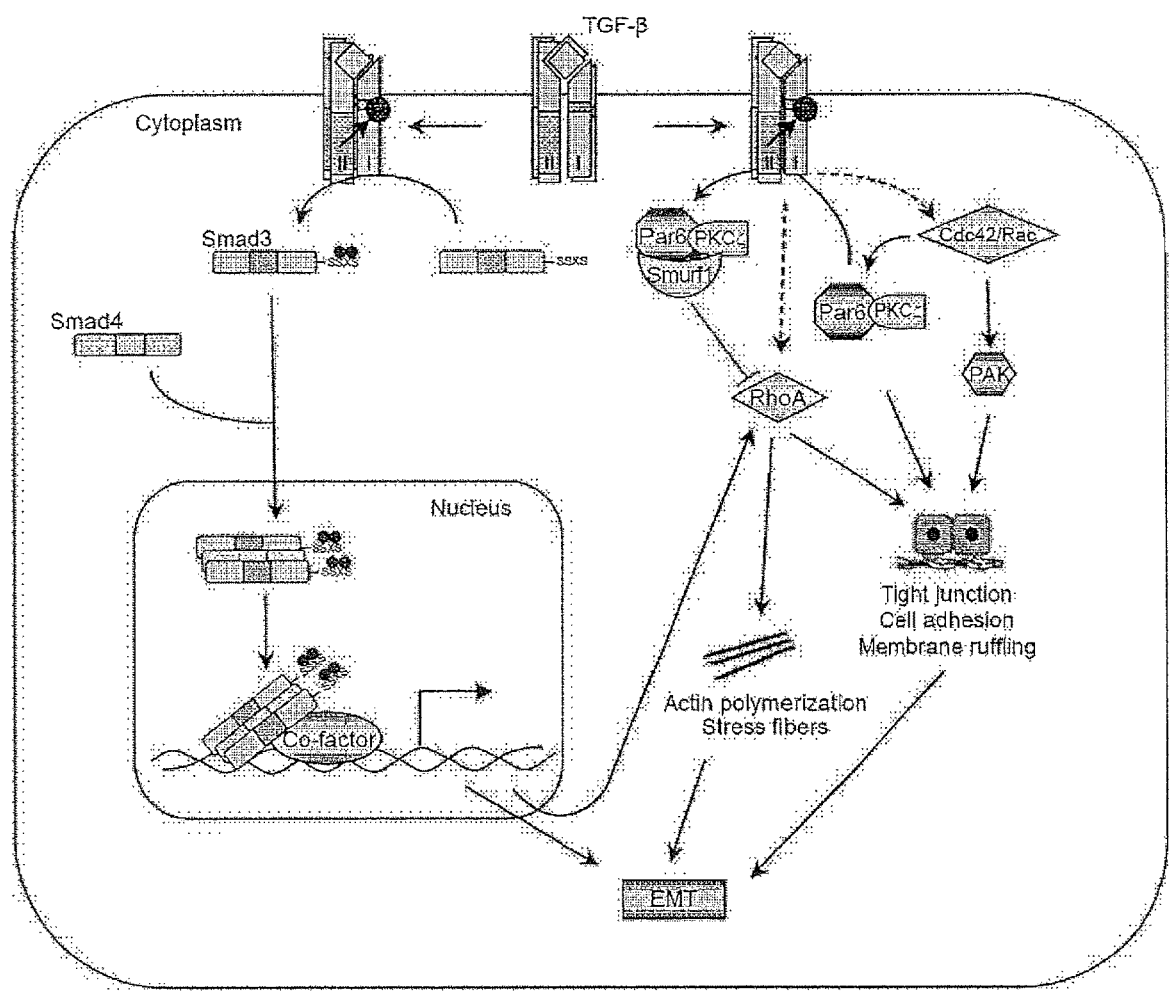
FIG. 19 schematically shows a TGF-β/SMAD pathway and a TGF-β/RhoA pathway.

TGF-β/RhoA pathway inhibitor means a compound capable of inhibiting the activity of a protein belonging to the TGF-β/RhoA pathway. The TGF-β/RhoA pathway is a signal pathway known to those of ordinary skill in the art and is schematically shown in FIG. 19 (quoted from Y. E. Zhang, "Non-smad pathways in TGF-β signaling" Cell Research 19: 128, 2009), and.

The TGF-β/RhoA pathway is mainly constituted of a ligand constituted of a protein belonging to the TGF-β superfamily (TGF-β1, TGF-β2, TGF-β3, activin-βA, activin-βB, activin-βC, activin-βE, nodal, BMP2, BMP3, BMP4, BMP5, BMP6, BMP7, BMP8A, BMP8B, BMP10, BMP15, GDF1, GDF2, GDF3, GDF5, GDF6, GDF7, GDF8, GDF9, GDF10, GDF11, GDF15, AMH and the like), a protein belonging to the TGF-β type I receptor family and a protein belonging to the TGF-β type II receptor family constituting a heterodimeric receptor, and Par6, PKCζ, Smurf1, RhoA proteins, which are intracellular signal transduction molecules.

In the TGF-β/RhoA pathway, when the ligand binds to a dimeric receptor, a signal is transmitted to downstream; TAK, MKK3 or MKK6, p-38 family (particularly p-38α, p-38β). In the present specification, therefore, a molecule that suppresses any of the cytokine of TGF-β superfamily, TGF-β type I receptor family, TGF-β type II receptor family, Par6, PKCζ, Smurf1, RhoA is called a TGF-β/RhoA pathway inhibitor.

As one embodiment of the TGF-β/RhoA pathway inhibitor, for example, the aforementioned inhibitor of ALK protein can be recited.

As another embodiment of the TGF-β/RhoA pathway inhibitor, for example, an inhibitor of RhoA and an inhibitor of PAK can be recited. Of these, an inhibitor of RhoA is preferable.

A preferable example of the TGF-β pathway inhibitor is an inhibitor that suppresses any one or more of ALK or a cytokine of the TGF-β family that becomes a ligand thereof, and molecules constituting TGF-β/SMAD pathway, TGF-β/Erk pathway, TGF-β/JNK pathway, TGF-β/p38 pathway or TGF-β/RhoA pathway at the downstream of ALK5.

The inhibitor may of course suppress two or more pathways. An inhibitor that suppresses molecules of the TGF-β receptor family, or cytokines of the TGF-β superfamily that becomes a ligand thereof is preferable since it suppresses plural pathways in the TGF-β pathway.

The TGF-β pathway inhibitor is not limited to known TGF-β pathway inhibitors. Any TGF-β pathway inhibitor to be developed from now on is encompassed in the TGF-β pathway inhibitor of the present invention.

The TGF-β pathway inhibitor also encompasses derivatives of the above-mentioned compounds. For example, a derivative of D4476 described in WO 00/61576 can be used.

While "in the presence of a TGF-β pathway inhibitor" mainly means an embodiment in which a TGF-β pathway inhibitor is contained in a medium, it is not limited thereto as long as the effect of the present invention is not impaired. The zo concentration of the TGF-β pathway inhibitor in a medium can be appropriately determined by those of ordinary skill in the art. It is generally about 0.01 μM-100 μM, particularly about 0.1 μM-10 μM.

One kind of the TGF-β pathway inhibitor may be used singly or two or more kinds thereof may be used in combination.

In addition, it can be used in combination with other compound as long as the effect of the present invention is not prevented. For example, a TGF-β pathway inhibitor and a statin compound may be used in combination in view of the high preparation efficiency of the object somatic cell.

The statin compound widely encompasses HMG-CoA reductase inhibitors and is not particularly limited. For example, simvastatin, atorvastatin, lovastatin, fluvastatin, pravastatin, cerivastatin, pitavastatin, rosuvastatin, dihydrocompactin, compactin, bervastatin, carvastatin, crilvastatin, dalvastatin, glenvastatin, fluindostatin, velostatin, mevastatin, rivastatin, cirivastatin, CI-981 and the like can be mentioned. Any statin compound to be developed from now on is encompassed in the statin compound of the present invention.

In a preferable embodiment of the present invention, the number of TGF-β pathway inhibitors and compounds other than the components of the aforementioned medium is not more than 10 kinds, more preferably not more than 4 kinds, further preferably not more than 3 kinds, particularly preferably one or two kinds.

Cultivation

In the method of the present invention, a differentiated somatic cell of a mammal is cultured in an induction medium in the presence of a TGF-β pathway inhibitor.

Cultivation can be performed in an appropriate container for storing cells and media. A method for performing preferable culture is, for example, a culture method under conditions of about 37° C. and carbon dioxide concentration of about 5%, though the method is not limited thereto. Culture under the above-mentioned conditions can be performed using, for example, a known $CO_2$ incubator.

The period of culturing is not particularly limited as long as the effect of the present invention is not impaired. For example, it can be set to for 24 hr to about 60 days, preferably 3-30 days, more preferably about 10-20 days, particularly preferably about 14 days.

The TGF-β pathway inhibitor may be added only in a part of the whole culture period.

In view of the high effect, in the whole culture period, it is possible to adopt culturing in the presence of the above-mentioned compound in an induction medium for a given period (e.g., about 6-10 days, particularly about 8 days) and then culturing in the absence of the above-mentioned compound in an induction medium. In this case, in the whole culture period, culturing in the presence of the above-mentioned compound may be from the start of culturing or after culturing in the absence of the above-mentioned compound for a given period.

Particularly, when brown adipocyte is prepared, it can be efficiently prepared by culturing in an induction medium in the presence of the above-mentioned compound for a given period, for example, about 6-10 days, particularly about 8 days, of the whole culture period from the start of the culturing and thereafter culturing in an induction medium in the absence of the above-mentioned compound.

In addition, differentiated somatic cells of a mammal may be cultured in the presence of a TGF-β pathway inhibitor in a general medium and then cultured in the absence of a TGF-β pathway inhibitor in an induction medium. Alternatively, after culturing in the presence of a TGF-β pathway inhibitor in a general medium, the cells may be cultured in the absence of a TGF-β pathway inhibitor in a general medium and then cultured in the absence of a TGF-β pathway inhibitor in the induction medium. Alternatively, after culturing in the presence of a TGF-β pathway inhibitor in a general medium, the cells may be cultured in the presence of a TGF-β pathway inhibitor in an induction medium and then cultured in the absence of a TGF-β pathway inhibitor in the induction medium. Thus, as long as both processes of culturing in the presence of a TGF-β pathway inhibitor and culturing in an induction medium are included, they may not be performed simultaneously and each may be performed only in a part of the whole culture period.

In culturing, passage can be performed as necessary. When passage is performed, cells are recovered before or immediately after reaching the confluence and seeded in a fresh medium. The medium can also be changed as appropriate in culturing in the present invention.

Even when conversion is not completely finished, the cells during culturing can be recovered and used for transplantation. In this case, the method of the present invention triggers the conversion, and irreversible changes of the epigenome are expected to cause post-transplantation conversion of the cell into the object cell.

In this way, the object somatic cell is prepared.

Preparation of the object somatic cell can be verified by a known method such as marker detection and the like.

An example thereof is described below. Since not all of them can be determined with only one marker, it is desirable to combine detection of several markers for the verification.

It is also possible to evaluate preparation of the object somatic cell by performing comprehensive analysis of mRNA expression such as transcriptome analysis, comprehensive analysis of protein expression such as proteome analysis and the like, of the prepared somatic cells, and comparing with the analysis results of the object somatic cell derived from a living organism.

For example, obtainment of osteoblast can be confirmed by measurement by real-time PCR of mRNA of ALP (alkaline phosphatase) gene, osteocalcin (OC) gene, osteopontin gene and Runx2 gene, staining with Alizarin Red S (production of calcified (mineralized) bone matrix), and the like. In the present specification, preosteoblast, immature osteoblast, mature osteoblast, osteocyte and the like are to be called "osteoblast" altogether.

Obtainment of white adipocyte can be confirmed by unique shape with large unilocular lipid droplet possible staining by Oil Red O staining or Bodipy staining expression of FABP4 gene, HS gene L, AdipoQ gene.

Obtainment of brown adipocyte can be detected by unique shape with multilocular lipid droplets possible staining by Oil Red O staining or Bodipy staining, expression of UCP-1 gene, CIDEA gene, KCNK3 gene, PCG-1α gene, Cox8b gene, Otop gene, ELOVL3 gene and the like. Among others, UCP-1 (Uncoupling protein 1) is a gene specifically expressed in brown adipocytes, encodes mitochondrial inner membrane protein that uncouples oxidative phosphorylation, and is considered to be the basis of the function of brown adipocytes. Thus, it is one of the particularly preferable ones as indices of brown adipocytes.

Obtainment of chondrocyte can be detected by, for example, expression of SOX9 gene, COL2A1 (Type II collgaen) gene, aggrecan gene, COL11A1 (Type XI collgaen) gene, MMP13 gene, production of cartilage matrix, alcian blue staining, toluidine blue staining, Safranine O staining and the like.

Obtainment of myoblast can be detected by, for example, expression of MyoD gene, Myogenin gene, Myf5 gene, MRF4 gene; expression of skeletal muscle type α actin protein, skeletal muscle type myosin protein, morphological features (multiple nuclei, formation of myofiber, formation of myotube), contractibility and the like.

Obtainment of myocardial cell can be detected by, for example, expression of troponin T (cTnT) protein, tropomyosin protein, cardiac muscle type α actin protein, cardiac muscle type myosin protein; expression of ATP2A2 gene, GJA1 gene, GJA5 gene, NPPA gene, NPPB gene, autonomous contractility and the like.

Obtainment of smooth muscle cell can be detected by, for example, expression of α smooth muscle actin (αSMA) protein, smooth muscle myosin protein.

Obtainment of mesenchymal stem cell (MSC) can be detected based on the expression pattern of cell surface antigen by using multiple antibodies, for example, being stained with anti-Stro-1, anti-CD90, anti-CD106, anti-CD105, anti-CD146, anti-CD166, anti-CD44 antibodies and being not stained with anti-CD19, anti-CD45 antibodies and the like. In addition, it can be comprehensively judged by examining expression of MASP1 gene, FOSB gene, and expression of Nestin protein, CXCL12 protein, PDGF receptor α/Sca-1 protein, CD51/PDGF receptor α protein and the like. Furthermore, it can be detected by differentiation potency into various mesenchymal cells.

Obtainment of nerve cell can be detected by, for example, expression of Tuj1 protein, vGLUT1 protein, MAP2 protein, and form, synthesis of neurotransmitter and action potential.

Obtainment of glial cell can be detected by, for example, expression of olig2 protein in the case of oligodendroglia, expression of GFAP protein in the case of astrocyte, and expression of OX42 protein in the case of microglia.

Obtainment of Schwann cell can be detected by, form (morphology of bipolar or multipolar cell with relatively small nuclei, ratio of cell width to cell length), detection of expression of Schwann cell specific markers such as S1001, p75NTR, GFAP, Nestin, NG2 and the like, effect of neurite elongation on cocultured nerve cells and myelin formation ability.

Obtainment of hepatocyte can be detected by, for example, expression of albumin and cytochrome P450, various enzyme activities, metabolism of medicament, functions such as LDL uptake and the like.

Obtainment of biliary epithelial cell can be detected by, for example, characteristic of AFP(−), Dlk(−), Alb(−), CK19 (+), zEpCAM(+), Thy1(−).

Obtainment of vascular endothelial cell can be detected by, for example, expression of CD31 antigen, and expression of Endoglin, VE-cadherin, VWF, TIE2, ANGPT2.

Obtainment of lymphatic endothelial cell can be detected by, for example, expression of D2-40 antigen, and expression of Podoplanin, LYVE-1, PROX-1.

Obtainment of tendon cell can be detected by, for example, expression of Scleraxis (Scx) and tenomodulin (Tnmd).

Fibroblast can be confirmed by gene expression of COL1A1, COL1A2 and the like.

Bone marrow stromal cell can be confirmed by expression of cellular surface marker, gene expression and the like.

Obtainment of lymphocyte, macrophage, granulocyte, hematopoietic stem cell, mast cells and the like can also be confirmed by expression of cellular surface marker, gene expression and the like.

Obtainment of urothelial cell can be detected by, for example, gene expression of Uroplakin1b, Uroplakin2, CK5, CK17, formation of Asymmetric Unit Membrane and the like.

Treatment or Prophylactic Agent; Transplantation Material

The somatic cell generated by the method of the present invention can be used for the prophylaxis or treatment of various disease or condition by transplantation to the body. In this specification, unless otherwise specified, the term "treatment" refers to treatment for a patient suffering from a specific disease or disorder, and means to ameliorate the severity of the disease or disorder, ameliorate one or more symptoms thereof, or delay or reduce the speed of progress of the disease or disorder. In this specification, "treatment" includes "prevention."

The transplantation material refers to a material that introduces a somatic cell into the body. The transplantation material encompasses a material to be transplanted to the same or different individuals after somatic cell preparation in vitro. A transplantation material that induces the target somatic cell until the middle of differentiation in vitro and, after transplantation, finally induces same into a desired somatic cell in vivo after transplantation is also encompassed in the present invention.

Examples of diseases to be treated with osteoblasts include a bone defect due to a bone tumor, trauma, osteomyelitis, etc., or a bone defect after curettage of a bone tumor or the like, bone fracture, osteoporosis, periodontal disease, alveolar bone resorption, cleft lip and palate, rheumatoid arthritis, idiopathic osteonecrosis of the femoral head, arthrosis deformans, lumbar spondylosis deformans, spinal canal stenosis, disc herniation, spondylolysis, spondylolytic spondylolisthesis, scoliosis, cervical spondylotic myelopathy, ossification of posterior longitudinal ligament, spinal cord injury, coxarthrosis, gonarthrosis, slipped capital femoral epiphysis, osteomalacia, reconstruction of fracture sites destroyed by complicated fractures such as mandibular reconstruction, and the like, bone repair after surgery (such as breastbone repair after cardiac surgery), repair of a defect associated with artificial ankle joint surgery, osteomyelitis, and osteonecrosis and the like can be mentioned. Further, when the osteoblasts are transplanted in combination with transplantation of bone, transplantation of artificial bone, and use of artificial joint, or implant, therapeutic effects may be enhanced. Additionally, when bone tissues prepared in vitro by culturing osteoblasts using a three-dimensional scaffold or the like so as to have various shapes are transplanted, the above-mentioned diseases can be treated. In addition to the diseases, various diseases involved in loss, lack, or decreased function of osteoblasts are targeted.

They may be used not only for treatment of a disease, but also for beauty. For example, when the osteoblasts or bone tissue formed by the osteoblasts are transplanted to a defect site associated with an accident, surgery, or the like, the cells can produce a bone matrix to repair the defect site and to make it plump and make it unnoticeable. In such a case, for expediency, dealing of human is also referred to as treatment in this specification, the term "patient" can be replaced by the term "healthy subject" or "human," and the term "disease" can be replaced by the term "beauty."

The osteoblasts can be transplanted to a patient as a cell preparation, can be transplanted together with a base (scaffold) formed of an artificial material, such as hydroxyapatite or bioabsorbable ceramic, or can be cultured with a scaffold, and then transplanted. In such case, the scaffold may form various three-dimensional shapes according to the purpose of transplantation.

Also, the brown adipocyte can be used for the prophylaxis or treatment of obesity, metabolic syndrome or disease or condition related to these. The target disease includes Type I diabetes, Type II diabetes, diabetic complications (retinopathy, peripheral neurosis, nephropathy, macroangiopathy, diabetic gangrene, osteoporosis, diabetic coma etc.), impaired glucose tolerance, insulin resistance, acidosis, ketosis, ketoacidosis, obesity, central obesity and complications thereof, visceral obesity syndrome, hypertension, postprandial dyslipidemia, cerebrovascular diseases, arteriosclerosis, atherosclerosis, metabolic-syndrome, dyslipidemia, hypertriglyceridemia, hypercholesterolemia, hypoHDL-emia, renal disease (diabetic nephropathy, nephrotic syndrome etc.), arteriosclerosis, thrombotic disease, myocardial infarction, ischemic cardiac diseases, angina pectoris, cardiac failure, cerebrovascular diseases (cerebral infarction, cerebral apoplexy etc.), peripheral blood circulation disorder, perception disorder, hyperuricemia, gout, infections (respiratory infection, urinary tract infection, gastrointestinal infections, skin infections, soft tissue infections etc.), malignant tumor, cataract, fatty liver, non-alcoholic steatohepatitis and osteoporosis. Prophylactic or treatment effects on these diseases are considered to be obtained due to lipid burning and improvement of sugar and lipid metabolic abnormality by brown adipocytes.

In addition, brown adipocytes can also be used for cosmetic application to remove fat around the abdomen and jaw, of the thigh and the like. Brown adipocytes can also be used as a transplantation material to be introduced into breast and the like for cosmetic applications.

When brown adipocytes are administered, fat content, particularly white adipocytes such as visceral fat, subcutaneous fat and the like decrease, and the body weight increase when a high-calorie food is ingested is suppressed. Therefore, brown adipocytes are useful for both the prophylaxis and treatment of obesity, metabolic syndrome or disease or condition related to these. The present invention can also be used not only for the prophylaxis or treatment of diseases but also health promotion and beauty (e.g., removal of visceral fat and subcutaneous fat in abdomen, jaw, arm, thigh and the like) and the like. In this case, dealing of human is conveniently referred to as treatment in the present specification, and "patient" can mean "healthy human" or "human" and "disease" can mean "health promotion", "beauty" and the like.

Brown adipocytes can also be used as a transplantation material to be introduced into breast and the like for cosmetic applications.

White adipocyte can improve tissue morphology and prevent infection by transplanting white adipocytes to the defective part of the tissue due to trauma, burn, surgery or the like. For example, by transplanting white adipocytes into the defect part after excisional surgery of breast cancer, breast can be rebuilt. It can also be used as a transplantation material for cosmetic applications.

Myoblast is considered to afford a prophylactic or therapeutic effect for myotonia syndromes such as Duchenne muscular dystrophy, muscular dystrophy, congenital/distal myopathy, myotonic dystrophy and the like, myogenic diseases such as mitochondria disease, periodic paralysis and the like, neurogenic muscle diseases such as Werdnig-Hoffman disease, Charcot-Marie-Tooth disease, congenital hypomyelination, amyotrophic lateral sclerosis (ALS) and the like, collagen diseases such as dermatomyositis, polymyositis, polyarteritis nodosa, polymyalgia rheumatica, mixed connective tissue disease and the like, inflammatory myopathy, endocrine myopathy, drug-induced myopathy by steroid, therapeutic drug for hyperlipidemia and the like, sarcopenia, fibrodysplasia ossificans progressiva (FOP) and the like.

Chondrocyte is considered to afford a prophylactic or therapeutic effect for cartilage injury, cartilage defect and the like seen in cartilage disease such as osteoarthritis, osteochondrosis deformans, chondrodystrophy arthritis, rheumatoid arthritis, trauma, injury of intervertebral disk, meniscus injury, osteochondritis dissecans, bone necrosis, neurogenic arthropathy and the like.

Mesenchymal stem cell is considered to afford a prophylactic or therapeutic effect for the above-mentioned many diseases and the like for which osteoblast, adipocyte, chondrocyte, myoblast and the like that can be differentiated from mesenchymal stem cells are effective.

Tendon cell is considered to afford a prophylactic or therapeutic effect for tendon rupture and the like associated with trauma or surgery.

Nerve cell and glial cell are considered to afford a prophylactic or therapeutic effect for neurodegenerative disease (Parkinson's disease, parkinson's syndrome, Alzheimer's disease, amyotrophic lateral sclerosis, progressive supranuclear paralysis, Huntington's disease, Shy-Dragersyndrome, striatonigral denaturation, olivopontoserebellar atrophy, spinocerebellar ataxia and the like), corticobasal degeneration, Lewy body disease, dystonia, Meige's syndrome, late cerebellar cortical atrophy, familial spastic paraplegia, motor neurone disease, Machado-Joseph disease, Pick disease, cerebral apoplexy, cerebrovascular diseases, demyelination disease (multiple sclerosis, Guillain-Barre syndrome, acute disseminated encephalomyelitis, acute cerebellitis, transverse myelitis and the like), brain tumor, cerebrospinal diseases associated with infection (meningitis, brain abscess, Creutzfeldt-Jakob disease and the like), neurological dysfunction after trauma, neuropathy due to toxin, radiation and the like, psychiatric diseases (schizophrenia, manic depression and the like), sleep disorder (narcolepsy, primary hypersomnia, recurrent hypersomnia, idiopathic hypersomnia, insomnia and the like), epilepsy and the like.

Examples of the diseases to be treated with Schwann cell include loss or damage of the central nerve due to cerebral infarction, spinal injury and the like, loss or damage of the peripheral nerve due to trauma, neuritis or tumor resection and the like; diseases of the central nervous system such as multiple sclerosis optic nervemyelitis (Devic syndrome), concentric sclerosis (Balo disease), acute disseminated encephalomyelitis (ADEM), inflammatory diffuse sclerosis (Schilder disease), infectious subacute sclerosing panencephalitis (subacute sclerosing panencephalitis, SSPE), progressive multifocal leukoencephalopathy (PML) and the like; diseases of the peripheral nervous system such as Guillain-Barre syndrome, Fisher syndrome, chronic inflammatory demyelinating polyneuropathy and the like; diseases based on deficiency, insufficiency or functional decrease of Schwann cell and the like.

Hepatocyte and biliary epithelial cell are considered to afford a prophylactic or therapeutic effect for liver failure, fulminant hepatitis, cirrhosis, steatohepatitis, metabolic syndrome and the like. They can also be useful in toxicity test, metabolism test and safety test of a drug for the liver. They are also useful for screening and judgment of effect of a drug for diabetes, dyslipidemia, metabolic syndrome, hypertension and the like.

The cells of the lung and airway are considered to afford a prophylactic or therapeutic effect for primary pulmonary hypertension, lung fibrosis, emphysema, bronchiectasis, pulmonary sarcoidosis, interstitial pneumonia, cystic fibrosis, diffuse panbronchiolitis, obstructive panbronchiolitis, pulmonary eosinophilic granuloma disease, chronic thromboembolic pulmonary hypertension, multiple pulmonary arteriovenous fistula and the like.

Kidney cell is considered to afford a prophylactic or therapeutic effect for renal failure, diabetic nephropathy, chronic glomerulonephritis, congenital renal hypoplasia, cystic kidney, IgA nephropathy, nephrosclerosis, gestational toxicosis and the like.

Urothelial cell is useful for formation of surrogate bladder in the case of total removal of bladder in bladder cancer, construction of a patch to a site where the urothelium is defective in vesicovaginal fistula, formation of urothelium for partial compensation in bladder enlargement surgery in the case of neurogenic bladder with fibrotic and atrophied bladder, regeneration of urothelium for advanced interstitial cystitis (dysfunction of urothelium) and the like.

Myocardial cell is considered to afford a prophylactic or therapeutic effect for myocardial infarction, ischemic cardiac diseases, congestive heart failure, myocarditis, hypertrophic cardiomyopathy, dilated cardiomyopathy and the like.

Lymphatic endothelium is considered to afford a prophylactic or therapeutic effect for lymphatic edema and the like.

Smooth muscle cell is useful for regenerative treatment of airway, gastrointestinal tract and blood vessel.

Vascular endothelial cell is useful for regenerative treatment of blood vessel.

Hematopoietic stem cell and bone marrow stromal cell are useful for bone marrow failure, aplastic anemia and immunodeficiency.

Lymphocyte, granulocyte, macrophage and dendritic cell are useful for immunodeficiency disease and antitumor immunity. Megakaryocyte is useful for thrombocytopenia. Erythroblast is useful for aplastic anemia.

The present invention can also be used for the treatment of diseases in not only human but also pet animals such as dog, cat and the like and domestic animals such as bovine, horse, swine, sheep, chicken and the like. In this case, "patients" and "human" are respectively referred to as "animal patient" and "animal".

The present invention can also be used not only for regenerative medicine but also development of medicaments (including biological preparation and nucleic acid medicament) for various diseases, evaluation of side effects of medicament, basic researches for elucidation of development and pathology and the like.

Inducer

The present invention also provides an inducer containing a TGF-β pathway inhibitor for converting differentiated somatic cell to other somatic cell. In addition, it also provides use of a TGF-β pathway inhibitor for converting differentiated somatic cell to other somatic cell.

That is, the present invention provides novel use of a TGF-β pathway inhibitor.

The inducer may be a TGF-β pathway inhibitor alone or a composition containing a TGF-β pathway inhibitor. When it is a composition, the composition may further contain an appropriate solvent (water, DMSO and the like) for dissolving the TGF-β pathway inhibitor.

EXAMPLES

While Examples are shown in the following, the present invention is not limited to the Examples alone.

The structures of the compounds used in the Examples are shown below.

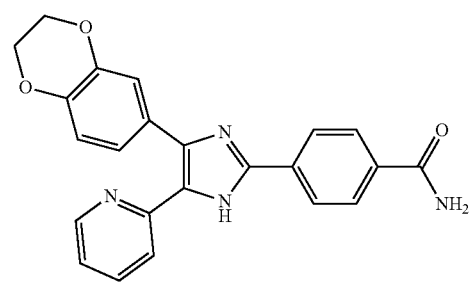

D4476

-continued
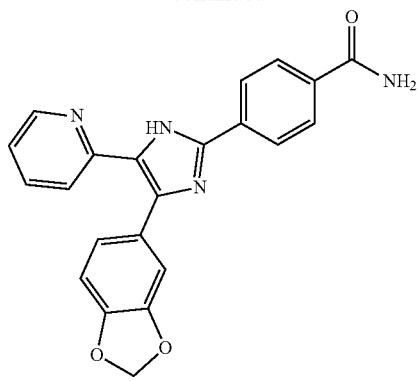
SB431542
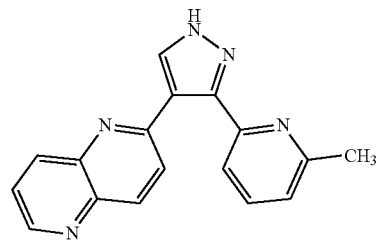
ALK5 Inhibitor II
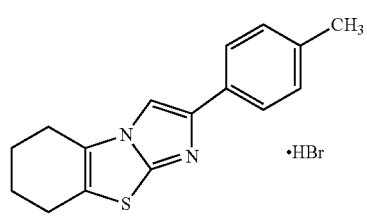
Cyclic Pifithrin-α hydrobromide
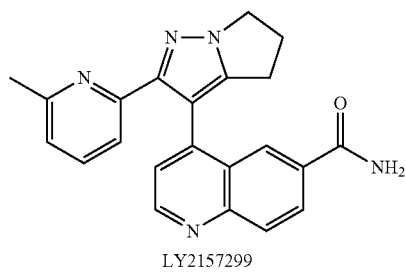
LY2157299
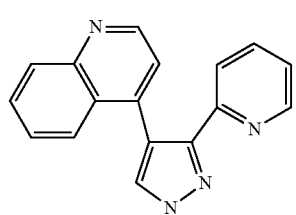
LY364947
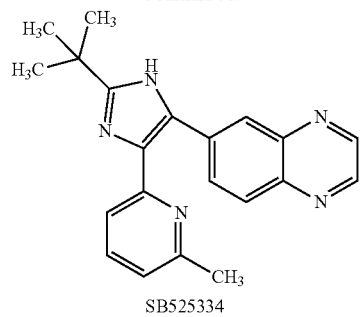
SB525334
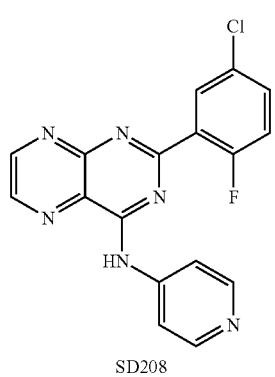
SD208
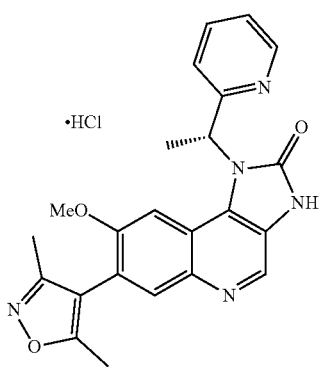
I-BET
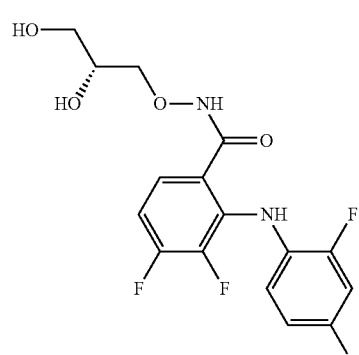
PD0325901

-continued

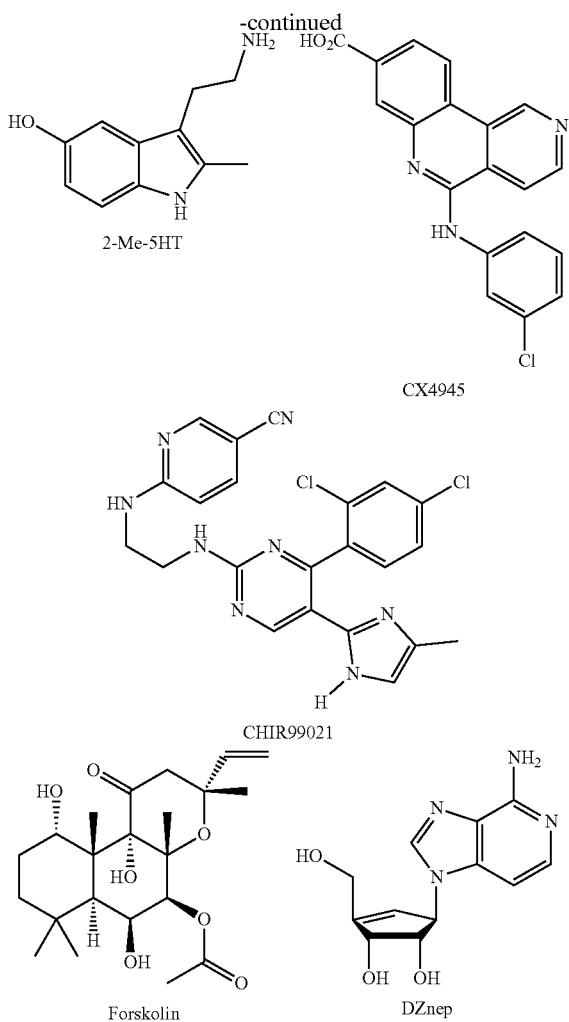

2-Me-5HT

CX4945

CHIR99021

Forskolin

DZnep

In the present specification and drawings below, "ALK5 Inhibitor II" is sometimes indicated as "ALK5 Inhibitor", "ALK5IH", "ALK5 IHII" or "ALK5i II".

Example 1 (FIG. 1)

Human normal skin-derived fibroblasts (human dermal fibroblasts; HDFs) were suspended in a general medium (Dulbecco's modified minimum essential medium; DMEM added with 10% FBS). This was seeded in a 24-well plate at a concentration of $5 \times 10^3$ cells/well (day 0), and culturing was started in 5% $CO_2$/95% humidified air at 37° C. The next day, the culture supernatant was removed by suction and, as described in the Figure, the general medium, a calcification induction medium, or a calcification induction medium added with each compound was added at 500 µL/well.

The calcification induction medium is a 10% FBS DMEM added with 50 µg/ml ascorbic acid, 10 mM β-glycerophosphate and 100 nM Dexamethasone. The culture medium was exchanged with a fresh one every 3-4 days and culturing was continued until day 24.

On day 24, the culture medium was removed from each well by suction, washed with PBS(-), and fixed with 10% formalin. It was washed 3 times with sterile distilled water. Thereafter, Alizarin Red S staining solution was added, and the mixture was incubated at room temperature for 15 min. The well after staining was washed with sterile distilled water and photographed.

The concentrations of the compounds are as follows:
D4476: 2 µM
ALK5 inhibitor II: 2 µM
SB431542: 2 µM.

The results are shown in FIG. 1. It was clarified that human fibroblast was converted to osteoblast having calcified is bone matrix production ability by culturing in an induction medium added with D4476, ALK5 inhibitor II or SB431542. Particularly, it is clear that ALK5 inhibitor II most efficiently converts fibroblast to osteoblast.

As for TGF-β signal, it is known to be essential for the proliferation, survival and differentiation and osteogenesis of osteoblasts, and promotes differentiation and osteogenesis of osteoblasts (e.g., document: Kasagi and Chen, Cell & Bioscience 2013, 3:4). It was an unexpected result that by the method of the present invention, conversion to osteoblasts can be achieved by suppression of TGF-β pathway.

Figure 2:
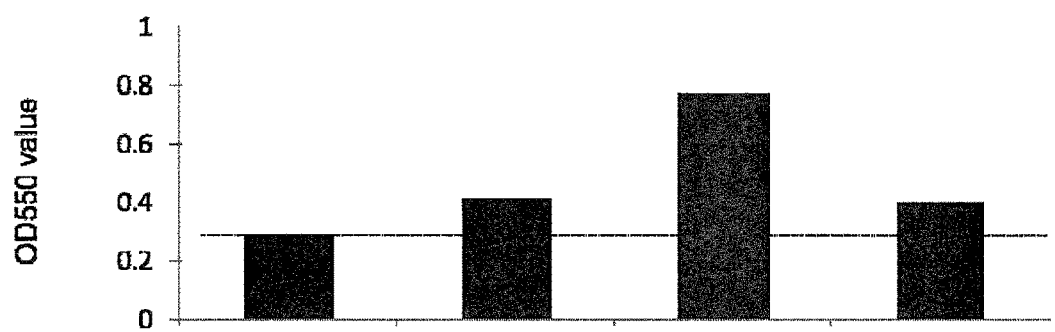
FIG. 2 shows the results of Alizarin Red S staining (absorbance measurement).

Example 2 (FIG. 2)

Human normal skin-derived fibroblasts (human dermal fibroblasts; HDFs) were suspended in a general medium (Dulbecco's modified minimum essential medium; DMEM added with 10% FBS). This was seeded in a 24-well plate at a concentration of $5 \times 10^3$ cells/well (day 0), and culturing was started in 5% $CO_2$/95% humidified air at 37° C. The next day, the culture supernatant was removed by suction and, as described in the Figure, a calcification induction medium or a calcification induction medium added with each compound was added at 500 µL/well.

The calcification induction medium is a 10% FBS DMEM added with 50 g/ml ascorbic acid, 10 mM β-glycerophosphate and 100 nM Dexamethasone. The culture medium was exchanged with a fresh one every 3-4 days and culturing was continued until day 24.

On day 24, the culture medium was removed from each well by suction, washed with PBS(-), and fixed with 10% formalin. It was washed 3 times with sterile distilled water and Alizarin Red S staining solution was added, and the mixture was incubated at room temperature for 15 min. The staining solution after staining was recovered in a 96 well plate and the absorbance (OD: 550 nm) was measured by an absorption spectrometer.

The concentrations of the compounds are as follows:
D4476: 2 µM
SB431542: 2 µM
ALK5 inhibitor II: 2 µM.

The results are shown in FIG. 2. By culturing in an induction medium added with D4476, ALK5 inhibitor II or SB431542, it is clear that human fibroblast was converted to osteoblast having calcified bone matrix production ability. Particularly, it is clear that ALK5 inhibitor II most efficiently converts fibroblast to osteoblast.

Figure 3:
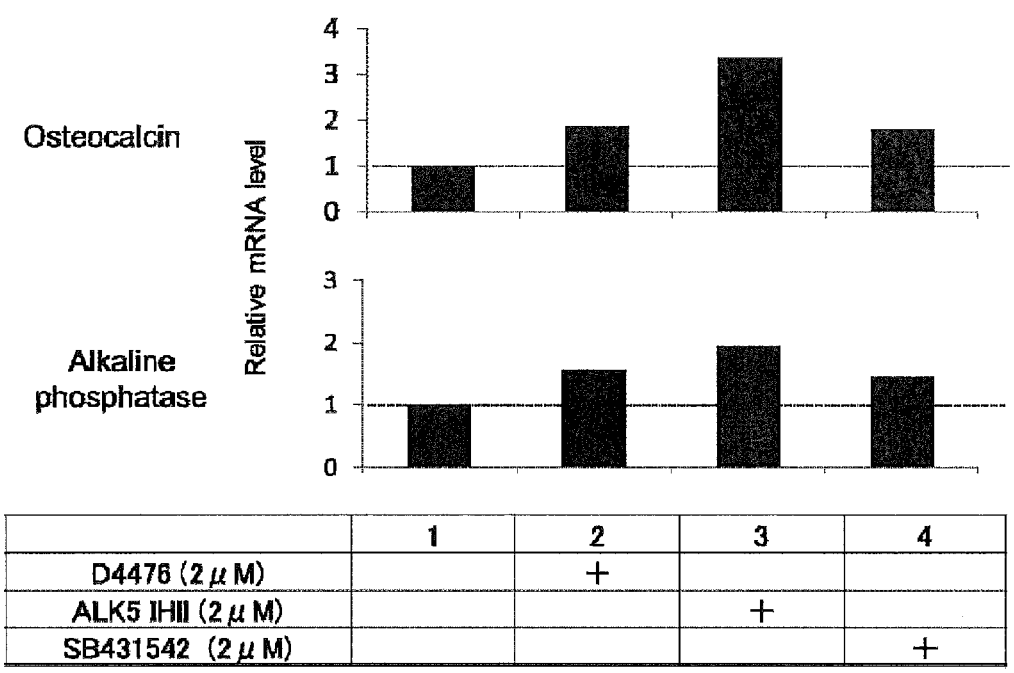
FIG. 3 shows the measurement results of a gene expression level by a real-time RT-PCR method.

Example 3 (FIG. 3)

Human normal skin-derived fibroblasts (human dermal fibroblasts; HDFs) were suspended in a general medium (Dulbecco's modified minimum essential medium; DMEM added with 10% FBS). This was seeded in a 24-well plate at a concentration of $5 \times 10^3$ cells/well (day 0), and culturing was started in 5% $CO_2$/95% humidified air at 37° C. The next day, the culture supernatant was removed by suction and, as described in the Figure, a calcification induction medium, or a calcification induction medium added with each compound was added at 500 µL/well.

The calcification induction medium is a 10% FBS DMEM added with 50 g/ml ascorbic acid, 10 mM β-glycerophosphate and 100 nM Dexamethasone. The culture medium was exchanged with a fresh one every 3-4 days and culturing was continued until day 24.

On day 24, the culture medium was removed from each well by suction, washed with PBS, and total RNA was extracted from the cell with ISOGEN II. cDNA was synthesized from the RNA by using Rever Tra Ace qPCR RT Master Mix. This cDNA was admixed with Real-time PCR Master Mix, primers specific to Osteocalcin and Alkaline Phosphatase or β-actin gene and Taqman probe. qRT-PCR was performed using AB7300 Real-time PCR system. The mRNA level of Osteocalcin and Alkaline Phosphatase gene was quantified as a ratio to β-actin gene mRNA, and calculated with the value of fibroblast cultured in a calcification induction medium alone as 1.

The concentrations of the compounds are as follows:
D4476: 2 µM
SB431542: 2 µM
ALK5 inhibitor II: 2 µM.

The results are shown in FIG. 3. By culturing in an induction medium added with D4476, ALK5 inhibitor II or SB431542, it is clear that human fibroblast was converted to osteoblast expressing osteocalcin and alkaline phosphatase gene. Particularly, it is clear that ALK5 inhibitor II most efficiently converts fibroblast to osteoblast.

Figure 4:
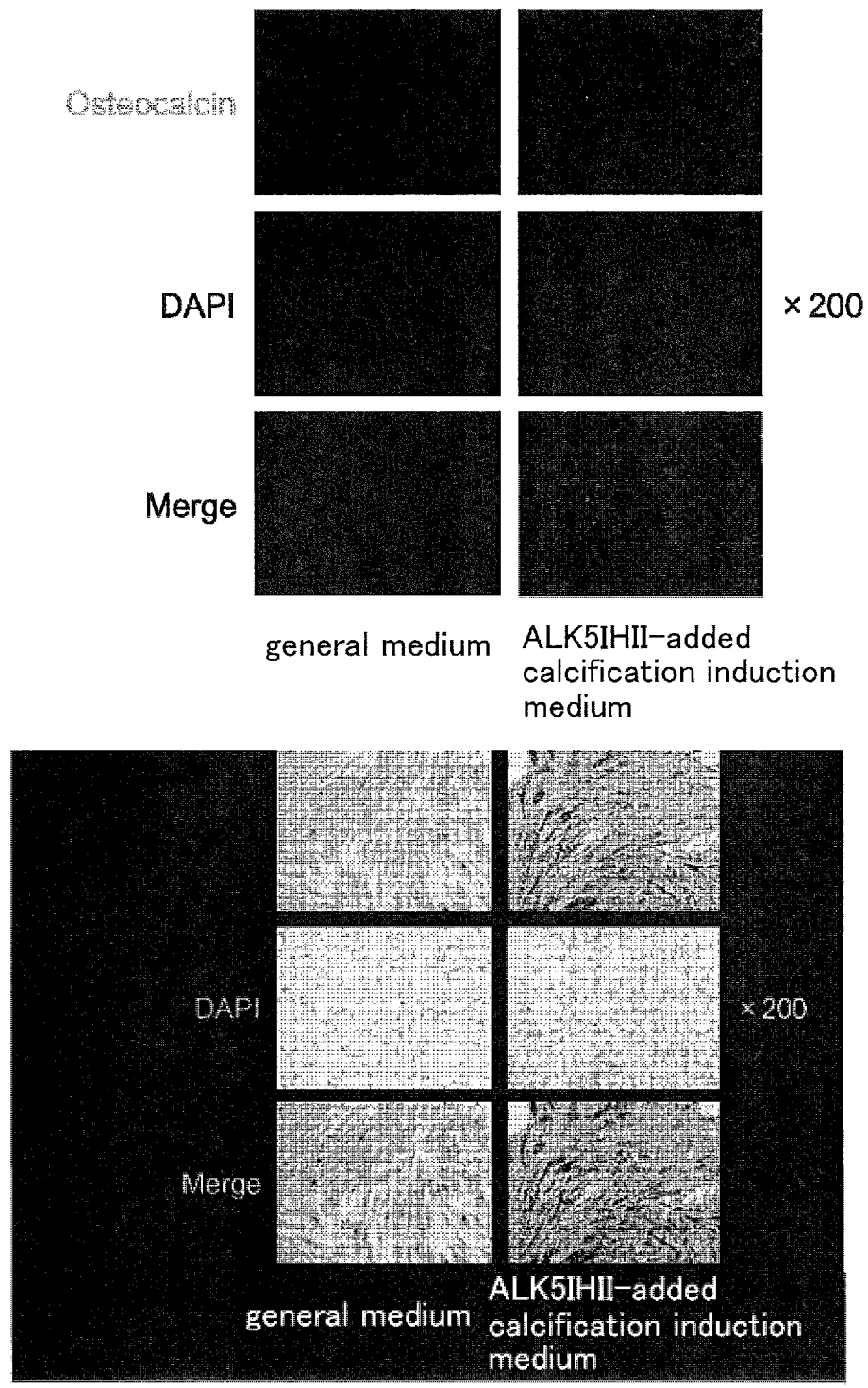
FIG. 4 shows the results of immunostaining of Osteocalsin (staining Figure).

Example 4 (FIG. 4)

Human normal skin-derived fibroblasts (human dermal fibroblasts; HDFs) were suspended in a general medium (Dulbecco's modified minimum essential medium; DMEM added with 10% FBS). This was seeded in a 24-well plate at a concentration of $5 \times 10^3$ cells/well (day 0), and culturing was started in 5% $CO_2$/95% humidified air at 37° C. The next day, the culture supernatant was removed by suction, and the general medium or a calcification induction medium added with an ALK5 inhibitor II was added at 500 µL/well.

The calcification induction medium is a 10% FBS DMEM added with 50 µg/ml ascorbic acid, 10 mM β-glycerophosphate and 100 nM Dexamethasone. The culture medium was exchanged with a fresh one every 3-4 days and culturing was continued until day 24.

On day 24, the culture medium was removed from each well by suction, and the cells were washed with PBS(-). After fixing with 4% para-formaldehyde, the cells were washed with PBS(-). After washing 3 times with PBS(-), Blocking One was added, and the mixture was incubated at room temperature for 60 min.

Anti-Osteocalcin antibody was added and the mixture was reacted at 4° C. overnight, and washed 3 times with Wash buffer. Alexa 488-conjugated anti-mouse Ig antibody was added and the mixture was reacted at room temperature for 1 hr, and the mixture was washed 5 times with Wash buffer. Using a fluorescence microscope, the cells were photographed at ×200 magnification.

The results are shown in FIG. 4. It is clear that culturing in an induction medium added with an ALK5 inhibitor II converted human fibroblast to osteoblast producing osteocalcin.

Figure 5:
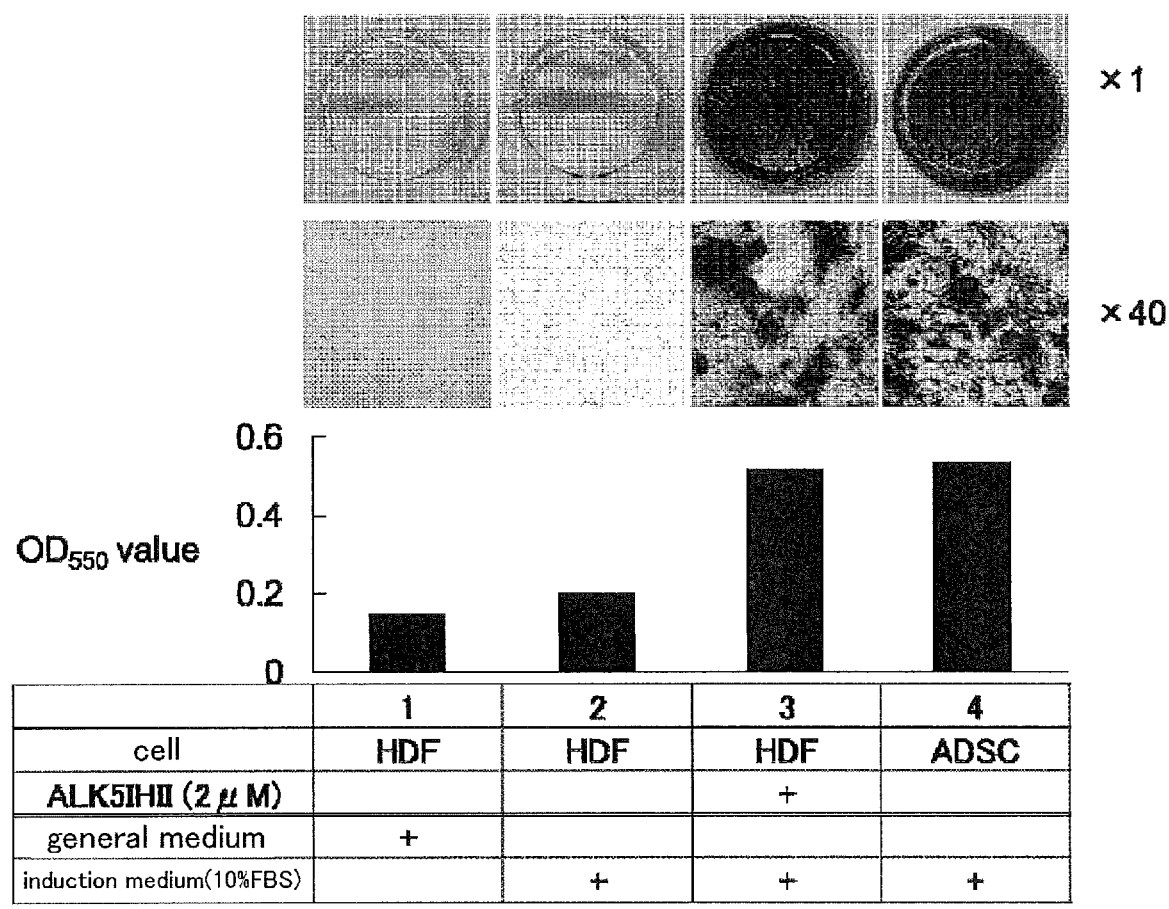
FIG. 5 shows the results of Alizarin Red S staining (staining Figure and absorbance measurement).

Example 5 (FIG. 5)

Human normal skin-derived fibroblasts (human dermal fibroblasts; HDFs) or human fat-derived mesenchymal stem cells (human adipose derived stem cells; ADSC) were suspended in the general medium (Dulbecco's modified minimum essential medium; DMEM added with 10% FBS). This was seeded in a 24-well plate at a concentration of $5 \times 10^3$ cells/well (day 0), and culturing was started in 5% $CO_2$/95% humidified air at 37° C. The next day, the culture supernatant was removed by suction and, as described in the Figure, the general medium, calcification induction medium or a calcification induction medium added with ALK5 inhibitor II was added at 500 µL/well.

The calcification induction medium is 10% FBS DMEM added with 50 µg/ml ascorbic acid, 10 mM β-glycerophosphate and 100 nM Dexamethasone. The culture medium was exchanged with a fresh one every 3-4 days, and culturing was performed until day 19.

On day 19, the culture medium was removed from each well by suction, washed with PBS(-), and fixed with 10% formalin. It was washed 3 times with sterile distilled water. Thereafter, Alizarin Red S staining solution was added, and the mixture was incubated at room temperature for 15 min. The staining solution after staining was recovered in a 96 well plate, and the absorbance at 550 nm ($OD_{550}$) was measured by an absorption spectrometer (FIG. 5, lower). The well after staining was washed with sterile distilled water, and photographed with an inverted microscope at ×1 magnification and ×40 magnification (FIG. 5, top).

The results are shown in FIG. 5. It is clear that culturing in an induction medium added with an ALK5 inhibitor II converted human fibroblast and fat-derived mesenchymal stem cell to converted to osteoblast having calcified bone matrix production ability.

Example 6 (FIG. 6)

Human normal skin-derived fibroblasts (human dermal fibroblasts; HDFs) were suspended in a general medium (Dulbecco's modified minimum essential medium; DMEM added with 10% FBS). This was seeded in a 24-well plate at a concentration of $5 \times 10^3$ cells/well (day 0), and culturing was started in 5% $CO_2$/95% humidified air at 37° C. The next day, the culture supernatant was removed by suction, and the general medium or a calcification induction medium added with ALK5 inhibitor II was added at 500 µL/well.

The calcification induction medium is a 10% FBS DMEM added with 50 µg/ml ascorbic acid, 10 mM β-glycerophosphate and 100 nM Dexamethasone. The culture medium was exchanged with a fresh one every 3-4 days and culturing was continued until day 24.

On day 19, the culture medium was removed from each well by suction, and the cells were washed with PBS(-). After fixing with 4% para-formaldehyde, the cells were washed with PBS(-). After washing 3 times with PBS(-), Blocking One was added, and the mixture was incubated at room temperature for 60 min.

Anti-Runx2 antibody was added and the mixture was reacted at 4° C. overnight and washed 3 times with Wash buffer. Alexa 488-conjugated anti-mouse Ig antibody was added and the mixture was reacted at room temperature for 1 hr, and washed 5 times with Wash buffer. Using a fluorescence microscope, the cells were photographed at ×200 magnification.

The cells cultured in the general medium are shown as HDF, and the cells cultured in the calcification induction medium added with ALK5 inhibitor II are shown as dOBs in the Figure.

The results are shown in FIG. 6. It is clear that culturing in an induction medium added with an ALK5 inhibitor II converted human fibroblast to osteoblast expressing Runx2.

Figure 7:
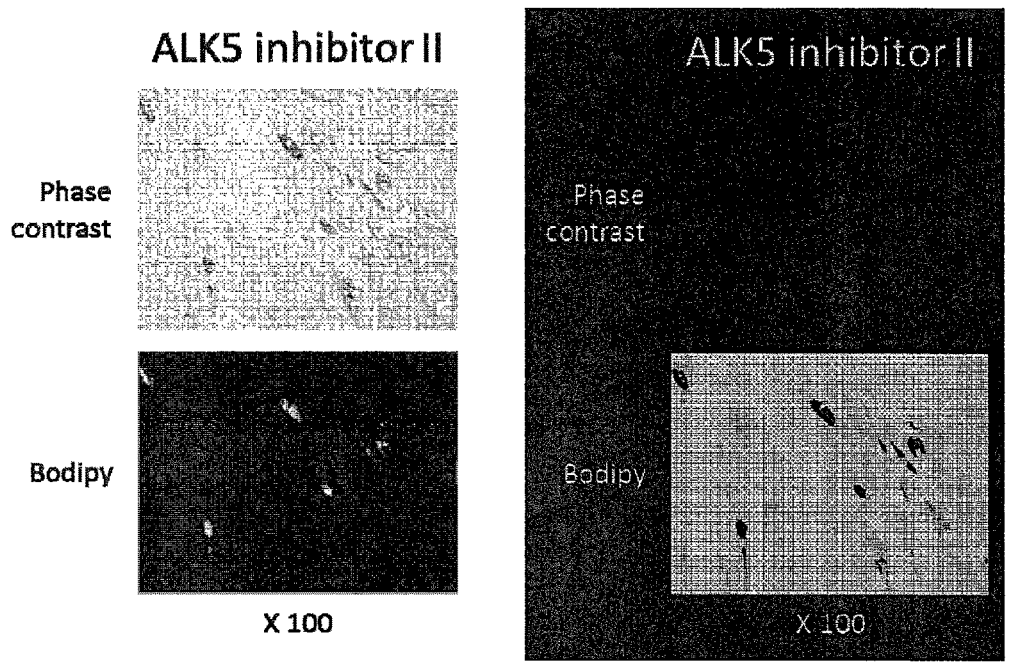
FIG. 7 shows the results of Bodipy staining (staining Figure).

Example 7 (FIG. 7)

Human normal skin-derived fibroblasts (human dermal fibroblasts; HDFs) were suspended in a general medium (Dulbecco's modified minimum essential medium; DMEM added with 10% FBS). This was seeded in a 24-well plate at a concentration of $10 \times 10^3$ cells/well (day 0), and culturing was started in 5% $CO_2$/95% humidified air at 37° C. On day 4, the culture supernatant was removed by suction, induction medium (a) added with 50 mM ALK5 Inhibitor II (below) was added and the mixture was cultured. On day 6, induction medium (a) was removed, an induction medium (b) added with 50 mM ALK5 Inhibitor II (below) was added and culturing was continued. Thereafter, on days 9, 12, 14, 16, using the induction medium (b) added with 50 mM ALK5 Inhibitor II, medium exchange was repeated similarly.

On day 20, the culture medium was removed by suction, and the well was washed with PBS(−), and fixed with 10% formalin. It was washed 3 times with sterile distilled water. After staining with Bodipy, the well was washed with sterile distilled water, and photographed with an inverted microscope at ×100, ×200 magnifications.

The results are shown in FIG. 7. White adipocytes containing large unilocular lipid droplets were found in Phase contrast and fluorescence image, and it is clear that human normal skin-derived fibroblasts were converted to white adipocytes.

The compositions of the induction media (a) and (b) are as follows:

[induction medium (a)]
DMEM (High Glucose): 500 mL
FETAL BOVINE SERUM (FBS): 50 mL
MEM Non-Essential Amino Acids Solution: 5 mL 100 mM-Sodium
Pyruvate Solution: 5 mL
Penicillin-Streptomycin Mixed Solution: 5 mL Insulin: 170 nM
3,3',5-Triiodo-L-thyronine: 1 nM
Rosiglitazone: 1 uM
IBMX (3-isobutyl-1-methylxanthine): 0.5 mM Indomethacin: 62.5 mM
Dexamethasone: 1 uM
[induction medium (b)]
DMEM (High Glucose): 500 mL
FOETAL BOVINE SERUM (FBS): 50 mL
MEM Non-Essential Amino Acids Solution: 5 mL 100 mM-Sodium
Pyruvate Solution: 5 mL
Penicillin-Streptomycin Mixed Solution: 5 mL Insulin: 170 nM
3,3',5-Triiodo-L-thyronine: 1 nM.

Figure 8:
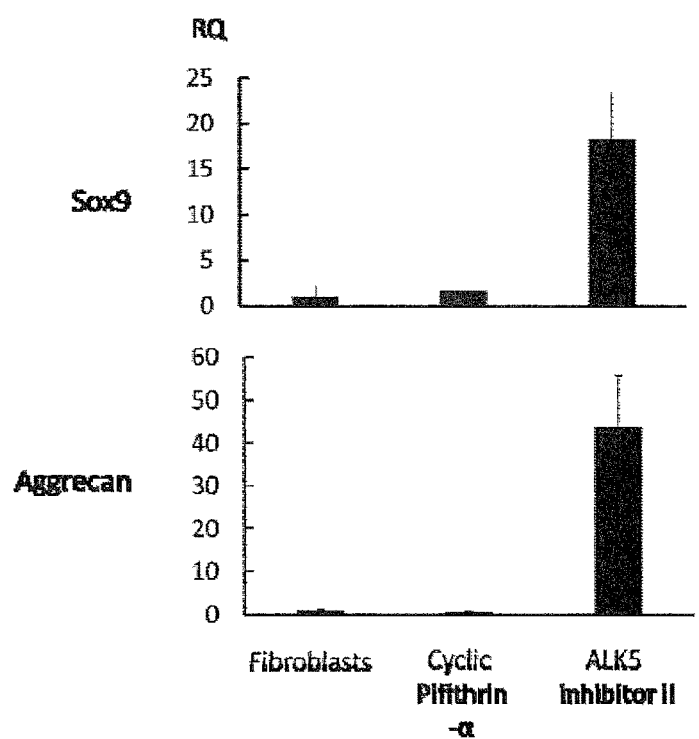
FIG. 8 shows the measurement results of a gene expression level by a real-time RT-PCR method.

Example 8 (FIG. 8)

Human normal skin-derived fibroblasts (human dermal fibroblasts; HDFs) were suspended in a general medium (Dulbecco's modified minimum essential medium; DMEM added with 10% FBS). This was seeded in a 12-well plate at a concentration of $2 \times 10^4$ cells/well (day 0), and culturing was started in 5% $CO_2$/95% humidified air at 37° C. The next day, the culture supernatant was removed by suction, and a cartilage induction medium (StemPro Chondrogenesis Differentiation Kit: manufactured by ThermoFisher Scientific) added with Cyclic Pifithrin-α or ALK5 inhibitor II was added at 1000 µL/well.

Once every 2 days, the culture medium was exchanged with a fresh one, and culturing was performed until day 18.

On day 18, the culture medium was removed from each well by suction, washed with PBS, and total RNA was extracted from the cell with ISOGEN II. cDNA was synthesized from the RNA by using Rever Tra Ace qPCR RT Master Mix. This cDNA was admixed with Real-time PCR Master Mix, primers specific to Sox9 and Aggrican or β-actin gene and Taqman probe. qRT-PCR was performed using AB7300 Real-time PCR system. The mRNA level of Sox9 and Aggrican gene was quantified as a ratio to β-actin gene mRNA, and calculated with the value of fibroblast cultured in the general medium as 1.

The concentrations of the compounds are as follows:
Cyclic Pifithrin-α: 5 µM
ALK5 inhibitor II: 2 µM.

The results are shown in FIG. 8. It could be confirmed that culturing in a cartilage induction medium in the presence of ALK5 inhibitor II can convert human normal skin-derived fibroblast to chondrocyte expressing Sox9 and Aggrican gene. Cyclic Pifithrin-α is known to promote reprogramming of fibroblast to iPS cell. However, it is clear that Cyclic Pifithrin-α does not promote conversion of fibroblast to chondrocyte.

It is known that TGF-β receptor signal via activin positively controls MSC proliferation, and TGF-β receptor signal promotes differentiation from MSC to osteoblast and chondrocyte (e.g., document: W. G. Li and X. X. Xu, Chin J Traumatol. 2005; 8(6):349-51, document: F. Ng et al., Blood. 2008; 112(2):295-307). It was an unexpected result that by the method of the present invention, conversion to chondrocyte can be achieved by suppression of TGF-β pathway.

Figure 9:
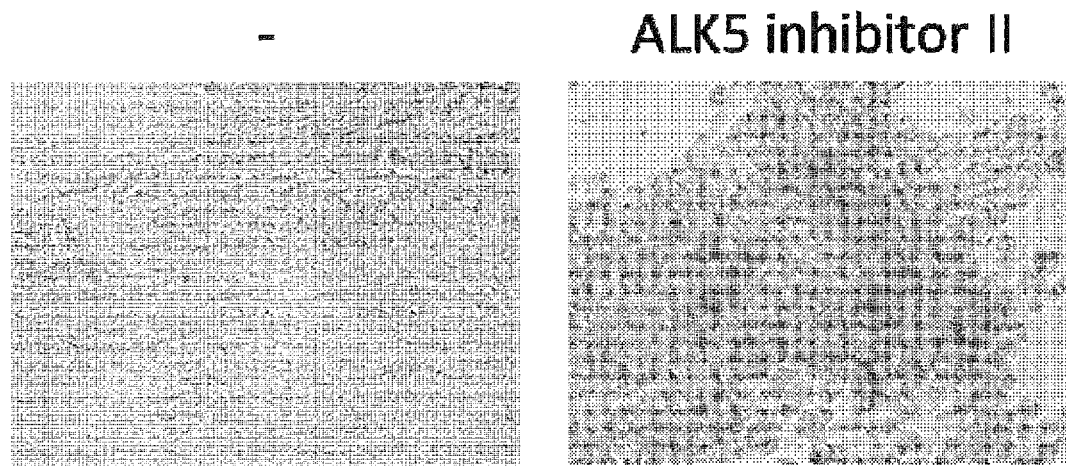
FIG. 9 shows the results of alcian blue staining (staining Figure).

Example 9 (FIG. 9)

Human normal skin-derived fibroblasts (human dermal fibroblasts; HDFs) were suspended in a general medium (Dulbecco's modified minimum essential medium; DMEM added with 10% FBS). This was seeded in a 12-well plate at a concentration of $2 \times 10^4$ cells/well (day 0), and culturing was started in 5% $CO_2$/95% humidified air at 37° C. The next day, the culture supernatant was removed by suction, and a cartilage induction medium or a cartilage induction medium added with 2 M ALK5 inhibitor II was added at 1000 µL/well.

Once every 2 days, the culture medium was exchanged with a fresh one, and culturing was performed until day 18. The cells were washed twice with PBS(−), once with 3% acetic acid solution, an alcian blue staining solution (PH2.5) (Nacalai Tesque) was added and the cells were stained for 1 hr at room temperature. The cells were washed 3 times with PBS(−) and observed under a microscope.

The results are shown in FIG. 9. It could be confirmed that culturing in a cartilage induction medium in the presence of ALK5 inhibitor II can convert human normal skin-derived fibroblast to cartilage that produces cartilage matrix stained blue.

Figure 10:
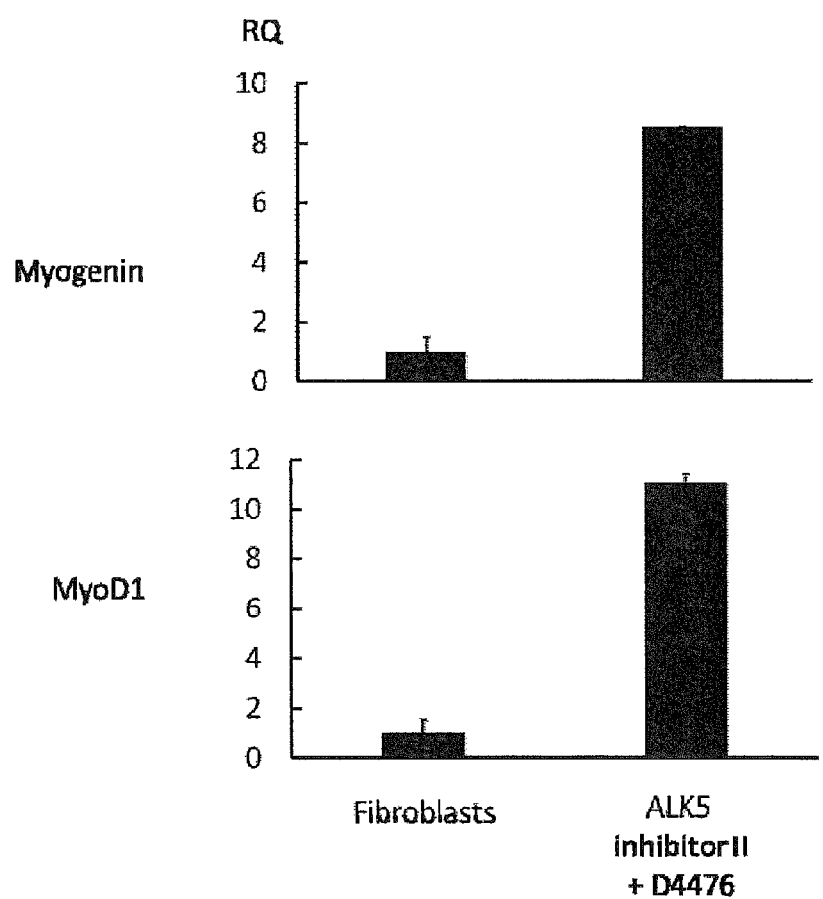
FIG. 10 shows the measurement results of a gene expression level by a real-time RT-PCR method.

Example 10 (FIG. 10)

Human normal skin-derived fibroblasts (human dermal fibroblasts; HDFs) were suspended in a general medium (Dulbecco's modified minimum essential medium; DMEM added with 10% FBS). This was seeded in a 12-well plate at a concentration of 2×10⁴ cells/well (day 0), and culturing was started in 5% $CO_2$/95% humidified air at 37° C. The next day, the culture supernatant was removed by suction, a skeleton muscle cell growth medium added with 2 μM ALK5 inhibitor II and 2 μM D4476 (Ham's/F10 medium added with 5% FBS, 50 microG/ml Bovine Fetuin, 10 nG/ml hEGF, 1 nG/ml bFGF, 10 microG/ml Insulin, 0.4 microG Dexamethasone) was added at 1000 μL/well. Once every 2 days, the culture medium was exchanged with a fresh one, and culturing was performed until day 28.

On day 28, the culture medium was removed from each well by suction, washed with PBS, and total RNA was extracted from the cell with ISOGEN II. cDNA was synthesized from the RNA by using Rever Tra Ace qPCR RT Master Mix. This cDNA was admixed with Real-time PCR Master Mix, primers specific to MyoD1 and Myogenin or β-actin gene, and Taqman probe. qRT-PCR was performed using AB7300 Real-time PCR system. The mRNA level of MyoD1 and Myogenin gene was quantified as a ratio to β-actin gene mRNA, and calculated with the value of fibroblast cultured in the general medium as 1.

The results are shown in FIG. 10. It could be confirmed that culturing in a skeleton muscle cell growth medium in the presence of ALK5 inhibitor II can convert human normal skin-derived fibroblast to myoblast expressing Myogenin and MyoD1 gene.

Figure 11:
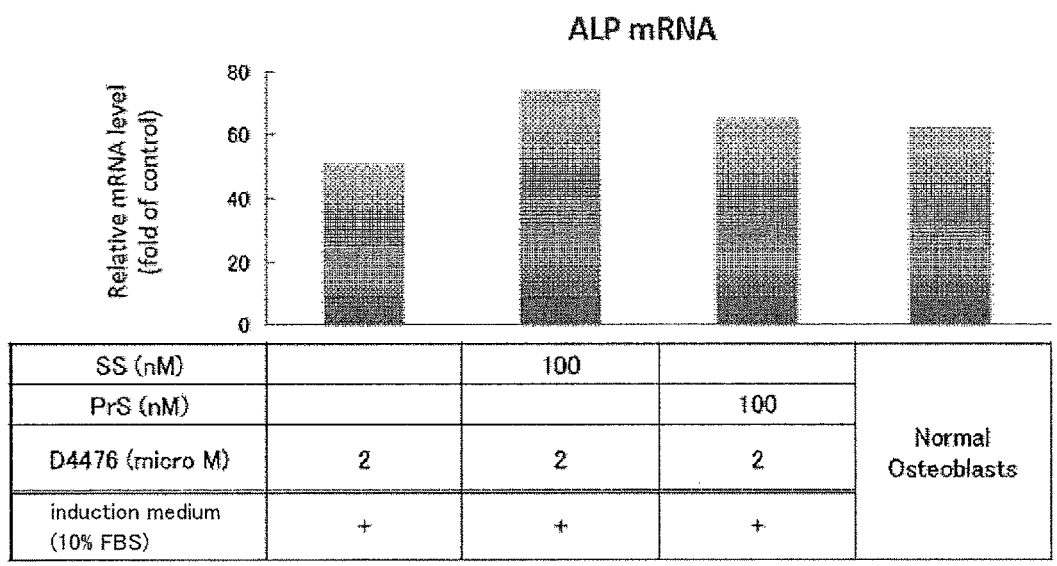
FIG. 11 shows the measurement results of a gene expression level by a real-time RT-PCR method.

Example 11 (FIG. 11)

Human normal skin fibroblast strain HDFs were seeded in a 24-well plate at a concentration of 5×10³ cells/well (day 0). The next day, the culture medium of each well was discarded, and exchanged with a fresh medium (500 l/well). The osteoblast induction medium is Dulbecco's modified Eagle's medium (DMEM), 50 μg/ml ascorbic acid, 10 mM β-glycerophosphate and 100 nM Dexamethasone added with 10% fetal bovine serum (FBS).

As shown in the Figure, Simvastatin (SS) or Pravastatin (PrS) (final concentration 100 nM) as a statin compound was further added to the medium.

After 28 days of culturing, the culture medium was removed from each well, and the cells were washed with PBS(-). Total RNA was recovered from the cells with ISOGEN II, and cDNA was synthesized using Rever Tra Ace qPCR RT Master Mix. Real-time PCR Master Mix, and Taqman probe and Primers specific to human alkaline phosphatase (ALP) gene were added, and Real-time RT-PCR was performed using AB7300 Real-time PCR system.

Figure 14:
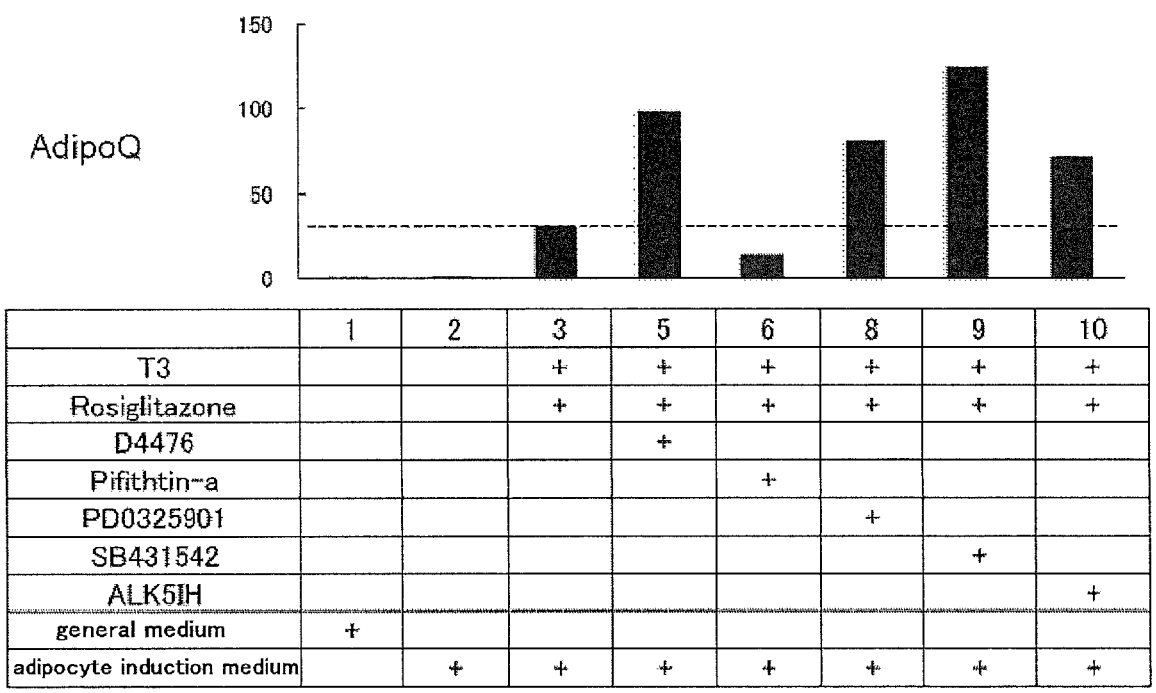
FIG. 14 shows the measurement results of a gene expression level by a real-time RT-PCR method.

The results are shown in FIG. 14 as a relative value with the value of normal human fibroblast as 1. It is clear that addition of SS, PrS together with D4476 more strongly induced ALP expression than by D4476 alone.

Figure 12:
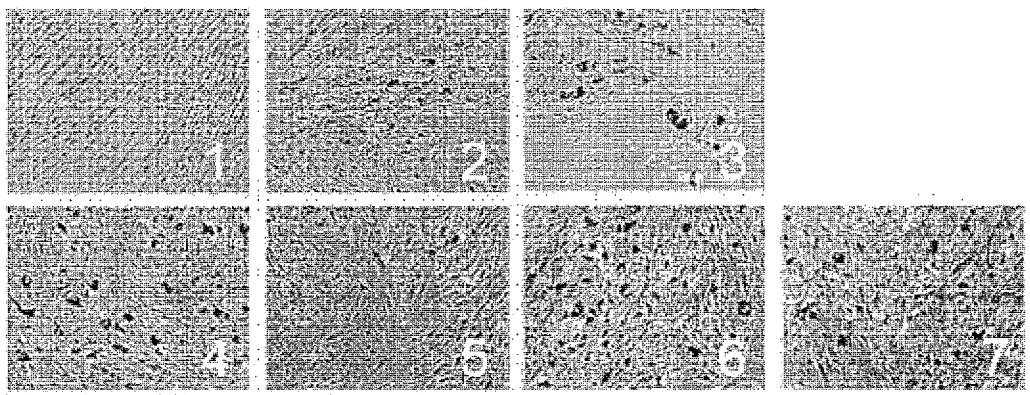
FIG. 12 shows the results of Oil Red O staining (staining Figure).

Example 12 (FIG. 12)

Human normal skin-derived fibroblast (human dermal fibroblasts; HDFs) were suspended in a general medium (Dulbecco's modified minimum essential medium; DMEM added with 10% FBS). This was seeded in a 24-well plate at a concentration of 1×10⁴ cells/well (day 0), and culturing was started in 5% $CO_2$/95% humidified air at 37° C. The next day, the culture supernatant was removed by suction and, as described in the Figure, a general medium, an adipocyte induction medium, or an adipocyte induction medium added with the compound and the like was added at 500 μL/well.

The adipocyte induction medium is a 10% FBS-added DMEM+MDI medium (10% FBS-added DMEM added with 0.5 mM 3-isobutyl-1-methylxanthine (IBMX), 0.5 μM dexamethason and 1 μg/mL Insulin).

The concentrations of the additives are as follows:
T3: 1 nM
Rosiglitazone: 1 μM
D4476: 2 μM
Pifithrin alpha [p53 inhibitor]: 5 μM
SB431542: 2 μM
ALK5 Inhibitor II: 2 μM.

The culture medium was exchanged with a fresh one every 3-4 days and the cells were cultured until day 14.

On day 14, the culture medium was removed from each well by suction, washed with PBS(-), and fixed with 10% formalin. After washing 3 times with sterile distilled water, Oil Red O staining solution was added, and the mixture was incubated at room temperature for 15 min. Then, the cells were washed with sterile distilled water and photographed with a phase contrast microscope at ×100 magnification.

The results are shown in FIG. 12. It is clear that culturing by adding any of D4476, SB431542 and ALK5 Inhibitor II in addition to T3 and Rosiglitazone converted fibroblast to brown adipocyte.

Figure 13:
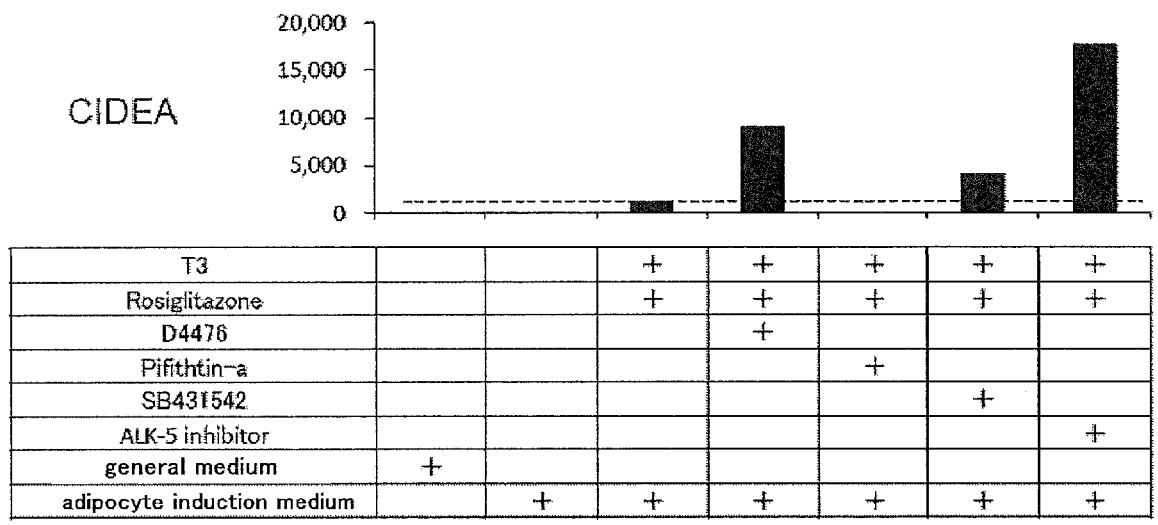
FIG. 13 shows the measurement results of a gene expression level by a real-time RT-PCR method.

Example 13 (FIG. 13)

Human normal skin-derived fibroblast (human dermal fibroblasts; HDFs) were suspended in a general medium (Dulbecco's modified minimum essential medium; DMEM added with 10% FBS). This was seeded in a 24-well plate at a concentration of 1×10⁴ cells/well (day 0), and culturing was started in 5% $CO_2$/95% humidified air at 37° C. The next day, the culture supernatant was removed by suction and, as described in the Figure, a general medium, an adipocyte induction medium, or an adipocyte induction medium added with each compound and the like was added at 500 μL/well.

The adipocyte induction medium is a 10% FBS-added DMEM+MDI medium (10% FBS-added DMEM added with 0.5 mM 3-isobutyl-1-methylxanthine (IBMX), 0.5 μM dexamethason and 1 μg/mL Insulin)

The concentrations of the additives are as follows:
T3: 1 nM
Rosiglitazone: 1 μM
D4476: 2 μM
Pifithrin alpha [p53 inhibitor]: 5 μM
SB431542: 2 μM
ALK5 Inhibitor II: 2 μM.

The culture medium was exchanged with a fresh one every 3-4 days and the cells were cultured until day 14. On day 14, the culture medium was removed from each well by suction, washed with PBS(-) and total RNA was extracted from the cells with ISOGEN II. cDNA was synthesized from the RNA by using Rever Tra Ace qPCR RT Master Mix. The cDNA was admixed with Real-time PCR Master Mix, primers specific to CIDEA gene or β actin gene and Taqman probe. qRT-PCR was performed using AB7300 Real-time PCR system. The mRNA level of CIDEA gene was quantified as a ratio to f actin gene mRNA and calculated with the value of fibroblast cultured in the general medium as 1.

The results thereof are shown in FIG. 13. It is clear that culturing by adding any of D4476, SB431542 and ALK5 Inhibitor II in addition to T3 and Rosiglitazone converted fibroblast to brown adipocytes expressing mRNA of CIDEA gene.

Example 14 (FIG. 14)

Human normal skin-derived fibroblast (human dermal fibroblasts; HDFs) were suspended in a general medium (Dulbecco's modified minimum essential medium; DMEM added with 10% FBS). This was seeded in a 24-well plate at a concentration of $1\times10^4$ cells/well (day 0), and culturing was started in 5% $CO_2$/95% humidified air at 37° C. The next day, the culture supernatant was removed by suction and, as described in the Figure, a general medium, an adipocyte induction medium, or an adipocyte induction medium added with each small molecule compound and the like was added at 500 UL/well.

The adipocyte induction medium is a 10% FBS-added DMEM+MDI medium (10% FBS-added DMEM added with 0.5 mM 3-isobutyl-1-methylxanthine (IBMX), 0.5 µM dexamethason and 1 µg/mL Insulin).

The concentrations of the additives are as follows:
T3: 1 nM
Rosiglitazone: 1 µM
D4476: 2 µM.
Pifithrin alpha [p53 inhibitor]: 5 µM
PD0325901: 1 µM
SB431542: 2 µM.
ALK5 Inhibitor II: 2 µM.

The culture medium was exchanged with a fresh one every 3-4 days and the cells were cultured until day 14.

On day 14, the culture medium was removed from each well by suction, washed with PBS(-) and total RNA was extracted from the cells with ISOGEN II. cDNA was synthesized from the RNA by using Rever Tra Ace qPCR RT Master Mix. The cDNA was admixed with Real-time PCR Master Mix, primers specific to AdipoQ or f actin gene and Taqman probe. qRT-PCR was performed using AB7300 Real-time PCR system. The mRNA level of AdipoQ gene was quantified as a ratio to β actin gene mRNA and calculated with the value of fibroblast cultured in the general medium as 1.

The results thereof are shown in FIG. 14. It is clear that culturing by adding any of D4476, PD0325901, SB431542 and ALK5 Inhibitor II in addition to T3 and Rosiglitazone converted fibroblast to brown adipocytes expressing mRNA of AdipoQ gene.

Example 15 (FIG. 15)

Human normal skin-derived fibroblast (human dermal fibroblasts; HDFs) were suspended in a general medium (Dulbecco's modified minimum essential medium; DMEM added with 10% FBS). This was seeded in a 24-well plate at a concentration of $1\times10^4$ cells/well (day 0), and culturing was started in 5% $CO_2$/95% humidified air at 37° C. The next day, the culture supernatant was removed by suction and, as described in the Figure, a general medium, an adipocyte induction medium, or an adipocyte induction medium added with each small molecule compound and the like was added at 500 L/well.

The adipocyte induction medium is a 10% FBS-added DMEM+MDI medium (10% FBS-added DMEM added with 0.5 mM 3-isobutyl-1-methylxanthine (IBMX), 0.5 µM dexamethason and 1 µg/mL Insulin).

The concentrations of the additives are as follows:
T3: 1 nM
Rosiglitazone: 1 µM
D4476: 2 µM
SB431541: 2 µM
ALK5 inhibitor II: 2 µM.

The culture medium was exchanged with a fresh one every 3-4 days and the cells were cultured until day 14.

On day 14, the culture medium was removed from each well by suction, and washed with PBS(-). The cells were fixed with 4% para-formaldehyde, washed with PBS(-), reacted for 5 min with BODIPY 493/503 (Invitrogen)/PBS solution at room temperature and washed 3 times with PBS. The cells were photographed with a fluorescence microscope at ×200 magnification and the fluorescence intensity was measured.

Figure 15A:
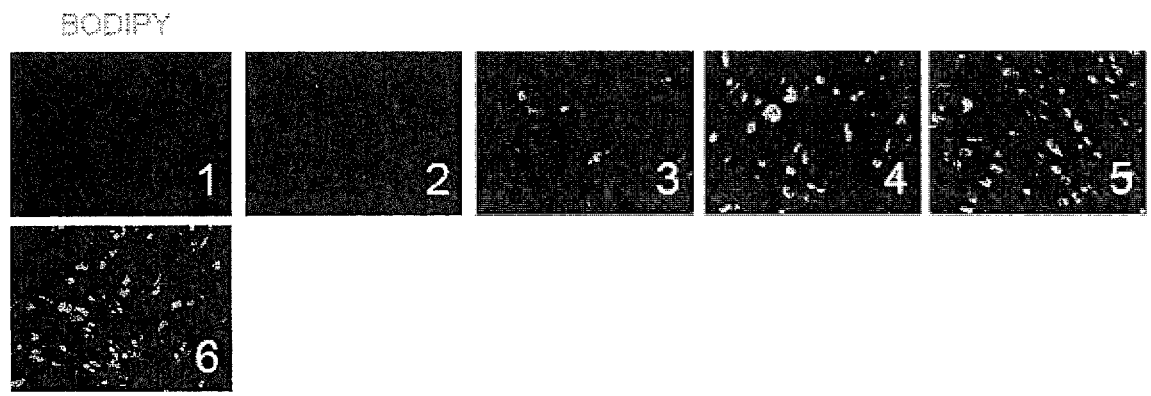
FIG. 15A shows the results of Bodipy staining (staining Figure).
Figure 15B:
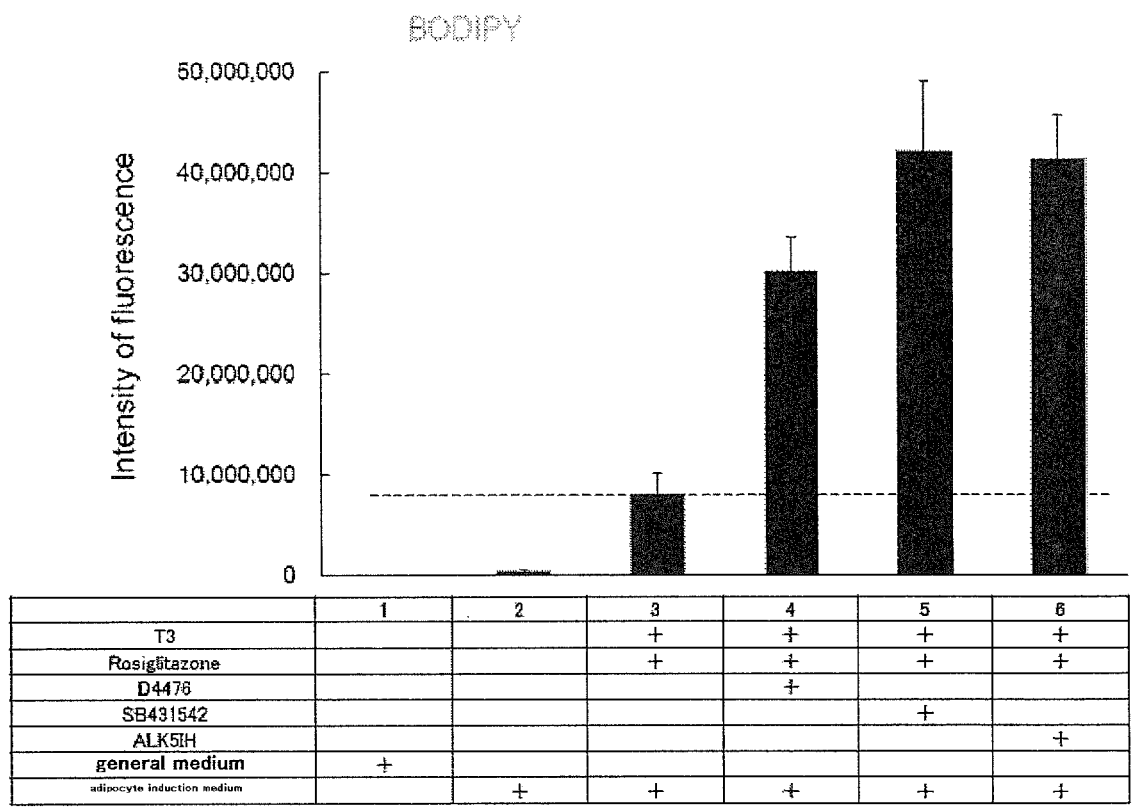
FIG. 15B shows the results of Bodipy staining (fluorescence intensity measurement).

The results thereof are shown in FIG. 15A (fluorescence microscopic images) and FIG. 15B (fluorescence intensity). It is clear that culturing by adding any of D4476, SB431541 and ALK5 Inhibitor II in addition to T3 and Rosiglitazone converted fibroblast to brown adipocytes having lipid droplets stained with BODIPY.

Figure 20:
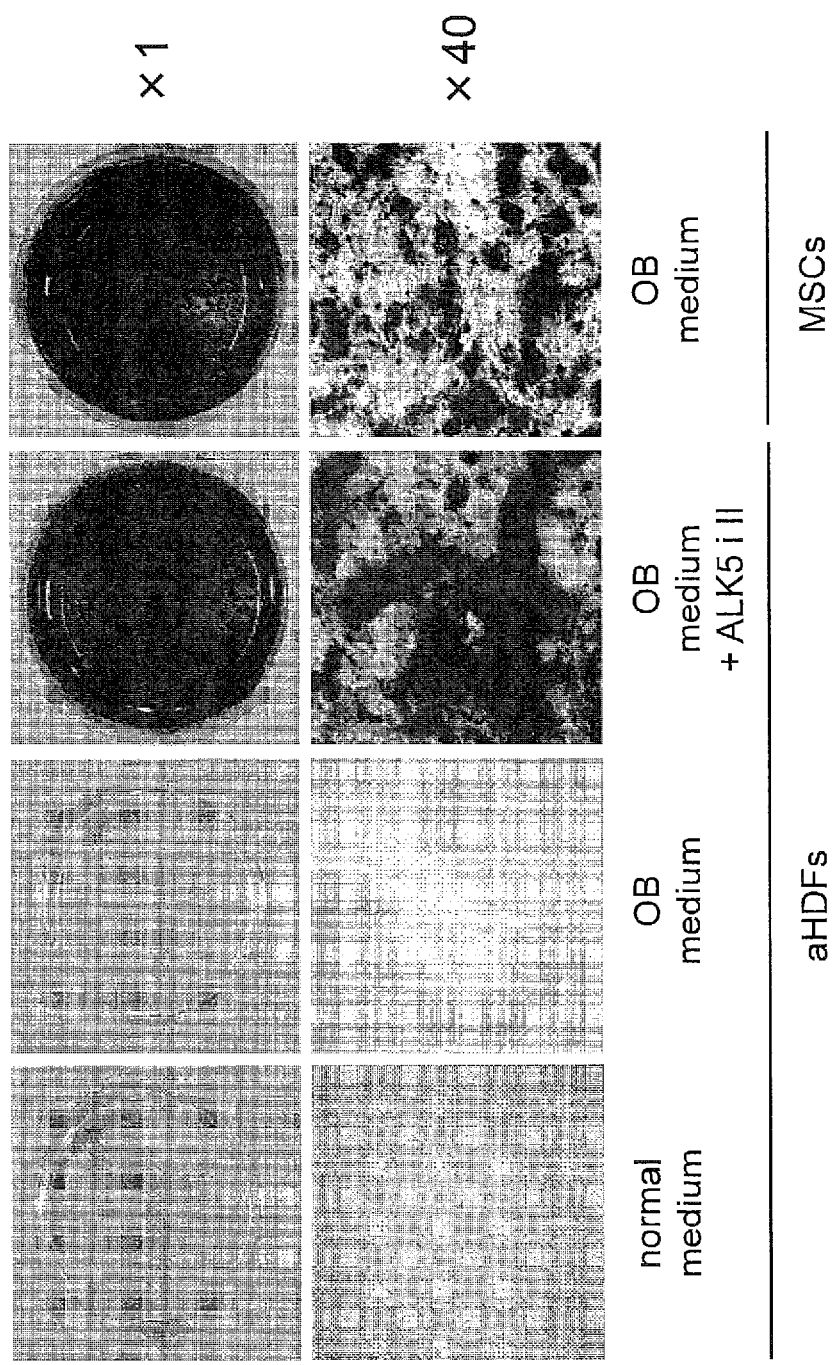
FIG. 20 shows the results of Alizarin Red S staining (staining Figure).

Example 16 (FIG. 20)

Human normal skin-derived fibroblasts (human dermal fibroblasts; HDFs) or human mesenchymal stem cells (MSC) were suspended in the general medium (Dulbecco's modified minimum essential medium; DMEM added with 10% FBS). This was seeded in a 24-well plate at a concentration of $1\times10^4$ cells/well (day 0), and culturing was started in 5% $CO_2$/95% humidified air at 37° C. The next day, the culture supernatant was removed by suction and, as described in the Figure, the general medium (Normal medium), a calcification induction medium (OB medium), or a calcification induction medium added with ALK5 inhibitor II (ALK5 i II) at a concentration of 4 µM (OB medium+ALK5 i II) was added at 500 µL/well.

The calcification induction medium is a 10% FBS DMEM added with 50 µg/ml ascorbic acid, 10 mM β-glycerophosphate and 100 nM Dexamethasone. The culture medium was exchanged with a fresh one every 3-4 days, and culturing was performed until day 18.

On day 18, the culture medium was removed from each well by suction, washed with PBS(-), and fixed with 10% formalin. It was washed 3 times with sterile distilled water. The well after staining with Alizarin Red S was washed with sterile distilled water, and photographed with an inverted microscope at ×40 magnification.

The results are shown in FIG. 20. It is clear that culturing in a calcification induction medium added with ALK5 inhibitor II converted human skin-derived fibroblast to osteoblast that produces a large amount of calcified bone matrix.

Figure 21:
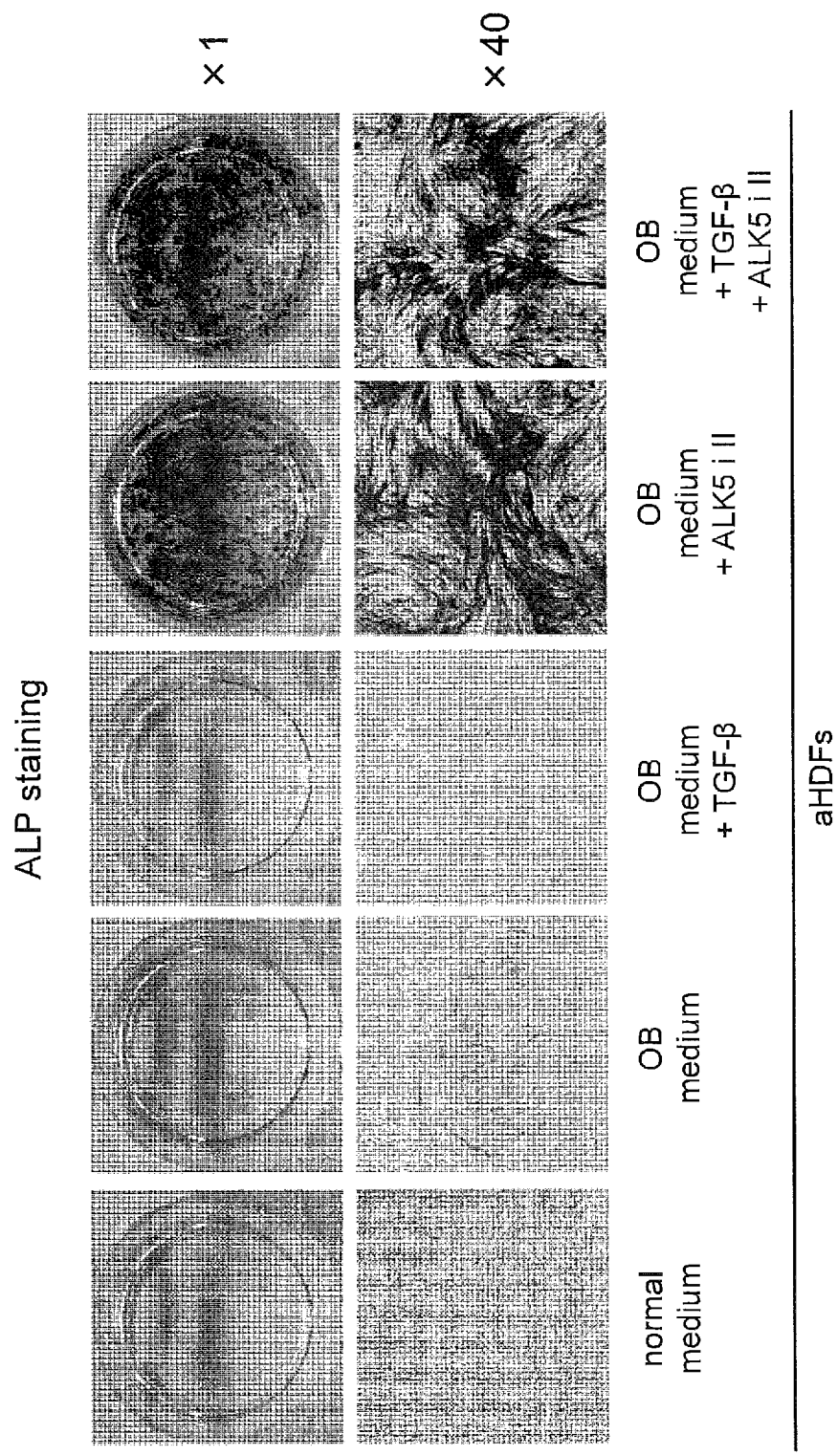
FIG. 21 shows the results of ALP staining (staining Figure).

Example 17 (FIG. 21)

Human normal skin-derived fibroblasts (human dermal fibroblasts; HDFs) were suspended in a general medium (Dulbecco's modified minimum essential medium; DMEM added with 10% FBS). This was seeded in a 24-well plate at a concentration of $1\times10^4$ cells/well (day 0), and culturing was started in 5% $CO_2$/95% humidified air at 37° C. The next day, the culture supernatant was removed by suction and, as described in the Figure, the general medium, a calcification induction medium, or a calcification induction medium added with ALK5 inhibitor II and/or TGF-β was added at 500 µL/well.

The calcification induction medium is a 10% FBS DMEM added with 50 µg/ml ascorbic acid, 10 mM β-glycerophosphate and 100 nM Dexamethasone. The culture medium was exchanged with a fresh one every 3-4 days, and culturing was performed until day 13.

On day 13, the culture medium was removed from each well by suction, washed with PBS(−), and fixed with a fixative. It was washed 3 times with sterile distilled water. The well after ALP staining was washed with sterile distilled water, and photographed with an inverted microscope at ×40 magnification.

The concentrations of the compound and cytokine added to the medium are as follows.

ALK5 inhibitor II: 4 µM
TGF-β: 50 ng/ml.

The results are shown in FIG. 21. It is clear that culturing in a calcification induction medium added with ALK5 inhibitor II converted human normal skin-derived fibroblast to osteoblast having high ALP activity.

Figure 22:
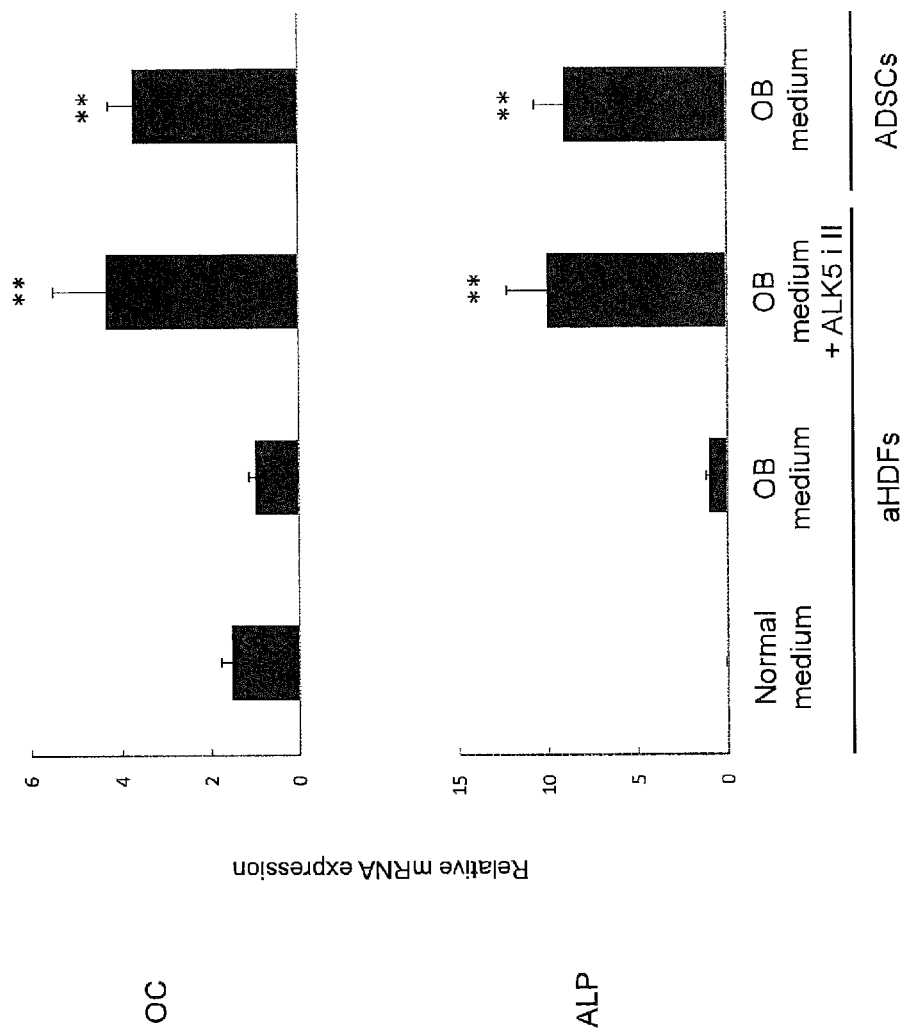
FIG. 22 shows the measurement results of a gene expression level by a real-time RT-PCR method.

Example 18 (FIG. 22)

Human normal skin-derived fibroblasts (human dermal fibroblasts; HDFs) or human fat-derived mesenchymal stem cells (human adipose derived stem cells; ADSCs) were suspended in a general medium (Dulbecco's modified minimum essential medium; DMEM added with 10% FBS). This was seeded in a 24-well plate at a concentration of $1 \times 10^4$ cells/well (day 0), and culturing was started in 5% $CO_2$/95% humidified air at 37° C. The next day, the culture supernatant was removed by suction and, as described in the Figure, the general medium, a calcification induction medium, or a calcification induction medium added with ALK5 inhibitor II at a concentration of 4 µM was added at 500 µL/well.

The calcification induction medium is a 10% FBS DMEM added with 50 µg/ml ascorbic acid, 10 mM β-glycerophosphate and 100 nM Dexamethasone. The culture medium was exchanged with a fresh one every 3-4 days, and culturing was performed until day 18.

On day 18, the culture medium was removed from each well by suction, washed with PBS, and total RNA was extracted from the cell with ISOGEN II. cDNA was synthesized from the RNA by using Rever Tra Ace qPCR RT Master Mix. This cDNA was admixed with Real-time PCR Master Mix, and primers specific to Osteocalcin, Alkaline Phosphatase or β-actin gene, and Taqman probe. qRT-PCR was performed using AB7300 Real-time PCR system. The mRNA level of Osteocalcin (Oc) and Alkaline Phosphatase (ALP) gene was quantified as a ratio to β-actin gene mRNA, and calculated with the value of fibroblast cultured in a calcification induction medium as 1.

The results are shown in FIG. 22. It is clear that culturing in a calcification induction medium added with ALK5 inhibitor II converted human skin-derived fibroblast to osteoblast expressing osteocalcin gene and ALP gene. In the Figure, * and ** respectively show $p<0.05$ and $p<0.01$ relative to calcification induction medium (OB medium) (*$p<0.05$ and **$p<0.01$ vs. the OB medium. Values are means±S.D. (n=4)).

Figure 23:
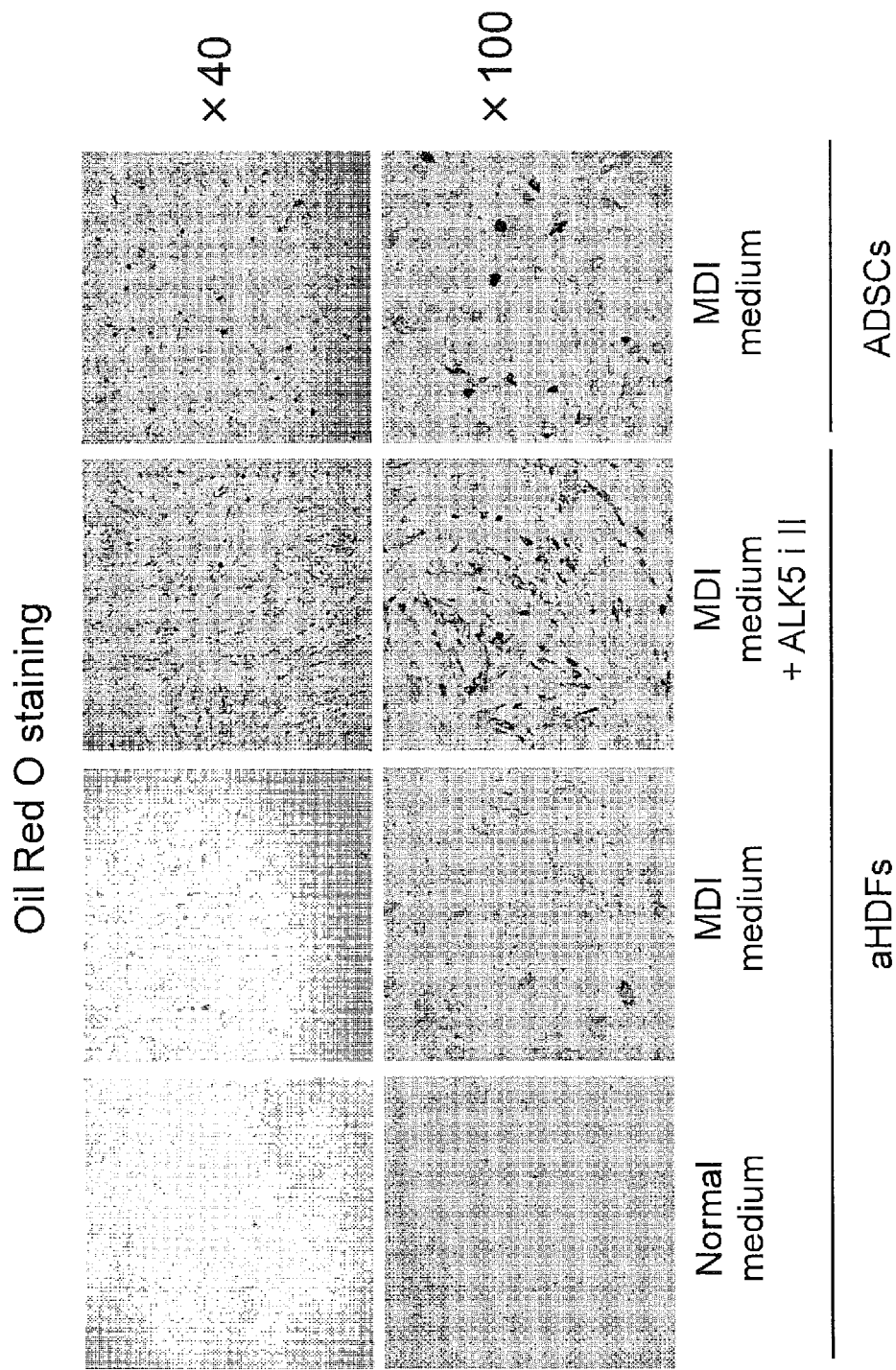
FIG. 23 shows the results of Oil Red O staining (staining Figure).

Example 19 (FIG. 23)

Human normal skin-derived fibroblasts (human dermal fibroblasts; HDFs) or human fat-derived mesenchymal stem cells (human adipose derived stem cells; ADSCs) were suspended in a general medium (Dulbecco's modified minimum essential medium; DMEM added with 10% FBS). This was seeded in a 24-well plate at a concentration of $2 \times 10^4$ cells/well (day 0), and culturing was started in 5% $CO_2$/95% humidified air at 37° C. The next day, the culture supernatant was removed by suction and, as described in the Figure, the general medium (Normal medium), MDI medium (adipocyte induction medium for fibroblast), or MDI medium added with ALK5 inhibitor II at a concentration of 4 µM (MDI medium+ALK5 i II) was added at 500 µL/well.

MDI medium is 10% FBS DMEM added with 0.5 mM 3-isobutyl-1-methylxanthine (IBMX), 0.5 µM dexamethasone, and 1 µg/mL Insulin. The culture medium was exchanged with a fresh one every 3-4 days, and culturing was performed until day 14.

On day 14, the culture medium was removed from each well by suction, washed with PBS(−), and fixed with 10% formalin. It was washed 3 times with sterile distilled water. The well after staining with Oil Red O was washed with sterile distilled water, and photographed with an inverted microscope at ×40, ×100 magnifications.

The results are shown in FIG. 23. It is clear that culturing in MDI medium added with ALK5 inhibitor II converted human skin-derived fibroblast to white adipocyte that accumulates a large amount of lipid droplets.

Figure 24:
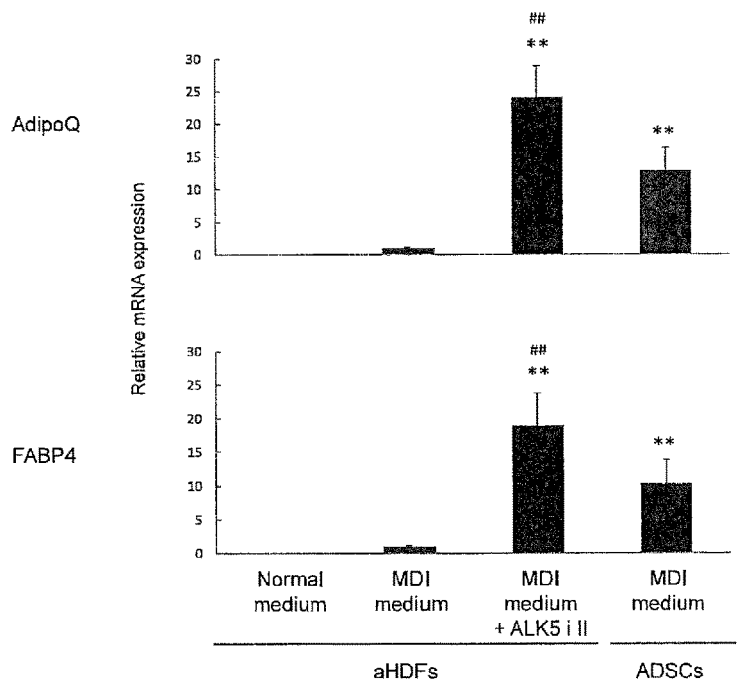
FIG. 24 shows the measurement results of a gene expression level by real-time RT-PCR method.

Example 20 (FIG. 24)

Human normal skin-derived fibroblasts (human dermal fibroblasts; HDFs) or human fat-derived mesenchymal stem cells (human adipose derived stem cells; ADSCs) were suspended in a general medium (Dulbecco's modified minimum essential medium; DMEM added with 10% FBS) (Normal medium). This was seeded in a 24-well plate at a concentration of $1 \times 10^4$ cells/well (day 0), and culturing was started in 5% $CO_2$/95% humidified air at 37° C. The next day, the culture supernatant was removed by suction and, as described in the Figure, the general medium, MDI medium or MDI medium added with ALK5 inhibitor II at a concentration of 4 µM was added at 500 µL/well.

MDI medium (3-isobutyl-1-methylxanthine/dexamethasone/insulin-containing medium) is 10% FBS DMEM added with 0.5 mM 3-isobutyl-1-methylxanthine (IBMX), 0.5 µM dexamethasone, and 1 µg/mL Insulin. The culture medium was exchanged with a fresh one every 3-4 days, and culturing was performed until day 14.

On day 14, the culture medium was removed from each well by suction, washed with PBS, and total RNA was extracted from the cell with ISOGEN II. cDNA was synthesized from the RNA by using Rever Tra Ace qPCR RT Master Mix. This cDNA was admixed with Real-time PCR Master Mix, and primers specific to AdipoQ, FABP4 or β-actin gene, and Taqman probe. qRT-PCR was performed using AB7300 Real-time PCR system. The mRNA level of AdipoQ and FABP4 gene was quantified as a ratio to β-actin gene mRNA level, and calculated with the value of fibroblast cultured in MDI medium as 1.

The results are shown in FIG. 24. It is clear that culturing in MDI medium added with ALK5 inhibitor II converted human skin-derived fibroblast to white adipocyte expressing AdipoQ gene and FABP4 gene.

Figure 25:
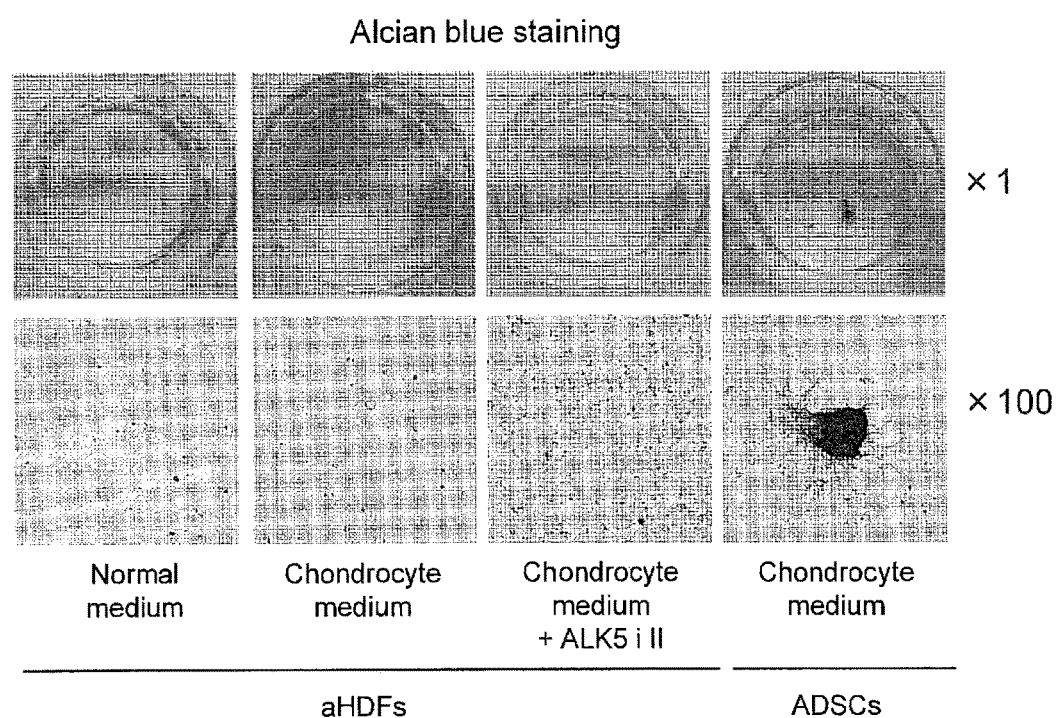
FIG. 25 shows the results of alcian blue staining (staining Figure).

Example 21 (FIG. 25)

Human normal skin-derived fibroblasts (human dermal fibroblasts; HDFs) or human fat-derived mesenchymal stem cells (human adipose derived stem cells; ADSCs) were suspended in a general medium (Dulbecco's modified minimum essential medium; DMEM added with 10% FBS). This was seeded in the center of a fibronectin-coated 24-well plate at a concentration of $1 \times 10^4$ cells/well (day 0), and culturing was started in 5% $CO_2$/95% humidified air at 37° C. The next day, the culture supernatant was removed by suction and, as described in the Figure, the general medium, a cartilage induction medium (Chondrocyte medium), or a cartilage induction medium added with ALK5 inhibitor II at a concentration of 4 μM (Chondrocyte medium+ALK5 i II) was added at 500 μL/well.

The cartilage induction medium is 1% FBS DMEM added with 50 μg/ml ascorbic acid, 1% insulin-transferrin-selenium, 10 ng/ml BMP-2, 10 ng/ml TGF-β, 10 ng/ml GDF5, and 10 ng/nl b-FGF. The culture medium was exchanged with a fresh one every 3-4 days, and culturing was performed until day 21.

On day 21, the culture medium was removed from each well by suction, washed with PBS(−), and fixed with 10% formalin. It was washed 3 times with sterile distilled water. The well after staining with Alcian blue is washed with sterile distilled water, and photographed with an inverted microscope at ×100 magnification.

The results are shown in FIG. 25. It is clear that culturing in cartilage induction medium added with ALK5 inhibitor II converted human skin-derived fibroblast to chondrocyte that produces a large amount of cartilage matrix.

Figure 26:
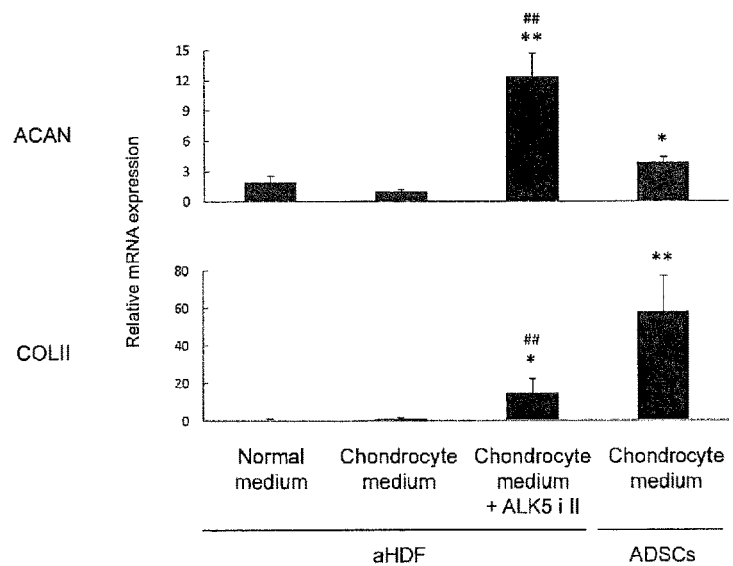
FIG. 26 shows the measurement results of a gene expression level by a real-time RT-PCR method.

Example 22 (FIG. 26)

Human normal skin-derived fibroblasts (human dermal fibroblasts; HDFs) or human fat-derived mesenchymal stem cells (human adipose derived stem cells; ADSCs) were suspended in a general medium (Dulbecco's modified minimum essential medium; DMEM added with 10% FBS). This was seeded in the center of a fibronectin-coated 24-well plate at a concentration of $1\times10^4$ cells/well (day 0), and culturing was started in 5% $CO_2$/95% humidified air at 37° C. The next day, the culture supernatant was removed by suction and, as described in the Figure, the general medium, a cartilage induction medium, or a cartilage induction medium added with ALK5 inhibitor II at a concentration of 4 μM was added at 500 μL/well.

The cartilage induction medium is 1% FBS DMEM added with 50 μg/ml ascorbic acid, 1% insulin-transferrin-selenium, 10 ng/ml BMP-2, 10 ng/ml TGF-β, 10 ng/ml GDF5, and 10 ng/nl b-FGF. The culture medium was exchanged with a fresh one every 3-4 days, and culturing was performed until day 21.

On day 21, the culture medium was removed from each well by suction, washed with PBS, and total RNA was extracted from the cell with ISOGEN II. cDNA was synthesized from the RNA by using Rever Tra Ace qPCR RT Master Mix. This cDNA was admixed with Real-time PCR Master Mix, and primers specific to Aggrecan, Type II collagen or β-actin gene, and Taqman probe. qRT-PCR was performed using AB7300 Real-time PCR system. The mRNA level of Aggrecan (ACAN) and type II collagen gene was quantified as a ratio to β-actin gene mRNA level, and calculated with the value of fibroblast cultured in cartilage induction medium as 1.

The results are shown in FIG. 26. It is clear that culturing in cartilage induction medium added with ALK5 inhibitor II converted human skin-derived fibroblast to chondrocyte that expresses Aggrecan gene and type II collagen gene.

Figure 27:
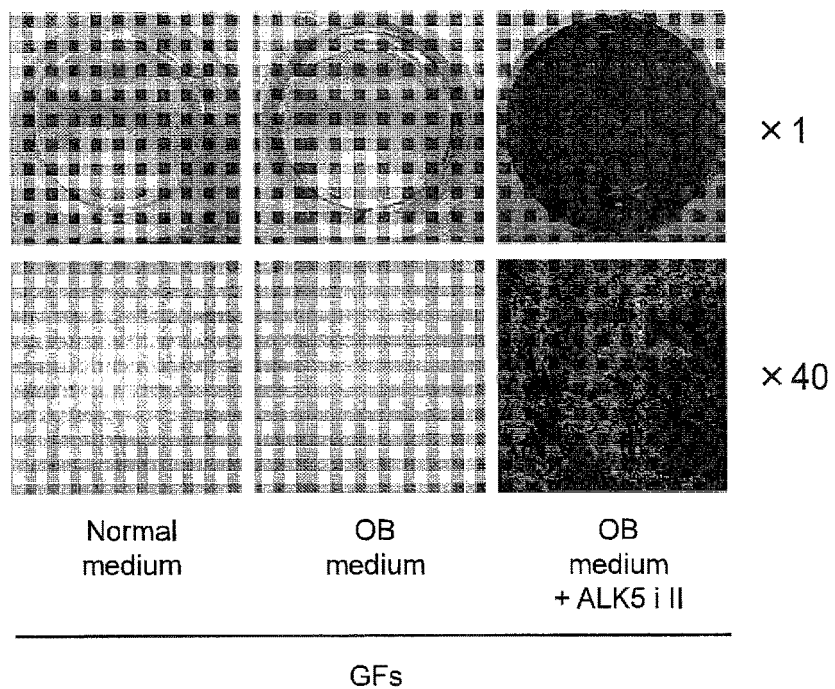
FIG. 27 shows the results of Alizarin Red S staining (staining Figure).

Example 23 (FIG. 27)

Human normal gingival-derived fibroblasts (human gingival fibroblasts; GFs) were suspended in a general medium (Dulbecco's modified minimum essential medium; DMEM added with 10% FBS). This was seeded in a 24-well plate at a concentration of $1\times10^4$ cells/well (day 0), and culturing was started in 5% $CO_2$/95% humidified air at 37° C. The next day, the culture supernatant was removed by suction and, as described in the Figure, the general medium, a calcification induction medium, or a calcification induction medium added with ALK5 inhibitor II at a concentration of 4 μM was added at 500 μL/well.

The calcification induction medium is a 10% FBS DMEM added with 50 μg/ml ascorbic acid, 10 mM β-glycerophosphate and 100 nM Dexamethasone. The culture medium was exchanged with a fresh one every 3-4 days, and culturing was performed until day 18.

On day 18, the culture medium was removed from each well by suction, washed with PBS(−), and fixed with 10% formalin. It was washed 3 times with sterile distilled water. The well after Alizarin Red S staining was washed with sterile distilled water, and photographed with an inverted microscope at ×40 magnification.

The results are shown in FIG. 27. It is clear that culturing in a calcification induction medium added with ALK5 inhibitor II converted human gingival-derived fibroblast to osteoblast that produces a large amount of calcified bone matrix.

Figure 28:
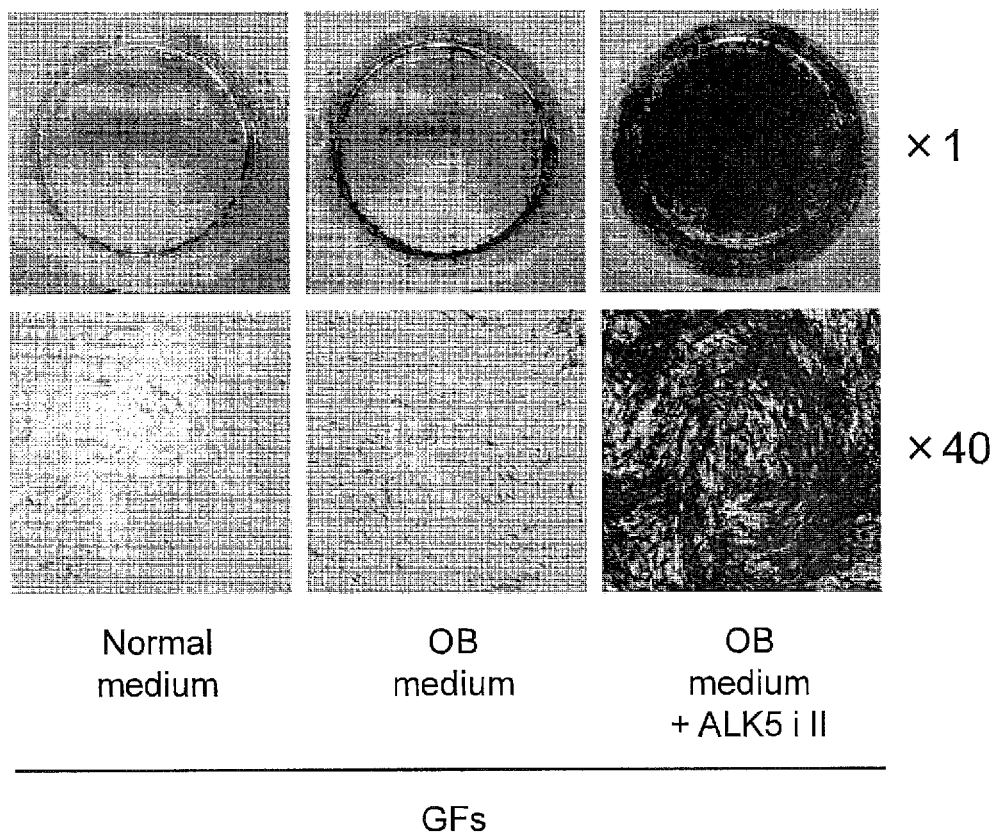
FIG. 28 shows the results of ALP staining (staining Figure).

Example 24 (FIG. 28)

Human normal gingival-derived fibroblasts (human gingival fibroblasts; GFs) were suspended in a general medium (Dulbecco's modified minimum essential medium; DMEM added with 10% FBS). This was seeded in a 24-well plate at a concentration of $1\times10^4$ cells/well (day 0), and culturing was started in 5% $CO_2$/95% humidified air at 37° C. The next day, the culture supernatant was removed by suction and, as described in the Figure, the general medium, a calcification induction medium, or a calcification induction medium added with ALK5 inhibitor II at a concentration of 4 μM was added at 500 μL/well.

The calcification induction medium is a 10% FBS DMEM added with 50 μg/ml ascorbic acid, 10 mM β-glycerophosphate and 100 nM Dexamethasone. The culture medium was exchanged with a fresh one every 3-4 days, and culturing was performed until day 18.

On day 18, the culture medium was removed from each well by suction, washed with PBS(−), and fixed with a fixative. It was washed 3 times with sterile distilled water. The well after ALP staining was washed with sterile distilled water, and photographed with an inverted microscope at ×40 magnification.

The results are shown in FIG. 28. It is clear that culturing in a calcification induction medium added with ALK5 inhibitor II converted human gingival-derived fibroblast to osteoblast having high ALP activity.

Figure 29:
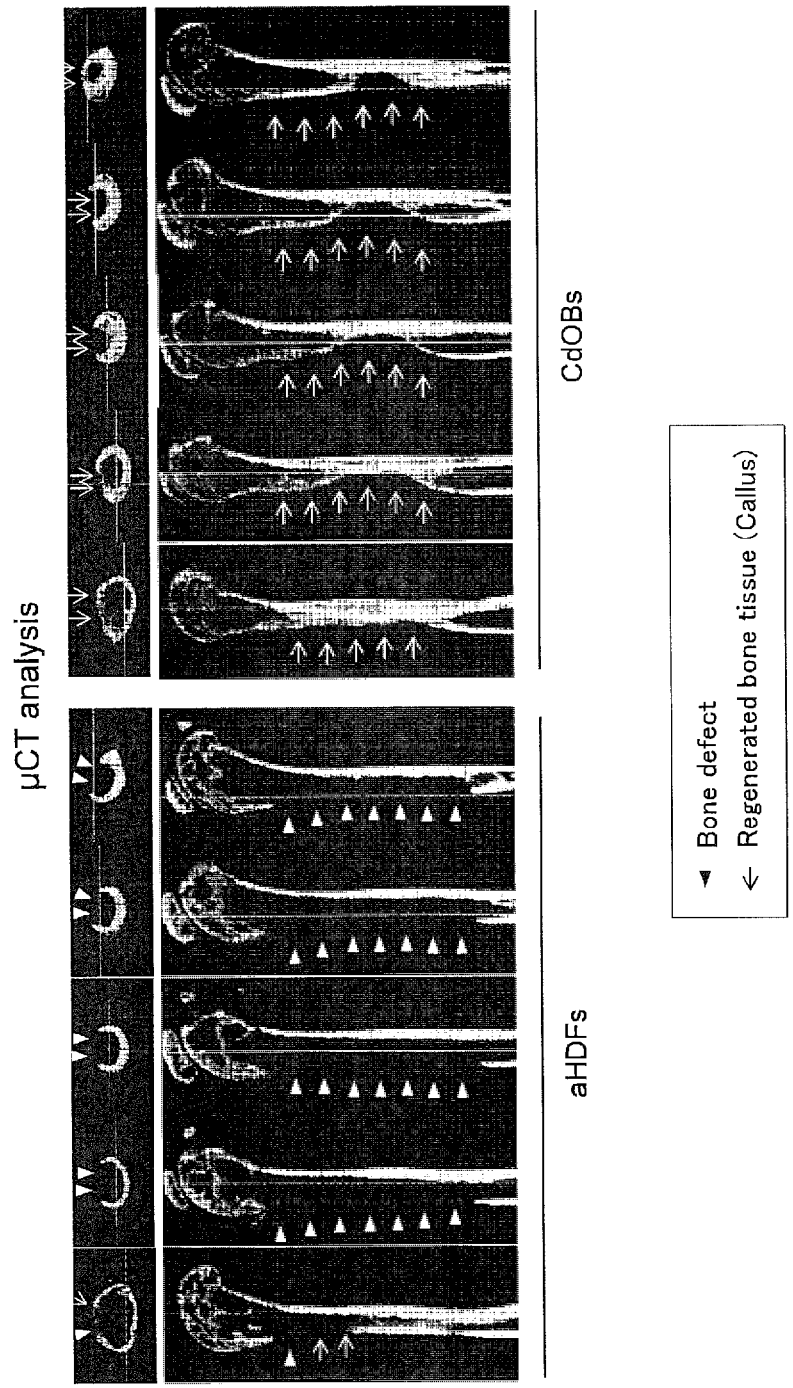
FIG. 29 shows a tomographic image of μCT (μCT analysis). Arrowhead shows a bone defect, and an arrow shows a regenerated bone tissue (Callus).

Example 25 (FIG. 29)

Animal experiments were conducted with the approval of the affiliated institution. Male 8-week-old NOD/SCID mice (Charles River) were anesthetized. A partial bone defect having a diameter of about 7 mm was created in the left femoral shaft by using a dental drill under water injection. Cells obtained by culturing HDFs in the same manner as in the below-mentioned Example 16 in the presence of ALK5 inhibitor II for 13 days (CdOBs; Chemical-mediated directly converted osteoblasts) were suspended with Matrigel (BD Bioscience, San Jose, CA), and transplanted to the bone defect area and surrounding bone surface at a concentration of $5\times10^5$ cells/mouse. Mice in which bone defects were similarly prepared and fibroblasts were suspended with Matrigel and transplanted thereinto were also prepared.

After 21 days, the mice were euthanized, the thigh was excised, fixed with neutral formalin, and micro-computed tomography (CT) was performed using an X-ray CT device (Scan Xmate-L090, Com Scan Techno, Yokohama, Japan).

A tomographic image of µCT is shown in FIG. 29. It is clear that CdOB formed osteogenesis in the bone defect area in the body of the mouse.

Figure 30:
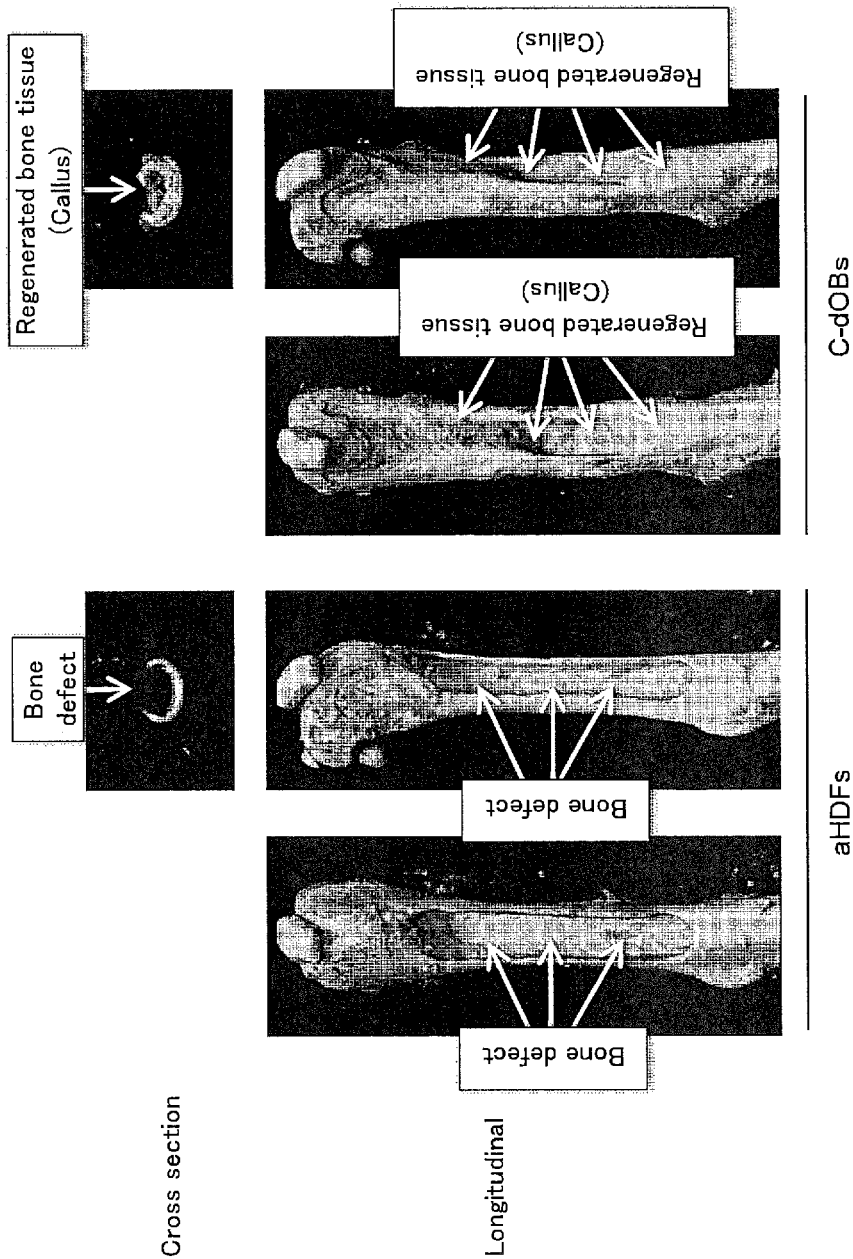
FIG. 30 shows a 3D reconstruction image of μCT. An image on day 21 post-transplantation (21 days after transplantation). An arrow shows a bone defect or regenerated bone tissue (Callus). The upper panel is a cross section, and the lower panel is a longitudinal section.

Example 26 (FIG. 30)

FIG. 30 shows an image obtained by three-dimensionally constructing the µCT image of Example 25. It was shown that the cells cultured with the addition of ALK5 inhibitor II have osteogenesis ability in vivo. It is clear that CdOB formed osteogenesis in the bone defect area in the body of the mouse.

Figure 31:
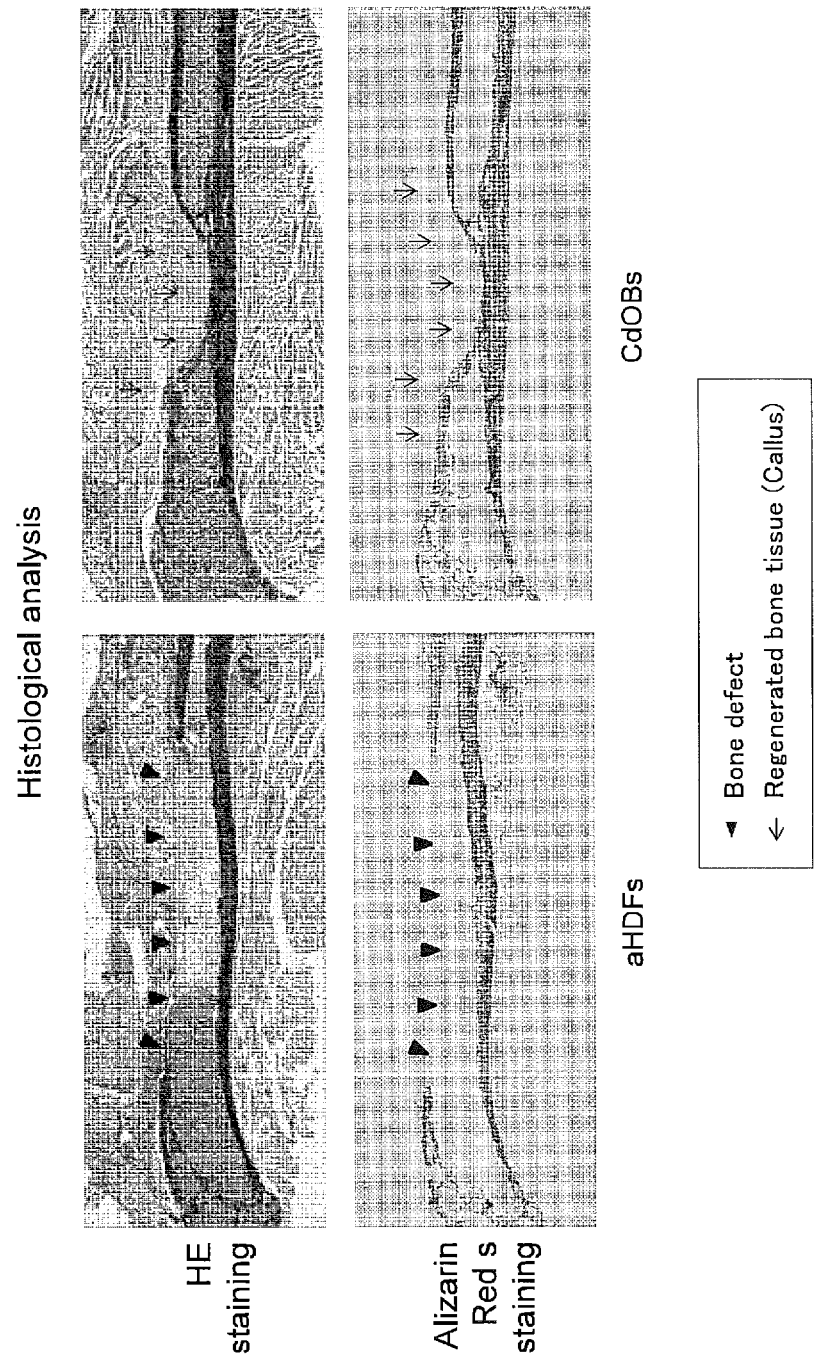
FIG. 31 shows the results of histological analysis of hematoxylin-eosin staining (HE staining) and Alizarin Red S staining.

Example 27 (FIG. 31)

Animal experiments were conducted with the approval of the affiliated institution. A transplantation experiment was performed in the same manner as in the above-mentioned Example 25. Mice transplanted with fibroblasts were also prepared. After 21 days, the mice were euthanized, the thigh was excised as in Example 25, fixed with neutral formalin, bone tissue was embedded with SCEM (Leica Microsystem) compound and rapidly frozen. After slicing into 6 µm sections, continuous sections were stained with Hematoxylin Eosin (H&E) and Alizarin Red S.

The results (×40 microscopic image) are shown in FIG. 31. It is clear that CdOB formed osteogenesis in the bone defect area in the body of the mouse.

Figure 32:
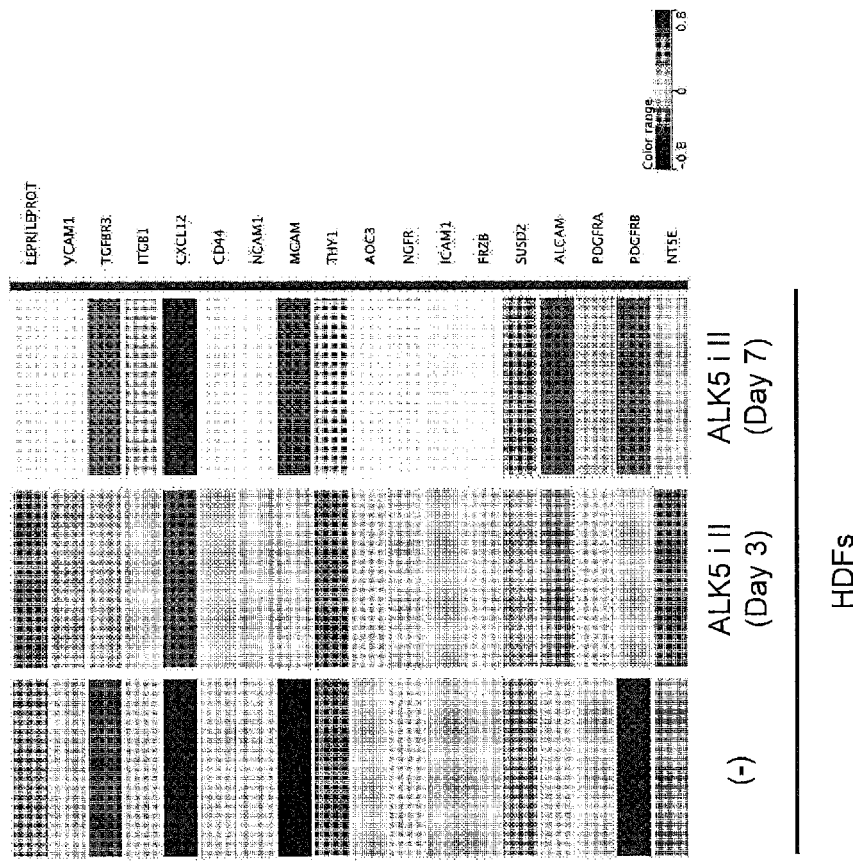
FIG. 32 is a heat map showing an expression level of MSC marker genes by DNA microarray analysis.

Example 28 (FIG. 32)

Human normal skin fibroblast cell strain HDFs were cultured in 60 mm culture dish and cultured in general medium (−). HDFs were cultured in the general medium added with 4 µM ALK5 inhibitor II for 3 or 7 days. Total RNA was recovered from these cells by ISOGEN II. The mRNA expression pattern of each cell was analyzed genome-wide by using a DNA chip (Affymetrix). A heat map showing the expression level of MSC marker is shown in FIG. 32. It is clear that culturing in a medium added with ALK5 inhibitor II converted fibroblasts to mesenchymal stem cells (MSCs).

Figure 33:
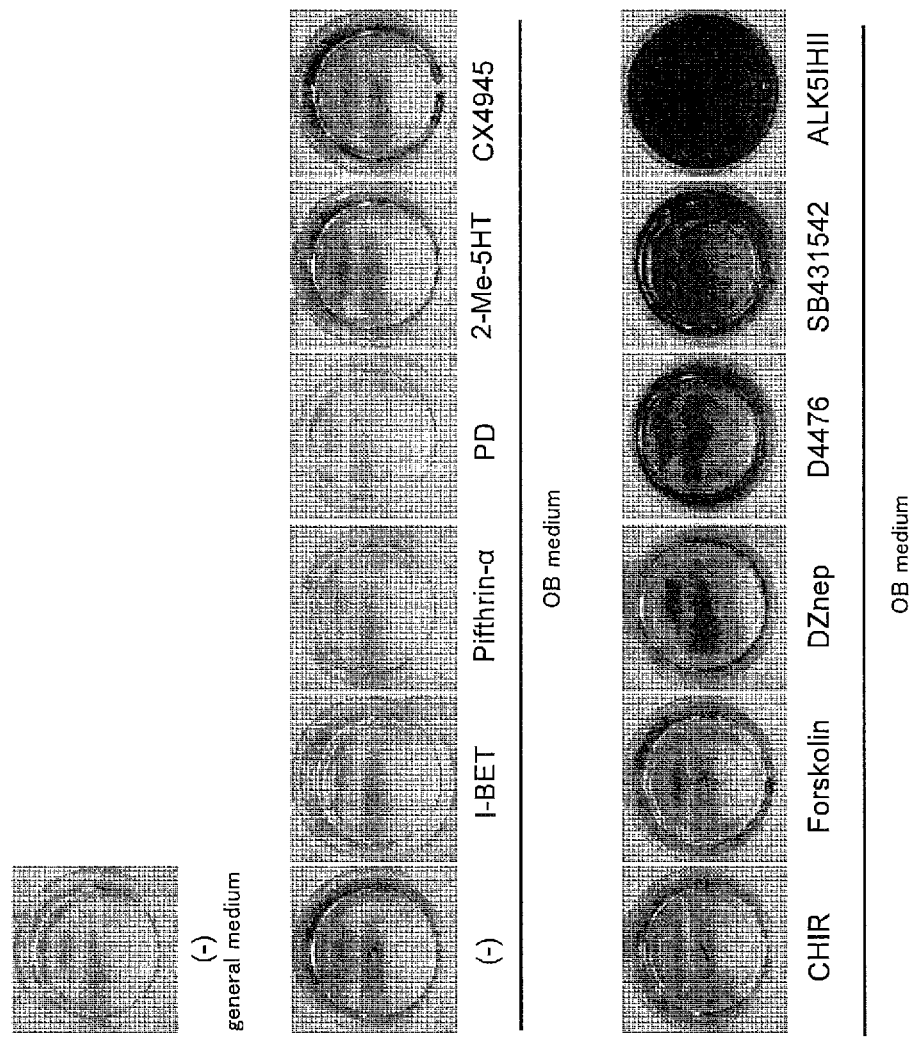
FIG. 33 shows the results of Alizarin Red S staining (staining Figure).

Example 29 (FIG. 33)

Human normal skin-derived fibroblasts (human dermal fibroblasts; HDFs) were suspended in a general medium (Dulbecco's modified minimum essential medium; DMEM added with 10% FBS). This was seeded in a 24-well plate at a concentration of 1×10$^4$ cells/well (day 0), and culturing was started in 5% $CO_2$/95% humidified air at 37° C. The next day, the culture supernatant was removed by suction and, as described in the Figure, the general medium, a calcification induction medium, or a calcification induction medium added with each small molecule compound was added at 500 µL/well.

The calcification induction medium is DMEM added with 10% FBS, 50 µg/ml ascorbic acid, 10 mM β-glycerophosphate and 100 nM Dexamethasone.

The compounds added to the medium and the concentrations thereof are as follows.
I-BET151: 2 µM
Pifthrin-α: 5 µM
PD0325901: 2 µM
2-Me-5HT: 2 µM
CX4945: 2 µM
CHIR99021: 2 µM
Forskolin: 2 µM
DZnep: 50 nM
D4476: 2 µM
SB431542: 2 µM
ALK5 i II: 2 µM.

The culture medium was exchanged with a fresh one every 3-4 days, and culturing was performed until day 28.

On day 28, the culture medium was removed from each well by suction, washed with PBS(−), and fixed with 10% formalin. It was washed 3 times with sterile distilled water, Alizarin Red S staining solution was added, and the mixture was incubated at room temperature for 15 min. The staining solution after staining was recovered in a 96 well plate and used for the experiment of Example 30. Thereafter, the well was washed with sterile distilled water, and photographed.

The results are shown in FIG. 33.

Figure 34:
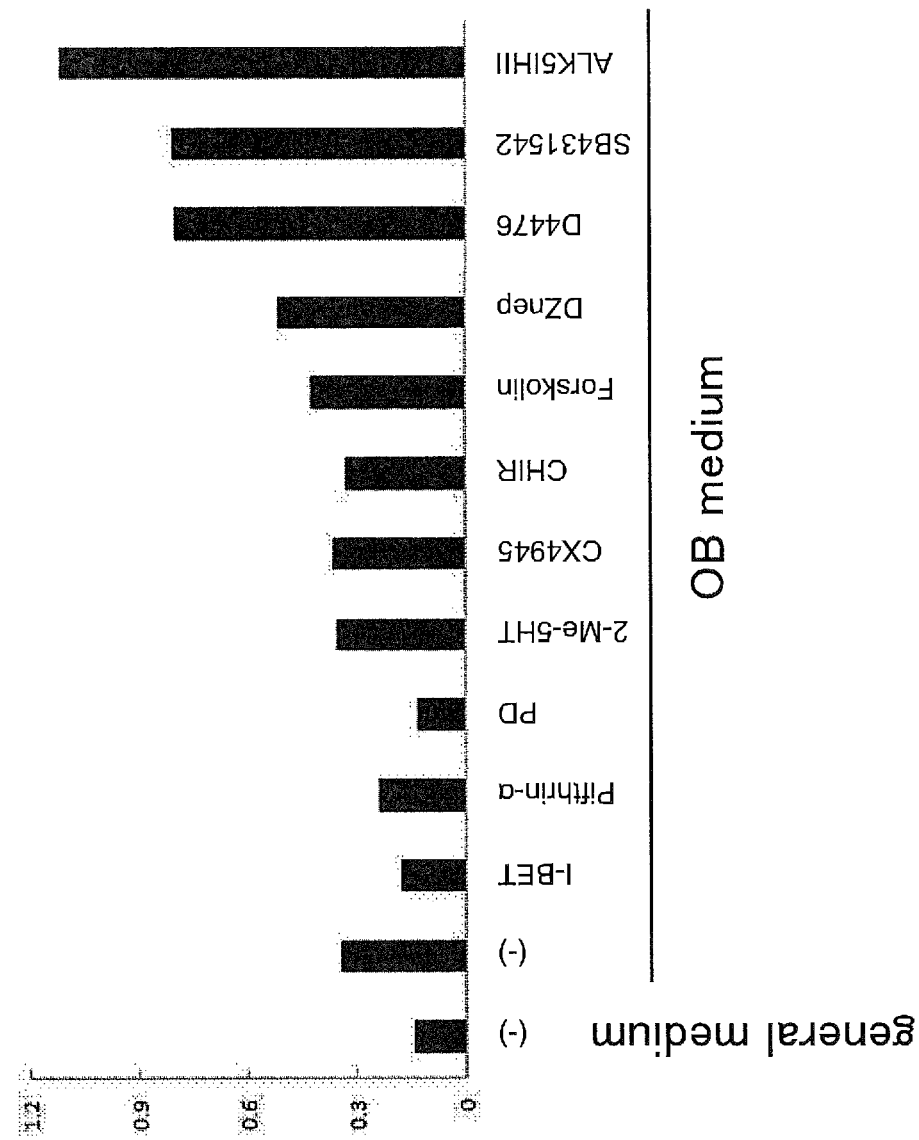
FIG. 34 shows the results of Alizarin Red S staining (absorbance measurement).

Example 30 (FIG. 34)

In the experiment of Example 29, the solution after staining with the Alizarin Red S staining solution was collected in a 96 well plate and the absorbance (OD 550 nm) was measured with an absorption spectrometer.

The results are shown in FIG. 34.

From the results shown in FIG. 33 and FIG. 34, it was found that the TGF-β pathway inhibitors D4476, SB431542 and ALK5 i II induce conversion from fibroblast to osteoblast when added to a calcification induction medium. However, it is clear that the compounds (I-BET, Pifthrin-α, PD0325901, 2-Me-5HT, CHIR, Forskolin and DZnep) other than the TGF-β pathway inhibitors reported to promote induction from fibroblast to iPS cell do not induce conversion from fibroblast to osteoblast when addition culture is performed under the same conditions as the TGF-β pathway inhibitor. Of the TGF-β pathway inhibitors, ALK5 i II most strongly induced conversion from fibroblast to osteoblast.

Figure 35:
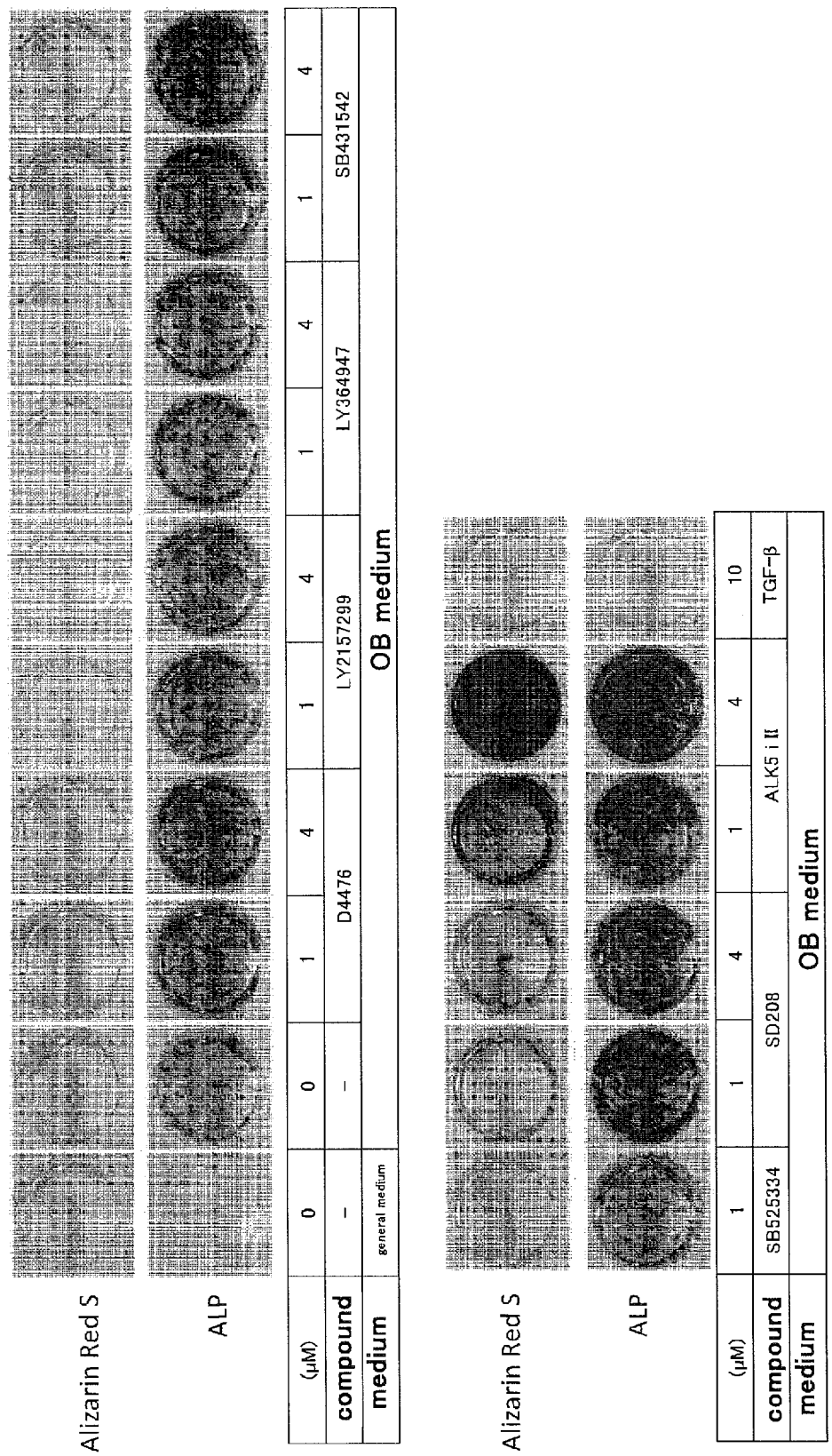
FIG. 35 shows the results of Alizarin Red S staining and ALP staining (staining Figure).

Example 31 (FIG. 35)

Human normal skin-derived fibroblasts (HDFs) were suspended in a general medium (DMEM added with 10% FBS). This was seeded in a 24-well plate at a concentration of 1×10$^4$ cells/well (day 0), and culturing was started in 5% $CO_2$/95% humidified air at 37° C. The next day, the culture supernatant was removed by suction and, as described in the Figure, the general medium, a calcification induction medium (OB medium), or a calcification induction medium added with each small molecule compound or cytokine was added at 500 µL/well.

The calcification induction medium is DMEM added with 10% FBS, 50 µg/ml ascorbic acid, 10 mM β-glycerophosphate and 100 nM Dexamethasone.

The compounds added to the medium and the concentrations thereof are as follows.
D4476: 1 or 4 µM
LY2157299: 1 or 4 µM
LY364947: 1 or 4 µM
SB431542: 1 or 4 µM
SB525334: 1 or 4 µM
SD208: 1 or 4 µM
ALK5 i II: 1 or 4 µM
TGF-β: 10 ng/ml.

The culture medium was exchanged with a fresh one every 3-4 days, and culturing was performed until day 21.

On day 21, the culture medium was removed from a part of the well, washed with PBS(−), and fixed with a fixative. It was washed 3 times with sterile distilled water. The well after ALP staining was washed with sterile distilled water, and photographed.

On day 21, the culture medium was removed from the rest of the well by suction, washed with PBS(−), and fixed with 10% formalin. It was washed 3 times with sterile distilled water, Alizarin Red S staining solution was added, and the mixture was incubated at room temperature for 15 min. The staining solution after staining was recovered in a 96 well plate, and used for the experiment of Example 32. Thereafter, the well was washed with sterile distilled water, and photographed.

The results are shown in FIG. 35.

Figure 36:
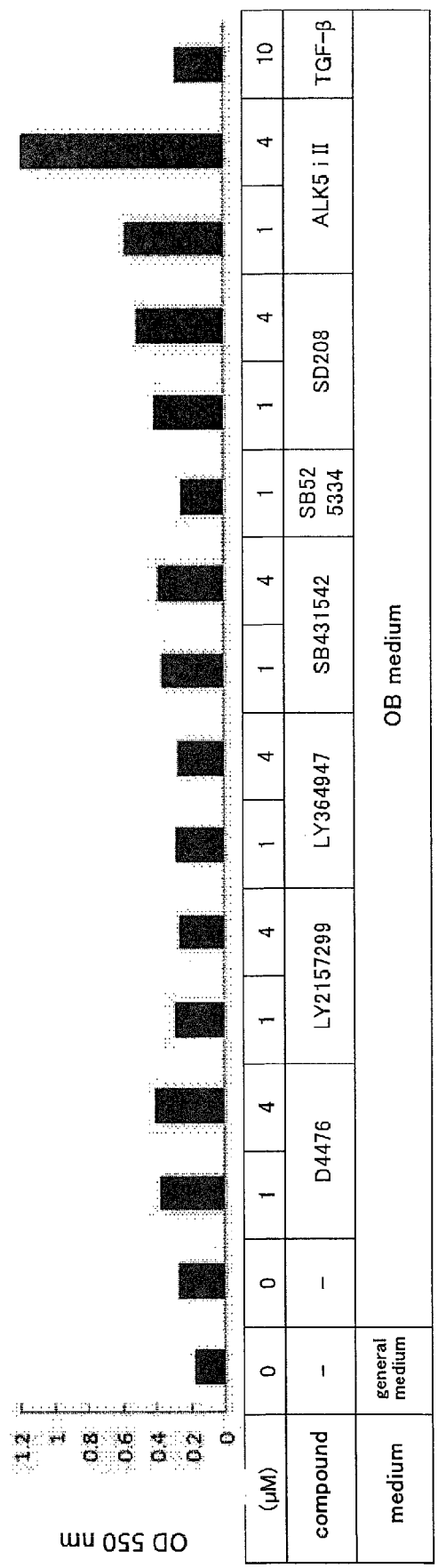
FIG. 36 shows the results of Alizarin Red S staining (absorbance measurement).

Example 32 (FIG. 36)

In the experiment of Example 31, the solution after staining with the Alizarin Red S staining solution was collected in a 96 well plate and the absorbance (OD 550 nm) was measured with an absorption spectrometer.

The results are shown in FIG. 36.

From the results shown in FIG. 35 and FIG. 36, it was found that culturing in a calcification induction medium added with various TGF-β pathway inhibitors can convert human fibroblast to osteoblast. Particularly, it was found that SD208 and ALK5 i II can strongly convert human fibroblast to osteoblast. Among others, it was found that ALK5 i II can most strongly convert human fibroblast to osteoblast.

When cultured in a calcification induction medium added with TGF-β, human fibroblast was not converted to osteoblast.

Figure 37:
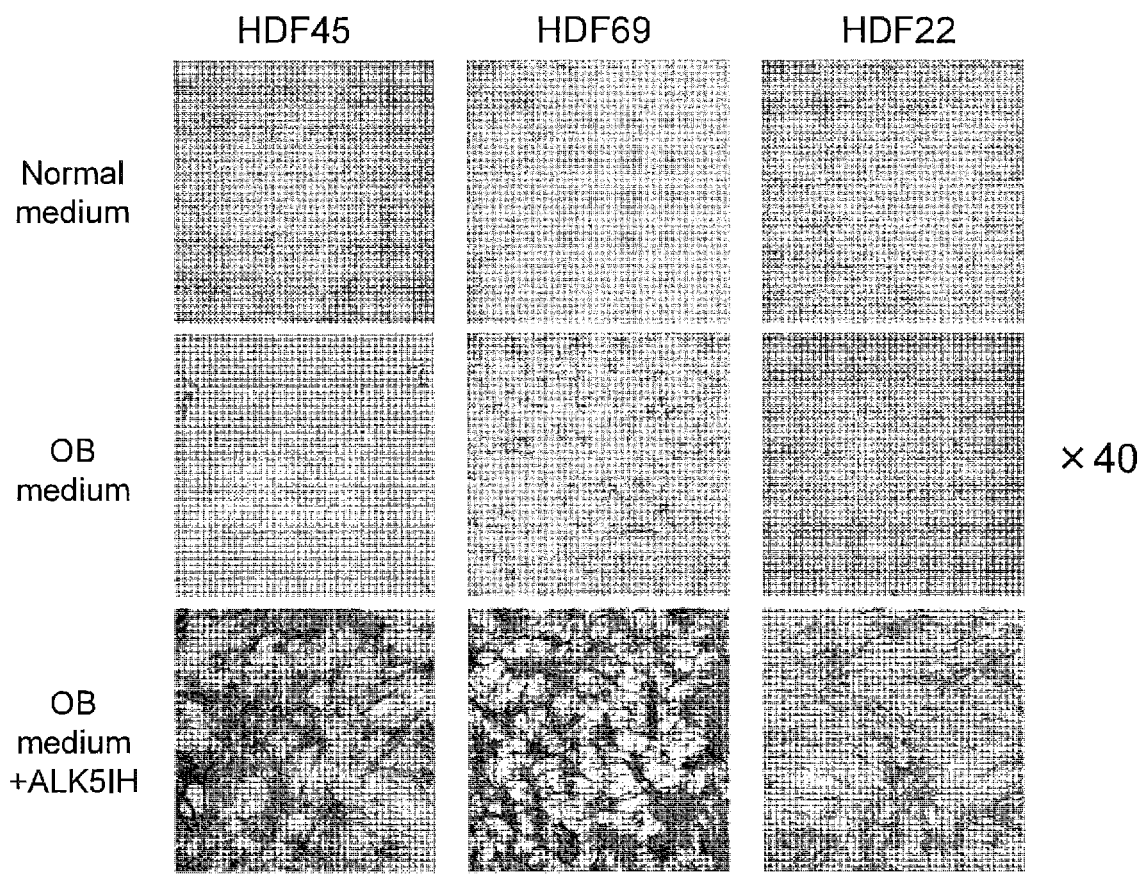
FIG. 37 shows the results of ALP staining (staining Figure).

Example 33 (FIG. 37)

Human normal skin-derived fibroblasts derived from various individuals (HDF45 (purchased from KURABO), HDF69 (purchased from PromoCell), HDF22 (purchased from PromoCell)) were suspended in the general medium (DMEM added with 10% FBS). This was seeded in a 24-well plate at a concentration of $1\times10^4$ cells/well (day 0), and culturing was started in 5% $CO_2$/95% humidified air at 37° C. The next day, the culture supernatant was removed by suction and, as described in the Figure, the general medium, a calcification induction medium, or a calcification induction medium added with 4 μM ALK5 i II was added at 500 μL/well.

The calcification induction medium is DMEM added with 10% FBS, 50 μg/ml ascorbic acid, 10 mM β-glycerophosphate and 100 nM Dexamethasone.

The culture medium was exchanged with a fresh one every 3-4 days, and culturing was performed until days 10, 15.

On day 10, the culture medium was removed from each well, washed with PBS(−), and fixed with a fixative. It was washed 3 times with sterile distilled water. After ALP staining, the well was washed with sterile distilled water, and photographed with an inverted microscope at ×40 magnification.

The results are shown in FIG. 37.

Figure 38:
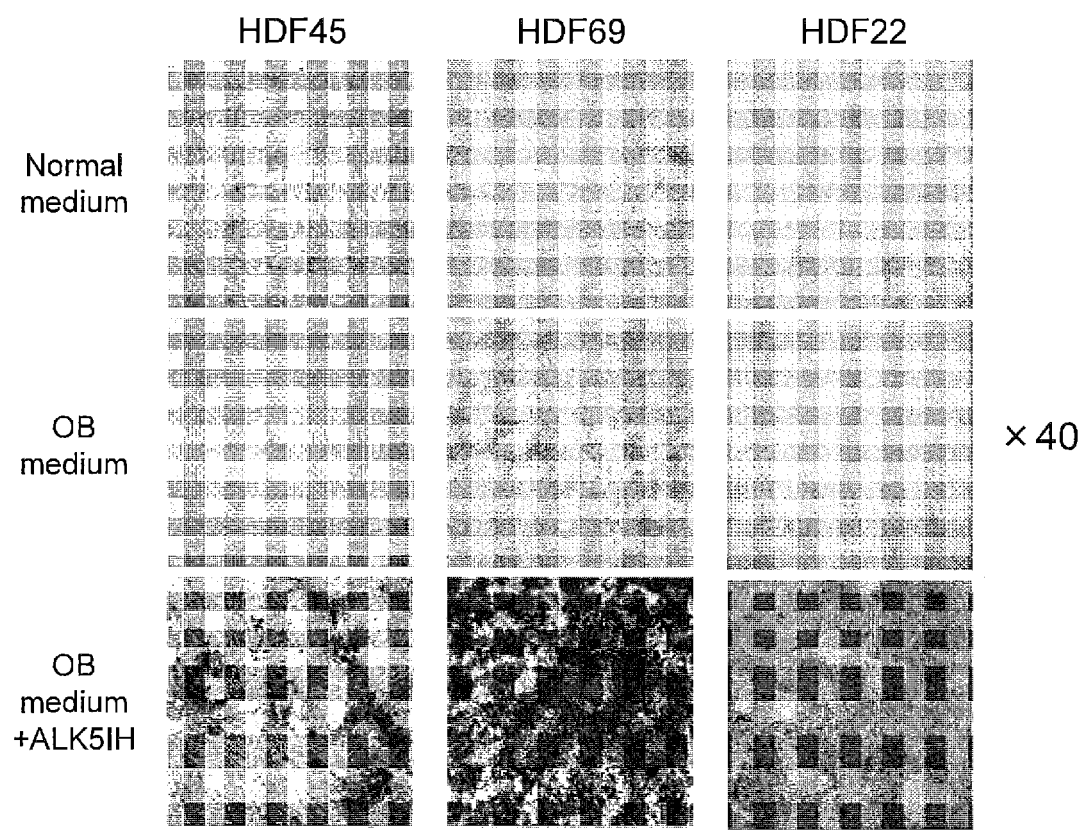
FIG. 38 shows the results of Alizarin Red S staining (staining Figure).

Example 34 (FIG. 38)

Culturing was performed in the same manner as in Example 33 by using human normal skin-derived fibroblasts derived from various individuals (HDF45, HDF69, HDF22).

On day 15, the culture medium was removed from each well by suction, washed with PBS(−), and fixed with 10% formalin. It was washed 3 times with sterile distilled water. After Alizarin Red S staining, the well was washed with sterile distilled water, and photographed with an inverted microscope at ×40 magnification.

The results are shown in FIG. 38.

From the results shown in FIG. 37 and FIG. 38, it was found that any human normal skin-derived fibroblasts derived from different individuals are converted to osteoblasts by culturing in a calcification induction medium added with ALK5 i II.

Figure 39:
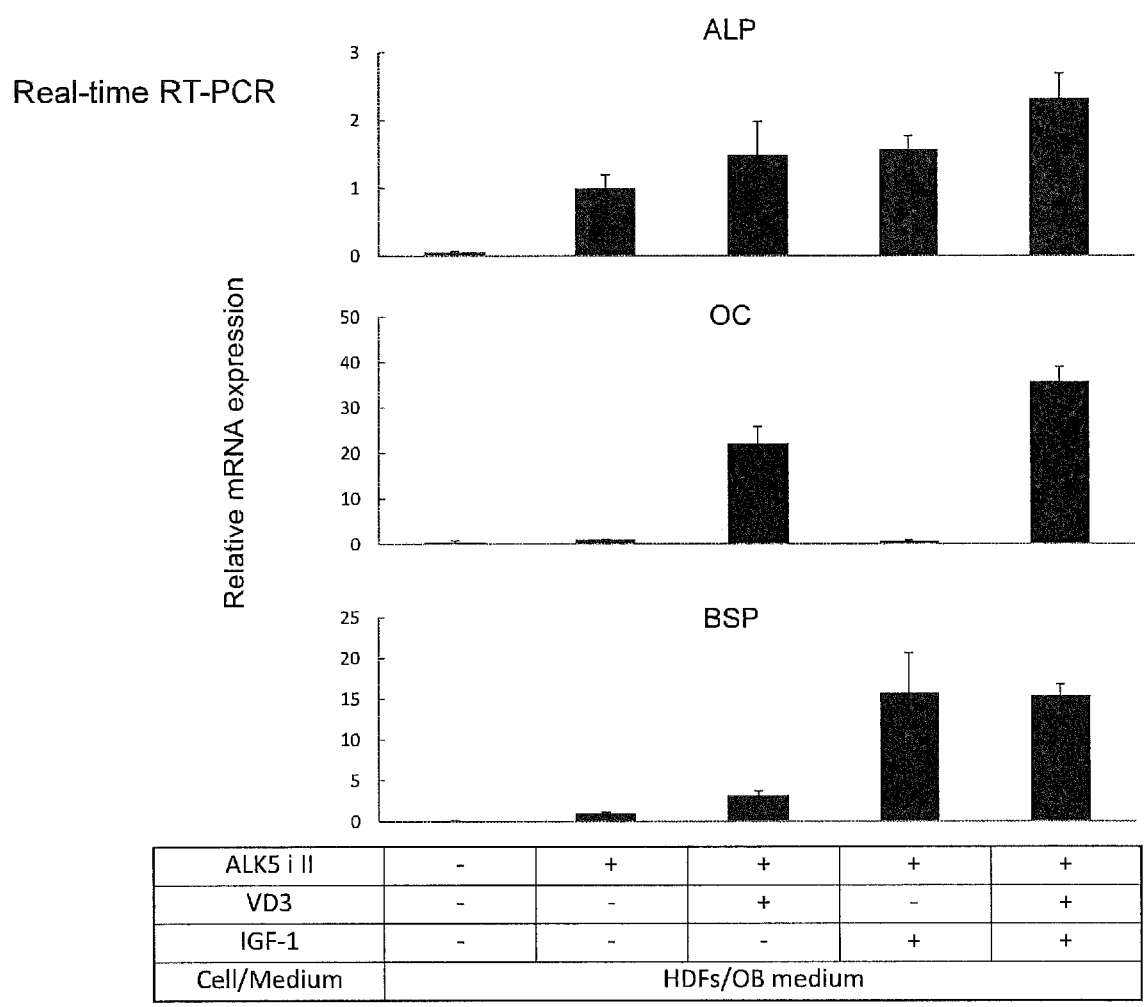
FIG. 39 shows the measurement results of a gene expression level by a real-time RT-PCR method.

Example 35 (FIG. 39)

Human normal skin-derived fibroblasts (HDFs) were suspended in the general medium (DMEM added with 10% FBS). This was seeded in a 24-well plate at a concentration of $1\times10^4$ cells/well (day 0), and culturing was started in 5% $CO_2$/95% humidified air at 37° C. The next day, the culture supernatant was removed by suction and, as described in the Figure, a calcification induction medium (OB medium), or a calcification induction medium added with each small molecule compound and/or cytokine was added at 500 μL/well.

The calcification induction medium is DMEM added with 10% FBS, 50 μg/ml ascorbic acid, 10 mM β-glycerophosphate and 100 nM Dexamethasone.

The concentrations of the small molecule compound or cytokine added are as follows.

ALK5 i II: 4 μM
1α,25-dihydroxy Vitamin D3 (VD3): 5 nM
Human insulin-like growth factor-1 (IGF-1): 100 ng/ml.

The culture medium was exchanged with a fresh one every 3-4 days, and culturing was performed until day 18.

On day 18, the culture medium was removed from each well by suction, washed with PBS, and total RNA was extracted from the cell with ISOGEN II. cDNA was synthesized from the RNA by using Rever Tra Ace qPCR RT Master Mix. This cDNA was admixed with Real-time PCR Master Mix, and primers specific to Alkaline Phosphatase, Osteocalcin, Bonesialoprotein or β-actin gene, and Taqman probe. qRT-PCR was performed using AB7300 Real-time PCR system. The mRNA level of Alkaline Phosphatase, Osteocalcin (OC), Bonesialoprotein gene was quantified as a ratio to β-actin gene mRNA level, and calculated with the value of fibroblast cultured in a calcification induction medium added with ALK5 i II as 1.

The results are shown in FIG. 39. The mRNA expression of ALP significantly increased in the cell cultured in a calcification induction medium added with ALK5 i II. The mRNA expression of OC increased in the cell cultured in a calcification induction medium added with ALK5 i II, as compared to the cell cultured in a calcification induction medium, and significantly increased in the cell cultured in a calcification induction medium added with ALK5 i II and VD3, as compared to the cell cultured in a calcification induction medium added with ALK5 i II. The mRNA expression of BSP increased in the cell cultured in a calcification induction medium added with ALK5 i II, as compared to the cell cultured in a calcification induction medium, and further significantly increased in the cell cultured in a calcification induction medium added with ALK5 i II and IGF-1, as compared to the cell cultured in a calcification induction medium added with ALK5 i II. The numerical value shows mean±S.D. (Values are means±S.D. (n=4)).

Figure 40:
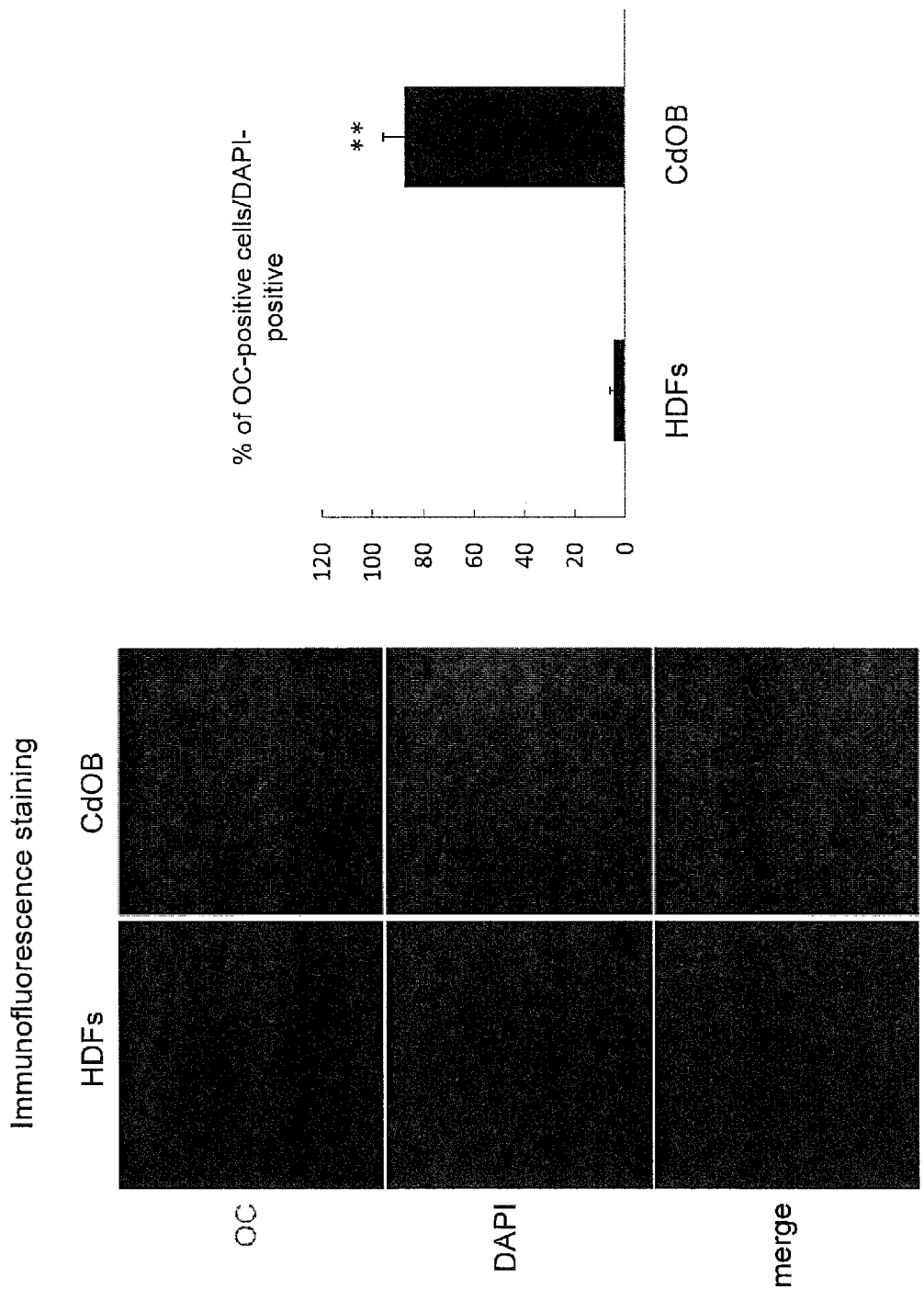
FIG. 40 shows the results of immunostaining of Osteocalsin (OC) (staining Figure and percentage of OC positive cells in DAPI positive cells).

Example 36 (FIG. 40)

Human normal skin-derived fibroblasts (HDFs) were suspended in the general medium (DMEM added with 10% FBS). This was seeded in a 24-well plate at a concentration of 1×10⁴ cells/well (day 0), and culturing was started in 5% $CO_2$/95% humidified air at 37° C. The next day, the culture supernatant was removed by suction and the general medium, or a calcification induction medium added with ALK5 i II, VD3, IGF-1 respectively at a concentration of 4 µM, 5 nM, 100 ng/ml was added at 500 µL/well.

The calcification induction medium is DMEM added with 10% FBS, 50 µg/ml ascorbic acid, 10 mM β-glycerophosphate and 100 nM Dexamethasone.

The culture medium was exchanged with a fresh one every 3-4 days, and culturing was performed until day 18.

On day 18, the culture medium was removed from each well by suction, and washed with PBS(−). After fixing with 4% para-formaldehyde, the cells were washed with PBS(−). After washing 3 times with PBS(−), Blocking One was added, and the mixture was incubated at room temperature for 60 min.

Anti-Osteocalcin antibody was added and the mixture was reacted at 4° C. overnight, and washed 3 times with Wash buffer. Alexa 488-conjugated anti-mouse Ig antibody was added and the mixture was reacted at room temperature for 1 hr and washed 3 times with Wash buffer. Using DAPI, nuclear staining was performed, and the cells were photographed with a fluorescence microscope at ×200 magnification. In addition, using BZ-H3C, BZ-H3CM (KEYENCE), OC positive cell number/DAPI number was calculated.

The results are shown in FIG. 40. In HDFs, a large number of cell nuclei were stained with DAPI, but few cells were markedly stained with anti-OC antibody. On the other hand, in CdOB, many cells were strongly stained with anti-OC antibody. By calculating the ratio of the number of cells stained with anti-OC antibody as a numerator and the number of cells with nucleus stained with DAPI as the denominator, it is clear that about 87% of human fibroblasts were converted to osteoblasts expressing osteocalcin protein. In the Figure,  shows p<0.01 relative to HDF (p<0.01 vs. the HDF).

Figure 41:
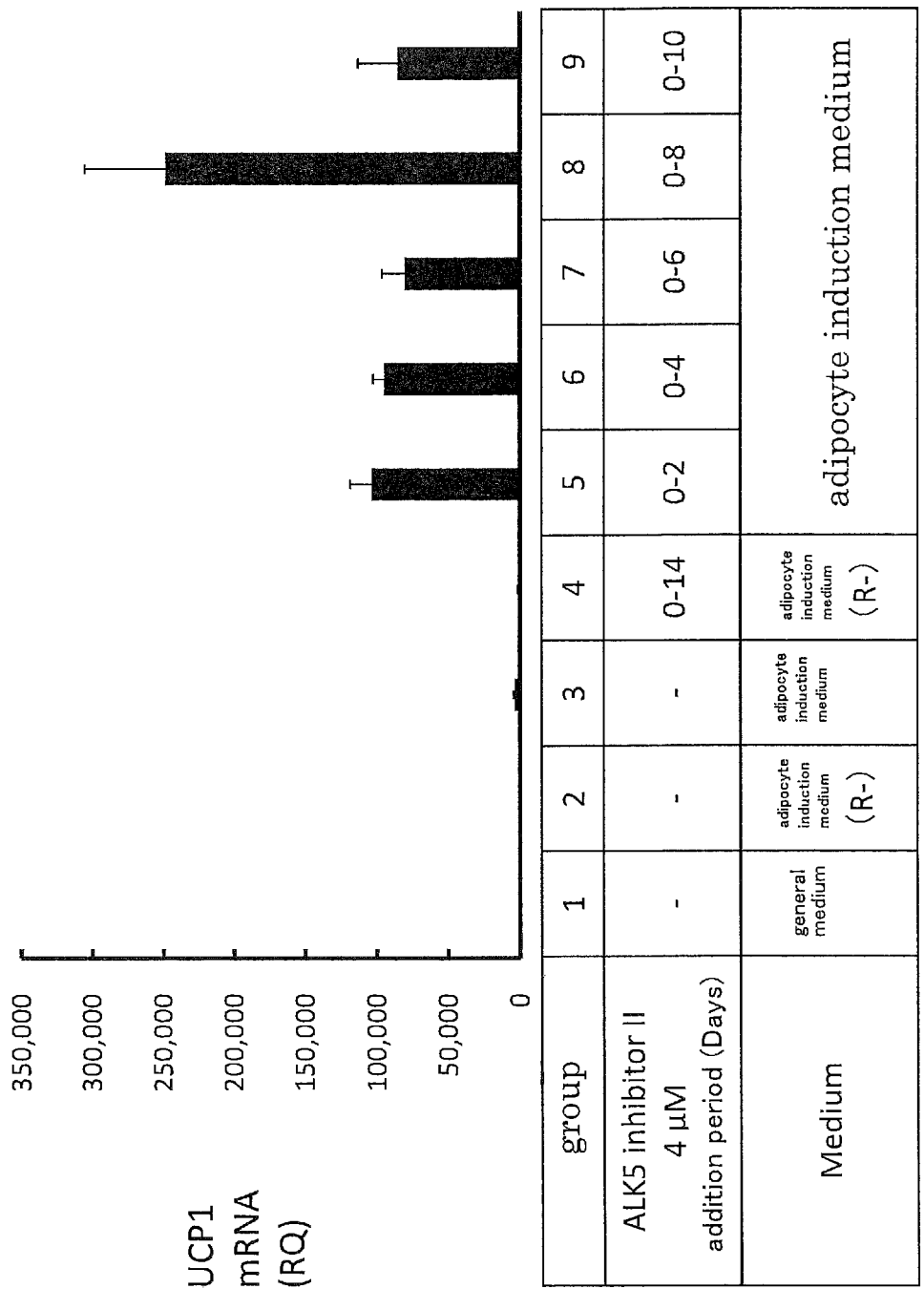
FIG. 41 shows the measurement results of a gene expression level by a real-time RT-PCR method.

Example 37 (FIG. 41)

Human normal skin-derived fibroblasts (human dermal fibroblasts; HDFs) were suspended in a general medium (Dulbecco's modified minimum essential medium; DMEM added with 10% FBS). This was seeded in a 12-well plate at a concentration of 3×10⁴ cells/well (day 0), and culturing was started in 5% $CO_2$/95% humidified air at 37° C. The next day, the culture supernatant was removed by suction and, as described in the Figure, the general medium was added to group 1 at 1 mL/well. An adipocyte induction medium free of Rosiglitazone (adipocyte induction medium (R−)) was added to group 2 at 1 mL/well. An adipocyte induction medium was added to group 3 at 1 mL/well. An adipocyte induction medium (R−) added with ALK5 inhibitor II at a concentration of 4 µM was added to group 4 at 1 mL/well. An adipocyte induction medium added with ALK5 inhibitor II at a concentration of 4 µM was added to groups 5-9 at 1 mL/well.

The adipocyte induction medium is DMEM added with 1 nM T3, 1 µM Rosiglitazone, 0.5 mM 3-isobutyl-1-methylxanthine (IBMX), 0.5 µM dexamethasone, 1 µg/mL Insulin and 10% FBS.

The adipocyte induction medium (R−) is DMEM added with 1 nM T3, 0.5 mM 3-isobutyl-1-methylxanthine (IBMX), 0.5 µM dexamethasone, 1 µg/mL Insulin and 10% FBS.

Once every 2 days, the culture medium was exchanged with a fresh one. In groups 5-9, as described in the Figure, the cells were cultured in an adipocyte induction medium added with ALK5 inhibitor II only in the period of days 0-2, 0-4, 0-6, 0-8, 0-10, and thereafter cultured in an adipocyte induction medium free of ALK5 inhibitor II. On day 14, the culture medium was removed by suction from each well, washed with PBS(−), and total RNA was extracted from the cells by using RNA easy Mini Kit manufactured by Qiagen. cDNA was synthesized from the RNA by using Rever Tra Ace qPCR RT Master Mix. This cDNA was admixed with Real-time PCR Master Mix, primers specific to UCP-1 gene or β actin gene and Taqman probe. qRT-PCR was performed using AB7300 Real-time PCR system. The mRNA level of UCP1 gene was quantified as a ratio to β-actin gene mRNA level, and calculated with the value of fibroblast cultured in the general medium as 1.

The results are shown in FIG. 41. It is clear that culturing in an adipocyte induction medium added with ALK5 inhibitor II converted fibroblast to brown adipocyte strongly expressing UCP1 gene. Particularly, it is clear that conversion of fibroblast to brown adipocyte can be more strongly induced by culturing in an adipocyte induction medium added with ALK5 inhibitor II for 0-8 days and thereafter culturing in an adipocyte induction medium free of ALK5 inhibitor II for 4 days.

Figure 42:
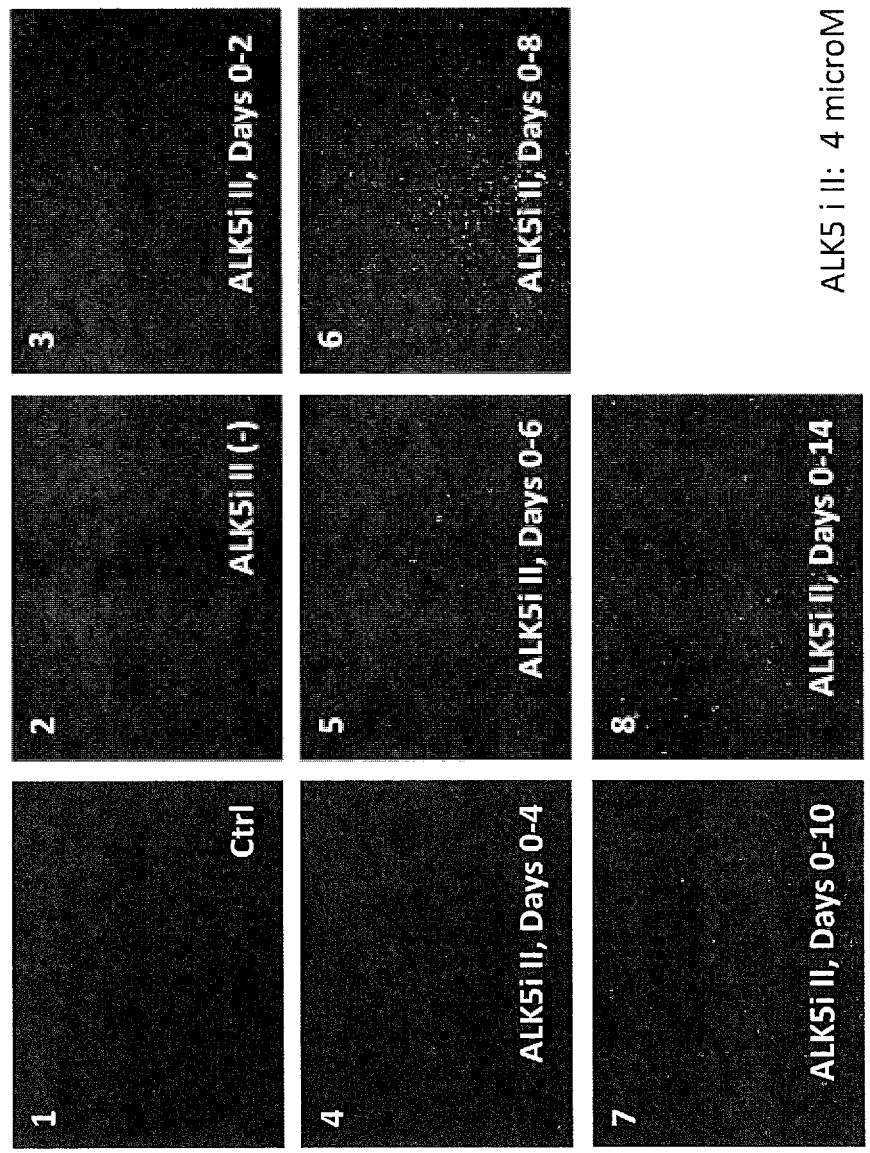
FIG. 42 shows the results of immunostaining of UCP1 (stained image).

Example 38 (FIG. 42)

Human normal skin-derived fibroblasts (HDFs) were suspended in a general medium (DMEM added with 10% FBS). This was seeded in a 12-well plate at a concentration of 3×10⁴ cells/well (day 0), and culturing was started in 5% $CO_2$/95% humidified air at 37° C. The next day, the culture supernatant was removed by suction and the general medium was added to group 1 at 1 mL/well (Control). An adipocyte induction medium was added to group 2 at 1 mL/well. An adipocyte induction medium added with ALK5 inhibitor II at a concentration of 4 µM was added to groups 3-8 at 1 mL/well.

The adipocyte induction medium is DMEM added with 1 nM T3, 1 µM Rosiglitazone, 0.5 mM 3-isobutyl-1-methylxanthine (IBMX), 0.5 µM dexamethasone, 1 µg/mL Insulin and 10% FBS. Once every 2 days, the culture medium was exchanged with a fresh one. In groups 3-7, as described in the Figure, the cells were cultured in an adipocyte induction medium added with ALK5 inhibitor II only in the period of days 0-2, 0-4, 0-6, 0-8, 0-10, and thereafter cultured in an adipocyte induction medium free of ALK5 inhibitor II. On day 14, the culture medium was removed by suction from each well, and washed with PBS(−). After fixing with 4% para-formaldehyde, the well was washed with PBS (−), Permanent wave Buffer (0.2% Triton-X-added PBS) was added and the well was incubated for 15 min. After washing 3 times with PBS(−), Blocking One was added, and the mixture was incubated at room temperature for 60 min. Anti-UCP-1 antibody (RD MAB6158) was added and the mixture was reacted for 2 hrs at room temperature, and washed 3 times with Wash buffer. CF488-conjugated anti-mouse Ig antibody (Biotum 20014) was added and the mixture was reacted for 2 hrs at room temperature, and washed 3 times with PBS(−). After nuclear staining with SlowFade Gold antifade reagent with DAPI manufactured by Lifetechnology, the cells were photographed with a fluorescence microscope at ×100 magnification.

Fluorescence microscopic images are shown in FIG. 42. The cells in group 1 and group 2 were hardly stained with anti-UCP1 antibody. In groups 3-8, many cells were stained with anti-UCP1 antibody. Particularly in group 6, the density of the cells stained with anti-UCP1 antibody was the highest. It is clear that culturing in an adipocyte induction medium added with ALK5 inhibitor II converted fibroblast to brown adipocyte is highly expressing UCP1 protein. Particularly, it is clear that conversion of fibroblast to brown adipocyte can be more strongly induced by culturing in an adipocyte induction medium added with ALK5 inhibitor II for 0-8 days and thereafter culturing in an adipocyte induction medium free of ALK5 inhibitor II for 4 days.

Figure 43:
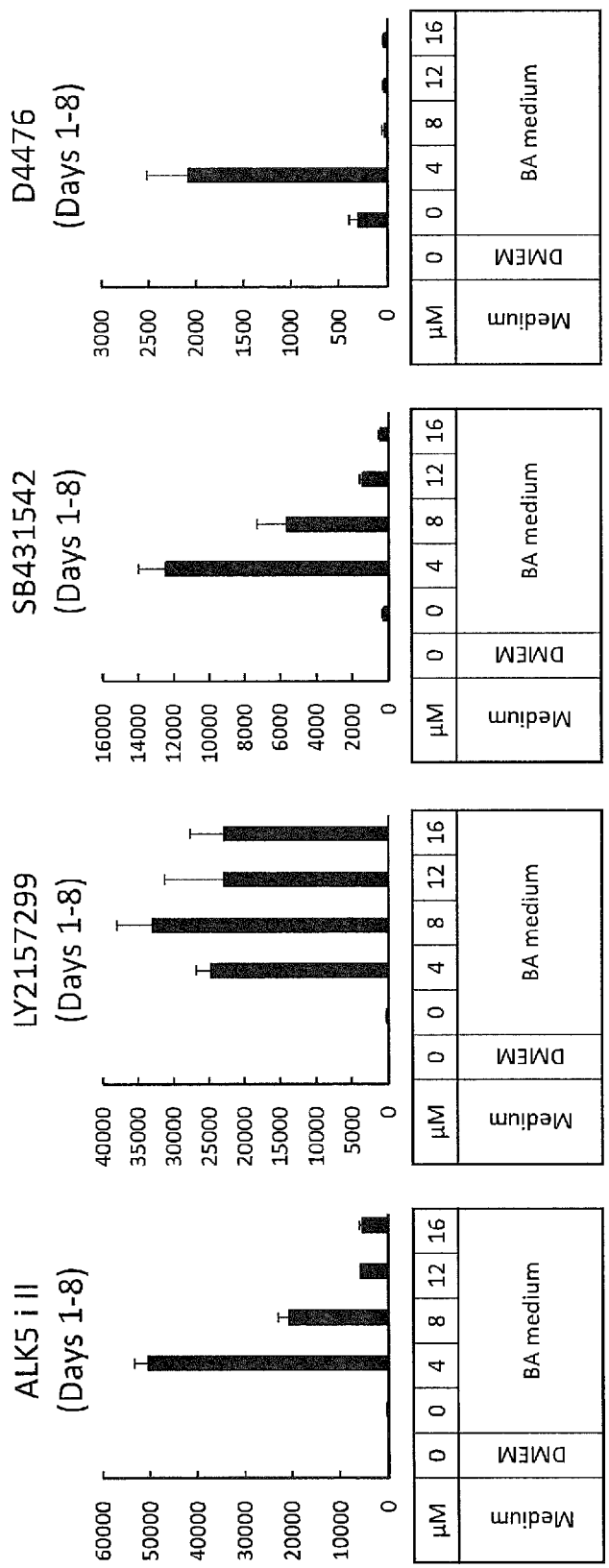
FIG. 43 shows the measurement results of a gene expression level by a real-time RT-PCR method.

Example 39 (FIG. 43)

Human normal skin-derived fibroblasts (HDFs) were suspended in a general medium (DMEM added with 10% FBS). This was seeded in a 12-well plate at a concentration of $3\times10^4$ cells/well (day 0), and culturing was started in 5% $CO_2$/95% humidified air at 37° C. The next day, the culture supernatant was removed by suction and the general medium, an adipocyte induction medium (BA medium), or an adipocyte induction medium added with compound ALK5 inhibitor II, LY2157299, SB431542, D4476 was added at 1 mL/well. The addition concentration of the compound was 4 µM, 8 µM, 12 µM or 16 µM. The adipocyte induction medium is DMEM added with 1 nM T3, 1 µM Rosiglitazone, 0.5 mM 3-isobutyl-1-methylxanthine (IBMX), 0.5 µM dexamethasone, 1 µg/mL Insulin and 10% FBS. Once every 2 days, the culture medium was exchanged with a fresh one, and culturing was performed from Day 1 to Day 8. Thereafter, in Day 9-Day 14, culturing was performed in a medium free of ALK5 inhibitor II, LY2157299, SB431542, D4476. On day 14, the culture medium was removed from each well by suction, and washed with PBS(-). Total RNA was extracted from the cells by using RNA easy Mini Kit manufactured by Qiagen. cDNA was synthesized from the RNA by using Rever Tra Ace qPCR RT Master Mix. This cDNA was admixed with Real-time PCR Master Mix, primers specific to UCP-1 gene or β actin gene and Taqman probe. qRT-PCR was performed using AB7300 Real-time PCR system. The mRNA level of UCP1 gene was quantified as a ratio to β-actin gene mRNA level, and calculated with the value of fibroblast cultured in the general medium as 1.

The results are shown in FIG. 43. It is clear that culturing in an adipocyte induction medium added with any of ALK5 inhibitor II, LY2157299, SB431541 and D4476 converted fibroblast to brown adipocyte strongly expressing UCP1 gene. Particularly, it is clear that conversion of fibroblast to brown adipocyte was most strongly induced by ALK5 inhibitor II and secondly by LY2157299.

Figure 44:
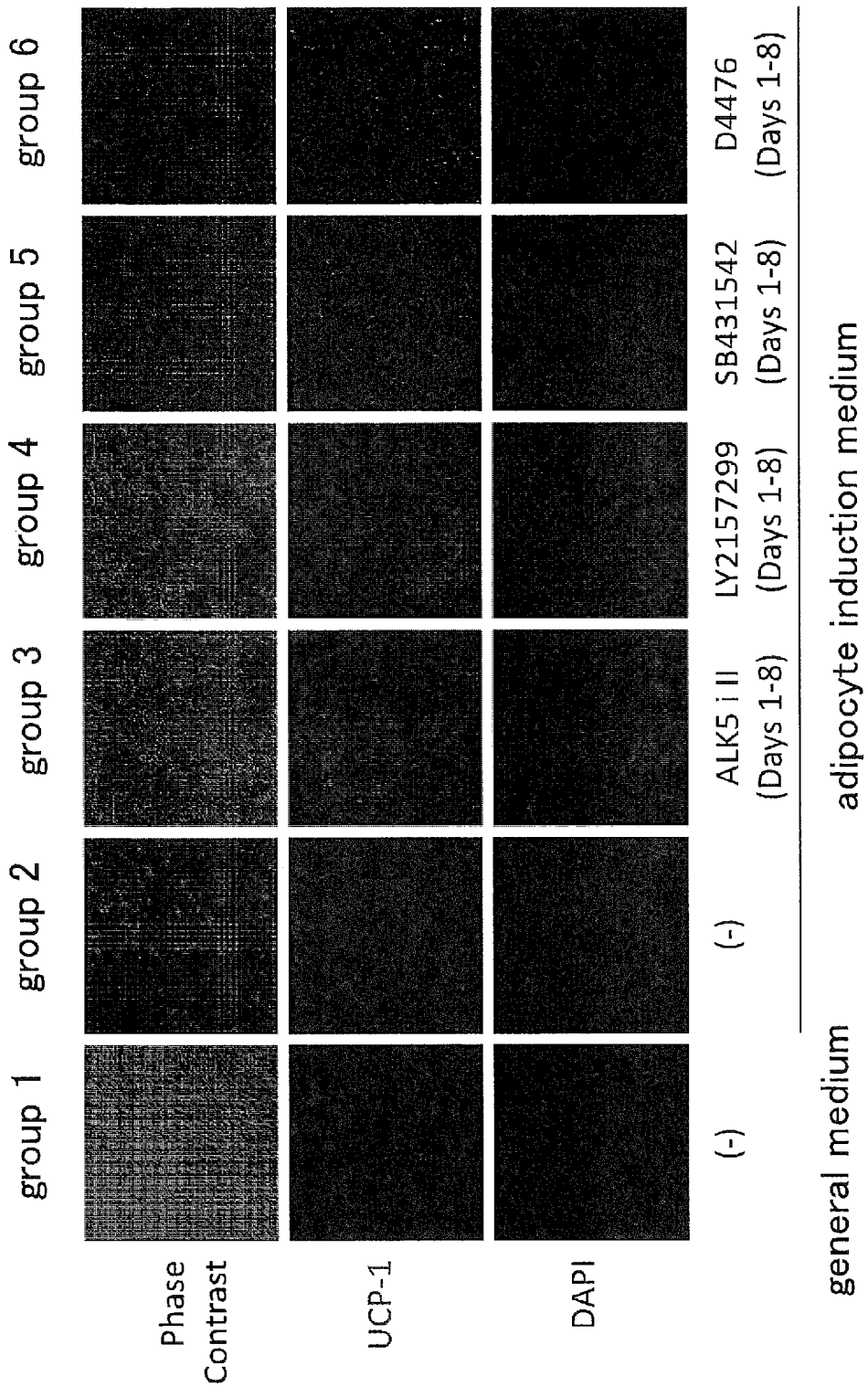
FIG. 44 shows the results of immunostaining of UCP1 (staining Figure).

Example 40 (FIG. 44)

Human normal skin-derived fibroblasts (HDFs) were suspended in a general medium (DMEM added with 10% FBS). This was seeded in a 12-well plate at a concentration of $3\times10^4$ cells/well (day 0), and culturing was started in 5% $CO_2$/95% humidified air at 37° C. The next day, the culture supernatant was removed by suction and, as described in the Figure, the general medium was added to group 1, an adipocyte induction medium was added to group 2 and an adipocyte induction medium respectively added with compound ALK5 inhibitor II (4 µM), LY2157299 (8 µM), SB431542 (4 µM), D4476 (4 µM) was added to groups 3-6 at 1 mL/well. The adipocyte induction medium is DMEM added with 1 nM T3, 1 µM Rosiglitazone, 0.5 mM 3-isobutyl-1-methylxanthine (IBMX), 0.5 µM dexamethasone, 1 µg/mL Insulin and 10% FBS. Once every 2 days, the culture medium was exchanged with a fresh one, and culturing was performed from Day 1 to Day 8. Thereafter, from Day 9 to Day 14, the cells were cultured in an adipocyte induction medium free of ALK5 inhibitor II, LY2157299, SB431542, D4476. On day 14, the culture medium was removed by suction from each well, and washed with PBS(-). After fixing with 4% para-formaldehyde, the well was washed with PBS (-), Permanent wave Buffer (0.2% Triton-X addition PBS) was added and the well was incubated for 15 min. After washing 3 times with PBS(-), Blocking One was added, and the mixture was incubated at room temperature for 60 min. Anti-UCP-1 antibody (RD MAB6158) was added and the mixture was reacted for 2 hrs at room temperature, and washed 3 times with Wash buffer. CF488-conjugated anti-mouse Ig antibody (Biotum 20014) was added and the mixture was reacted for 2 hrs at room temperature, and washed 3 times with PBS(-). After nuclear staining with SlowFade Gold antifade reagent with DAPI manufactured by Lifetechnology, the cells were photographed with a fluorescence microscope at ×100 magnification.

The results are shown in FIG. 44 (fluorescence microscopic images). In all groups, many nuclei were stained with DAPI. In group 1 and group 2, the cells were hardly stained with anti-UCP1 antibody. On the other hand, in groups 3-6, many cells were stained with anti-UCP1 antibody. Particularly in group 3, the density of the cells stained with anti-UCP1 antibody was the highest, and the second highest in group 4. Therefore, it is clear that culturing in an adipocyte induction medium added with any of ALK5 inhibitor II, LY2157299, SB431541 and D4476 converted fibroblast to brown adipocyte expressing UCP1 protein. Particularly, it is clear that conversion of fibroblast to brown adipocyte was most strongly induced by ALK5 inhibitor II and secondly by LY2157299.

Figure 45:
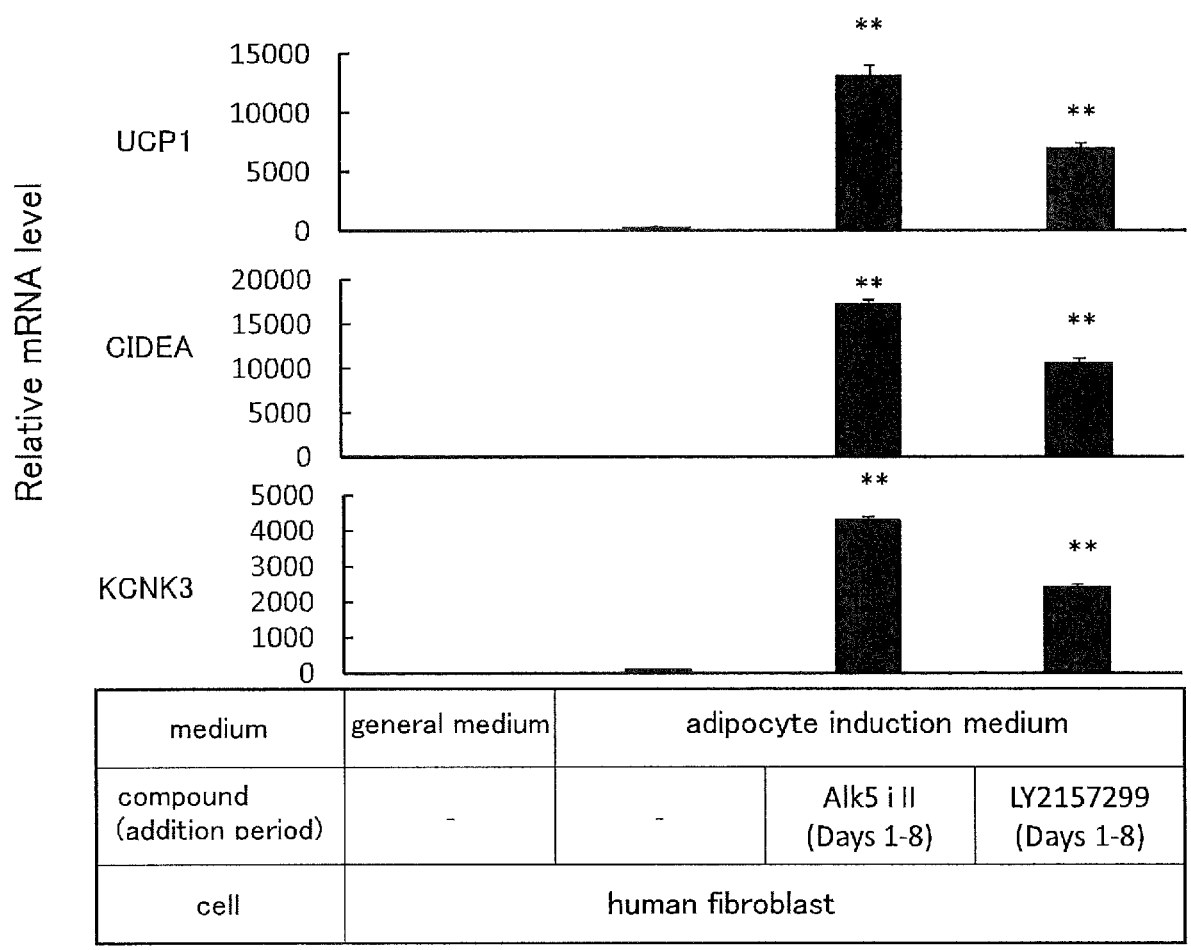
FIG. 45 shows the measurement results of a gene expression level by a real-time RT-PCR method.

Example 41 (FIG. 45)

Human normal skin-derived fibroblasts (HDFs) were suspended in a general medium (DMEM added with 10% FBS). This was seeded in a 12-well plate at a concentration of $3\times10^4$ cells/well (day 0), and culturing was started in 5% $CO_2$/95% humidified air at 37° C. The next day, the culture supernatant was removed by suction and the general medium, an adipocyte induction medium, or an adipocyte induction medium added with compound ALK5 inhibitor II (4 M) or LY2157299 (8 µM) was added at 1 mL/well. The adipocyte induction medium is DMEM added with 1 nM T3, 1 µM Rosiglitazone, 0.5 mM 3-isobutyl-1-methylxanthine (IBMX), 0.5 µM dexamethasone, 1 µg/mL Insulin and 10% FBS. Once every 2 days, the culture medium was exchanged with a fresh one, and culturing was performed from Day 1 to Day 8. Thereafter, from Day 9 to Day 14, the cells were cultured in an adipocyte induction medium free of ALK5 inhibitor II or LY2157299. On day 14, the culture medium was removed by suction from each well, washed with PBS(-) and total RNA was extracted from the cells by using RNA easy Mini Kit manufactured by Qiagen. cDNA was synthesized from the RNA by using Rever Tra Ace qPCR RT Master Mix. This cDNA was admixed with Real-time PCR Master Mix, primers specific to UCP-1 gene, CIDEA gene, KCNK3 gene or β actin gene and Taqman probe. qRT-PCR was performed using AB7300 Real-time PCR system. The mRNA level of UCP1 gene was quantified as a ratio to β-actin gene mRNA, and calculated with the value of fibroblast cultured in the general medium as 1.

The results are shown in FIG. 45. It is clear that culturing in an adipocyte induction medium added with any of ALK5 inhibitor II and LY2157299 converted fibroblast to brown adipocyte expressing UCP1 gene, CIDEA gene and KCNK3 gene. Particularly, it is clear that conversion of fibroblast to brown adipocyte was more strongly induced by ALK5 inhibitor II.

Figure 46:
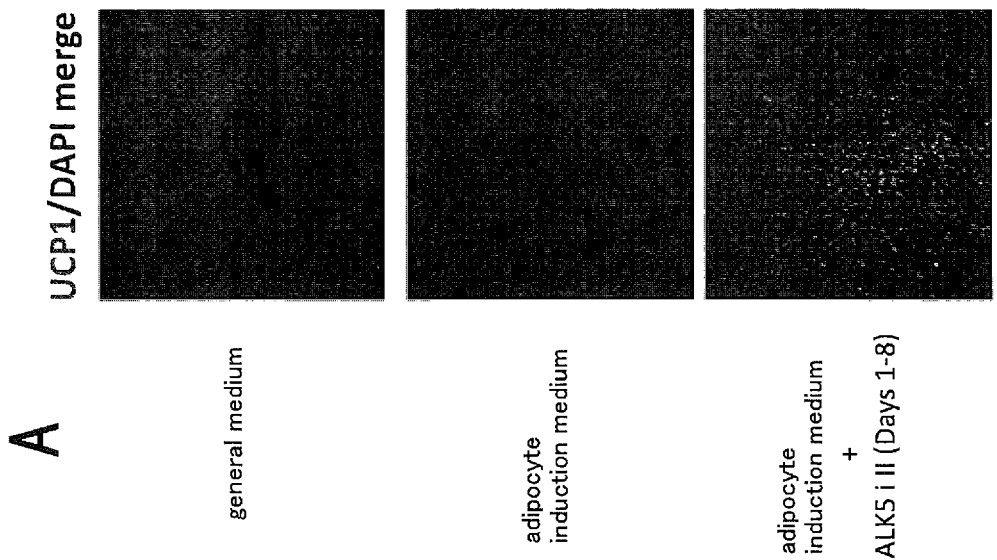
FIG. 46 shows the results of immunostaining of UCP1 (stained image (A) and percentage (B) of UCP1 positive cells in DAPI positive cells).

Example 42 (FIG. 46)

Human normal skin-derived fibroblasts (HDFs) were suspended in a general medium (DMEM added with 10% FBS). This was seeded in a 12-well plate at a concentration of $3\times10^4$ cells/well (day 0), and culturing was started in 5% $CO_2$/95% humidified air at 37° C. The next day, the culture supernatant was removed by suction and the general medium, an adipocyte induction medium, or an adipocyte induction medium added with ALK5 inhibitor II at a concentration of 4 µM was added at 1 mL/well. The adipocyte induction medium is DMEM added with 1 nM T3, 1 µM Rosiglitazone, 0.5 mM 3-isobutyl-1-methylxanthine (IBMX), 0.5 µM dexamethasone, 1 µg/mL Insulin and 10% FBS. Once every 2 days, the culture medium was exchanged with a fresh one, and culturing was performed from Day 1 to Day 8. Thereafter, from Day 9 to Day 14, the cells were cultured in an adipocyte induction medium free of ALK5 inhibitor II. On day 14, the culture medium was removed by suction from each well, and washed with PBS(-). After fixing with 4% para-formaldehyde, the well was washed with PBS (-), Perm Buffer (0.2% Triton-X-added PBS) was added and the well was incubated for 15 min. After washing 3 times with PBS(-), Blocking One was added, and the mixture was incubated at room temperature for 60 min. Anti-UCP-1 antibody (RD MAB6158) was added and the mixture was reacted for 2 hrs at room temperature, and washed 3 times with Wash buffer. CF488-conjugated anti-mouse Ig antibody (Biotum 20014) was added and the mixture was reacted for 2 hrs at room temperature, and washed 3 times with PBS(-). After nuclear staining with SlowFade Gold antifade reagent with DAPI manufactured by Lifetechnology, the cells were photographed with a fluorescence microscope at ×100 magnification. The percentage of UCP1 positive cells in DAPI positive cells was calculated using the Keyence BZ-H3A software for the photographed images.

The results are shown in FIG. 46. In HDFs cultured in the general medium and the cells cultured in an adipocyte induction medium free of ALK5 inhibitor II, many nuclei were stained with DAPI, but few cells were stained with anti-UCP1 antibody. On the other hand, in the cells cultured in an adipocyte induction medium added with ALK5 inhibitor II, many cells were strongly stained with anti-UCP1 antibody. By calculating the ratio of the number of cells stained with anti-UCP1 antibody as a numerator and the number of cells with nucleus stained with DAPI as the denominator, it is clear that more than 90% of fibroblasts were converted to brown adipocyte highly expressing UCP1 protein by culturing in an adipocyte induction medium added with ALK5 inhibitor II.

Figure 47:
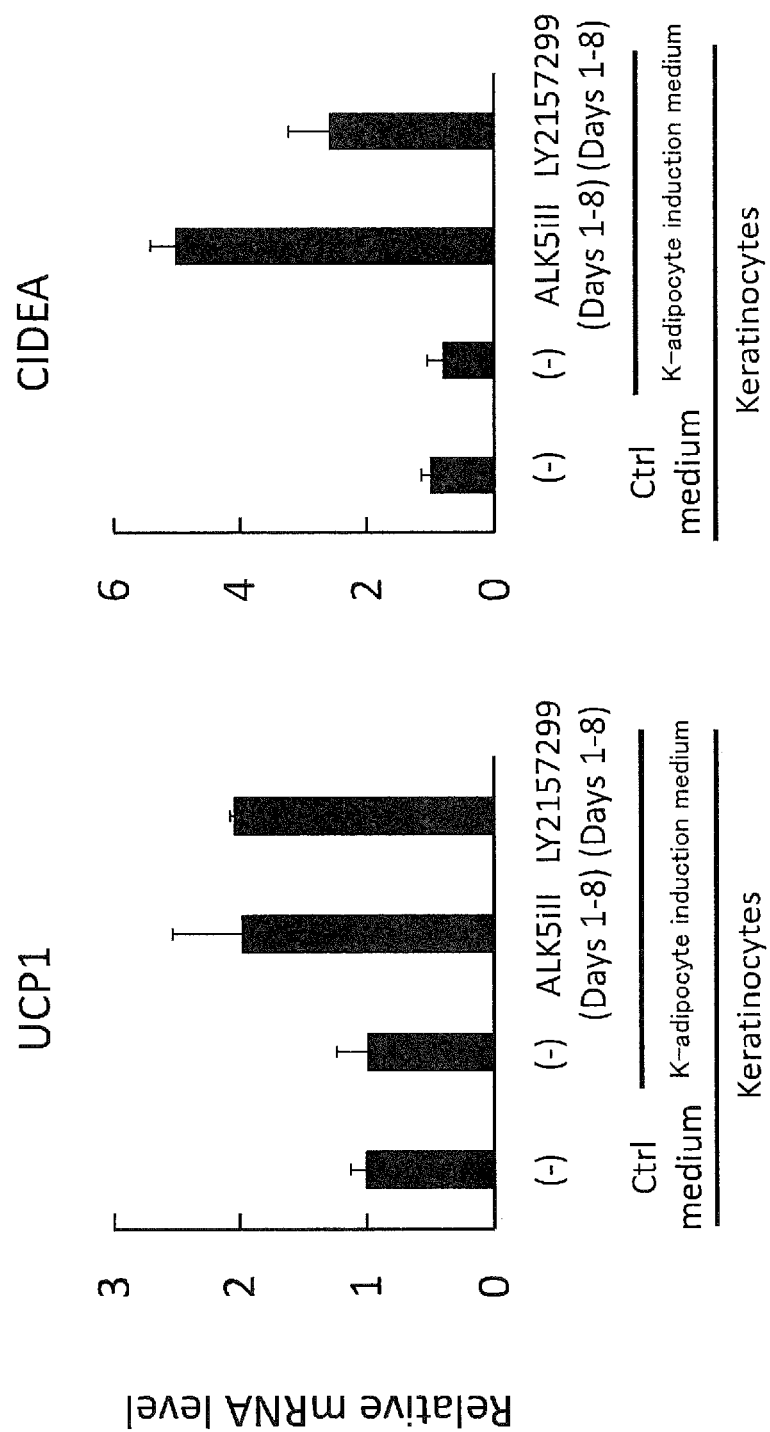
FIG. 47 shows the measurement results of a gene expression level by a real-time RT-PCR method.

Example 43 (FIG. 47)

Normal human epidermal keratinocyte (Human Epidermal Keratinocyte; NHEK (AD)) were suspended in a serum-free liquid medium for normal human epidermal keratinocyte proliferation (HuMedia-KG2; manufactured by Kurabo). This was seeded in a 12-well plate at a concentration of $3\times10^4$ cells/well (day 0), and culturing was started in 5% $CO_2$/95% humidified air at 37° C. The next day, the culture supernatant was removed by suction, and a HuMedia-KG2 medium (Ctrl medium), a K-adipocyte induction medium (adipocyte induction medium for keratinocyte) or a K-adipocyte induction medium added with ALK5 inhibitor II (4 µM) or LY2157299 (8 µM) was added at 1 mL/well.

The K-adipocyte induction medium is HuMedia-KG2 added with 1 nM T3, 1 µM Rosiglitazone, 0.5 mM 3-isobutyl-1-methylxanthine (IBMX), 0.5 µM dexamethasone, and 1 µg/mL Insulin.

Once every 2 days, the culture medium was exchanged with a fresh one, and culturing was performed from Day 1 to Day 8. Thereafter, from Day 9 to Day 14, the cells were cultured in a medium free of ALK5 inhibitor II or LY2157299. On day 14, the culture medium was removed by suction from each well, washed with PBS(-) and total RNA was extracted from the cells by using RNA easy Mini Kit manufactured by Qiagen. cDNA was synthesized from the RNA by using Rever Tra Ace qPCR RT Master Mix. This cDNA was admixed with Real-time PCR Master Mix, primers specific to UCP-1 gene, CIDEA gene or β actin gene and Taqman probe. qRT-PCR was performed using AB7300 Real-time PCR system. The mRNA level of UCP1 gene and CIDEA gene was quantified as a ratio to β-actin gene mRNA level, and calculated with the value of fibroblast cultured in the general medium as 1.

The results are shown in FIG. 47. It is clear that culturing in a K-adipocyte induction medium added with any of ALK5 inhibitor II and LY2157299 converted normal human epidermal keratinocyte to brown adipocyte expressing UCP1 gene and CIDEA gene.

Figure 48:
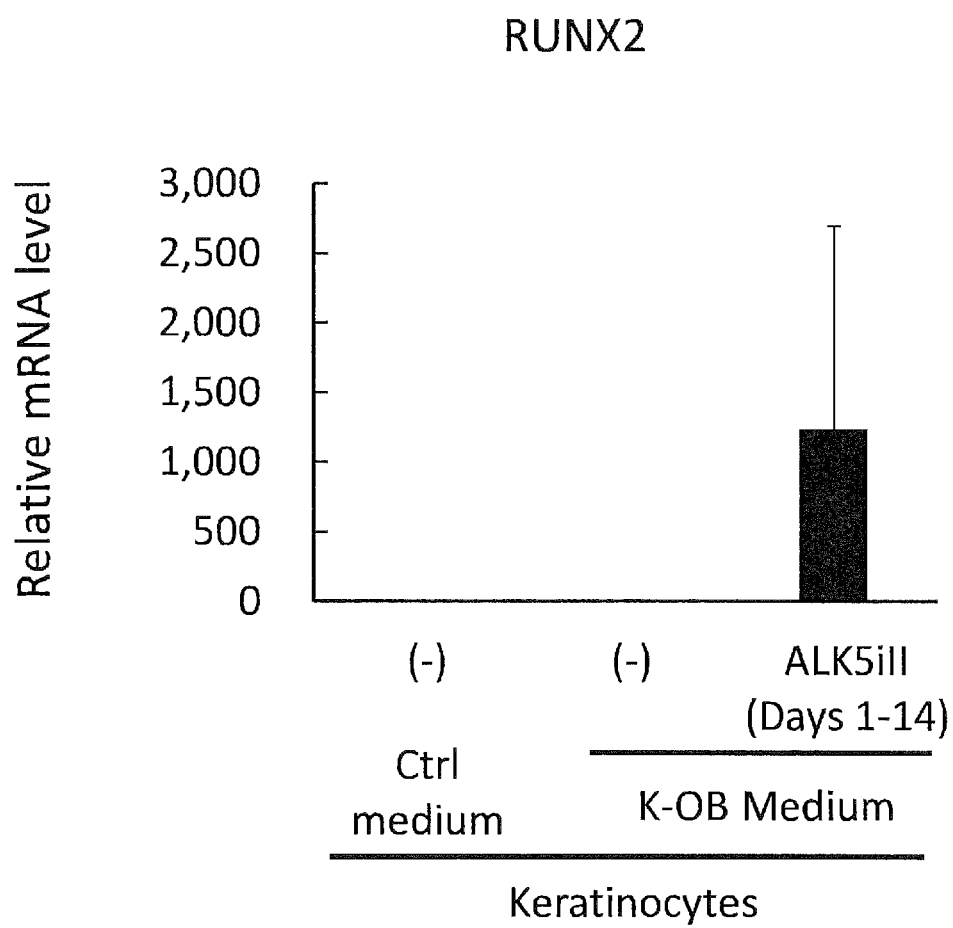
FIG. 48 shows the measurement results of a gene expression level by a real-time RT-PCR method.

Example 44 (FIG. 48)

Normal human epidermal keratinocyte (Human Epidermal Keratinocyte; NHEK (AD)) were suspended in a serum-free liquid medium for normal human epidermal keratinocyte proliferation (HuMedia-KG2; manufactured by Kurabo). This was seeded in a 12-well plate at a concentration of $3\times10^4$ cells/well (day 0), and culturing was started in 5% $CO_2$/95% humidified air at 37° C. The next day, the culture supernatant was removed by suction, and a HuMedia-KG2 medium (Ctrl medium), a K-osteoblast induction medium (osteoblast induction medium for keratinocyte) or a K-osteoblast induction medium added with compound ALK5 inhibitor II (4 µM) was added at 1 mL/well. The K-osteoblast induction medium is HuMedia-KG2 added with 50 Gg/mL ascorbic acid, 10 mM β-glycerol phosphate, and 100 nM dexamethasone. Once every 2 days, the culture medium was exchanged with a fresh one, and culturing was performed until Day 14. Thereafter, from Day 14 to Day 28, all cells were cultured in a medium free of ALK5 inhibitor II. On day 28, the culture medium was removed by suction from each well, washed with PBS(-) and total RNA was extracted from the cells by using RNA easy Mini Kit manufactured by Qiagen. cDNA was synthesized from the RNA by using Rever Tra Ace qPCR RT Master Mix. This cDNA was admixed with Real-time PCR Master Mix, primers specific to Runx2 gene or β actin gene and Taqman probe. qRT-PCR was performed using AB7300 Real-time PCR system. The mRNA level of Runx2 gene was quantified as a ratio to β-actin gene mRNA level, and calculated with the value of fibroblast cultured in the general medium as 1.

The results are shown in FIG. 48. It is clear that culturing in a K-osteoblast induction medium added with ALK5 inhibitor II converted normal human epidermal keratinocyte to osteoblast expressing Runx2 gene.

Figure 49:
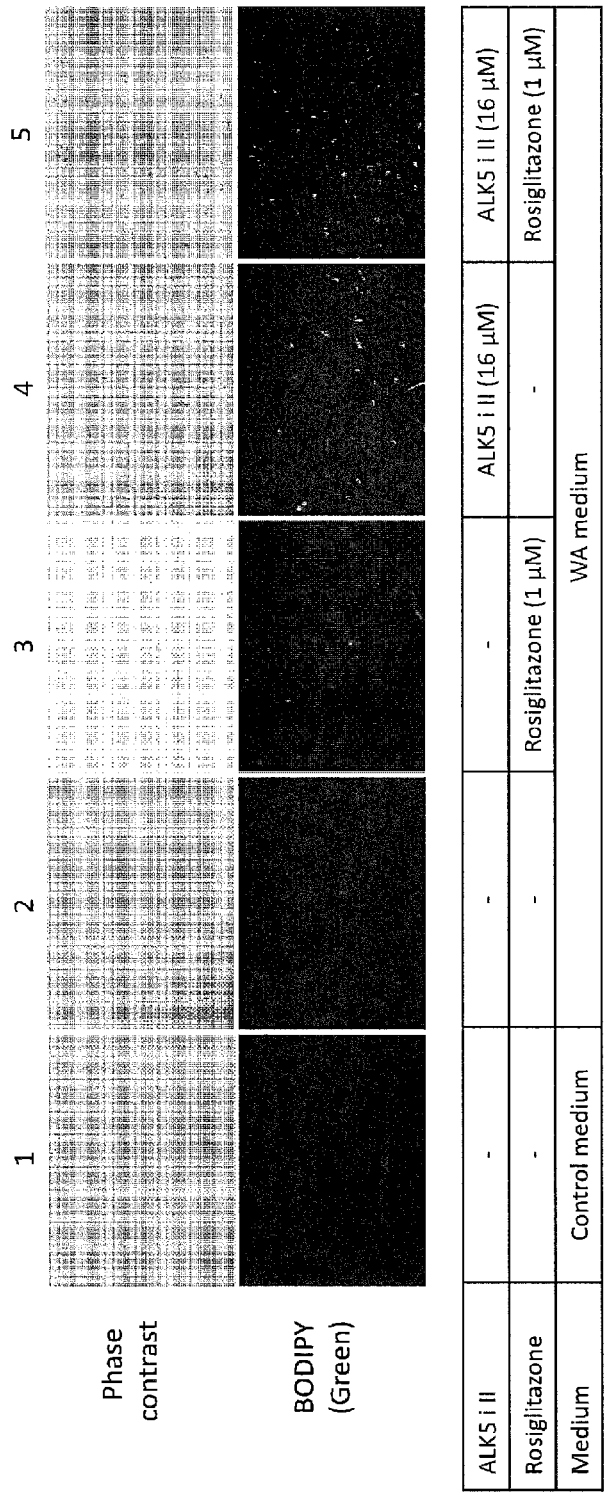
FIG. 49 shows the results of Bodipy staining (staining Figure).

Example 45 (FIG. 49)

Human normal skin-derived fibroblasts (human dermal fibroblasts; HDFs) were suspended in the Control medium. This was seeded in a 48-well plate at a concentration of $10^4$ cells/mm$^2$ (day 0), and culturing was started in 5% $CO_2$/95% humidified air at 37° C. On day 4, the culture supernatant was removed by suction and the wells were divided into 5 groups and the medium described in the Figure was added. That is,
 group 1: Control medium
 group 2: WA medium
 group 3: WA medium added with 1 µM Rosiglitazone
 group 4: WA medium added with 16 M ALK5 inhibitor II
 group 5: WA medium added with 16 µM ALK5 inhibitor II and 1 µM Rosiglitazone.

The composition of the medium is as follows. Control medium is Dulbecco's modified minimum essential medium; DMEM added with 10% FBS, 100 mM non-essential amino acids (NEAA), 100 U/ml penicillin, and 100 µg/mL streptomycin. WA medium is Dulbecco's modified minimum essential medium; DMEM added with 10% FBS, 100 mM non-essential amino acids (NEAA), 100 U/ml penicillin, 100 µg/mL streptomycin, 0.5 mM IBMX (3-isobutyl-1-methylxanthine), 62.5 nM Indomethacin, 1 µM Dexamethasone, and 170 nM Insulin.

Culturing was continued at 5% $CO_2$/95% humidified air, 37° C. On days 6, 8, 10, the medium was each exchanged with a fresh one having the same composition.

On day 12, Bodipy staining was performed as follows.
 (1) The culture medium in the well was removed, and each well was washed once with PBS.
 (2) 4% Formaldehyde solution (50 µL) was added to each well, and the mixture was fixed at room temperature overnight.
 (3) The well was washed twice with PBS.
 (4) Bodipy staining solution (50 µL) was added to each well, and the mixture was stood at room temperature for 30 min.
 (5) The staining solution was removed from the well and the well was stood at room temperature for 30 min.

Phase contrast images and green fluorescence images taken by a fluorescence microscope are shown in FIG. 49. Most of the cells cultured in Control medium are not stained by Bodipy and the group cultured in WA medium added with Rosiglitazone contains weakly-stained cells at low frequency. In the group cultured in a WA medium added with ALK5 inhibitor II, more cells are stained more strongly. In the group cultured in a WA medium added with both ALK5 inhibitor II and Rosiglitazone, the largest number of cells were strongly stained by BODIPY. Therefore, it is clear that culturing in a WA medium added with ALK5 inhibitor II converted human fibroblast to white adipocyte. Particularly, it is clear that ALK5 inhibitor II more strongly induced conversion of fibroblast to white adipocyte in the co-presence of Rosiglitazone.

Figure 50:
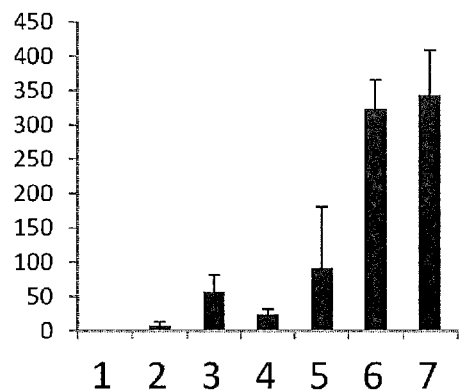
FIG. 50 shows the results of Bodipy staining (ratio of Bodipy positive cells).

Example 46 (FIG. 50)

Human normal skin-derived fibroblasts (human dermal fibroblasts; HDFs) were suspended in the Control medium. This was seeded in a 48-well plate at a concentration of $10^4$ cells/mm$^2$ (day 0), and culturing was started in 5% $CO_2$/95% humidified air at 37° C. On day 4, the culture supernatant was removed by suction and the wells were divided into 7 groups and the medium described in the Figure was added. That is,
 group 1: Control medium
 group 2: WA medium
 group 3: WA medium added with 1 µM Rosiglitazone
 group 4: WA medium added with 8 µM ALK5 inhibitor II
 group 5: WA medium added with 16 µM ALK5 inhibitor II
 group 6: WA medium added with 8 µM ALK5 inhibitor II and 1 µM Rosiglitazone
 group 7: WA medium added with 16 µM ALK5 inhibitor II and 1 µM Rosiglitazone The composition of the medium is the same as in Example 45.

Culturing was continued at 5% $CO_2$/95% humidified air, 37° C. On days 6, 8, 10, the medium was each exchanged with a fresh one having the same composition.

On day 12, in the same manner as in Example 45, the cells were stained with BODIPY, and lipid droplets were fluorescent stained, and photographed with a fluorescence microscope BZ-9000 (Keyence) at ×100 magnification. The number of BODIPY positive cells was calculated using BZ-II Analyzer software (Keyence, Osaka, Japan) and comparison was made between respective groups.

The results (mean±standard deviation) are shown in FIG. 50. Most of the cells cultured in Control medium were not stained by Bodipy but the group cultured in WA medium added with any of 1 µM Rosiglitazone and 16 µM ALK5 inhibitor II contained stained cells at low frequency. In the group cultured in a WA medium co-added with 8 µM or 16 µM ALK5 inhibitor II and 1 µM Rosiglitazone, more cells were stained. Therefore, it is clear that culturing in a WA medium added with ALK5 inhibitor II converted human fibroblast to white adipocyte. Particularly, it is clear that ALK5 inhibitor II more strongly induced conversion of fibroblast to white adipocyte in the co-presence of Rosiglitazone.

Figure 51:
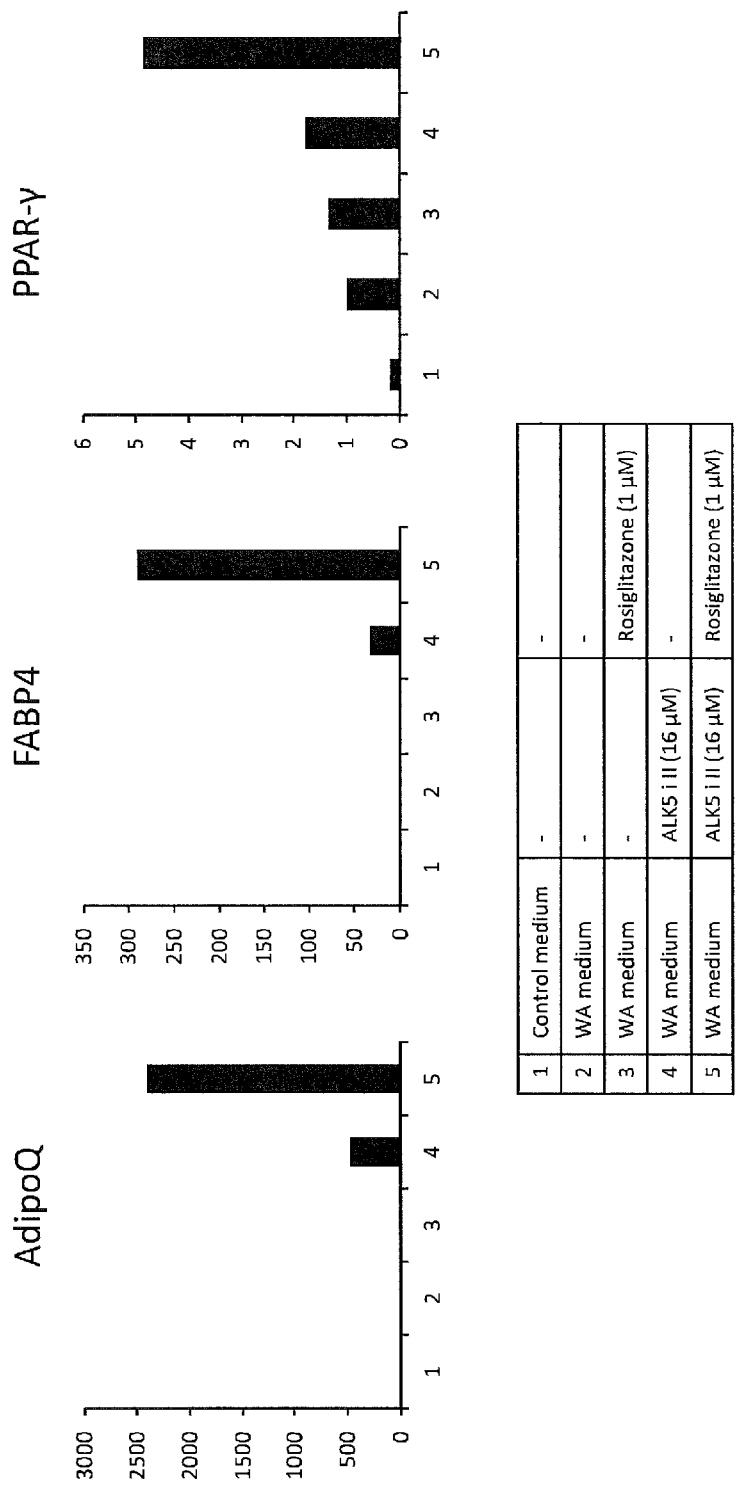
FIG. 51 shows the measurement results of a gene expression level by a real-time RT-PCR method.

Example 47 (FIG. 51)

Human normal skin-derived fibroblasts (human dermal fibroblasts; HDFs) were suspended in the Control medium. This was seeded in a 6-well plate at a concentration of $10^4$ cells/mm$^2$ (day 0), and culturing was started in 5% $CO_2$/95% humidified air at 37° C. On day 4, the culture supernatant was removed by suction and the wells were divided into 5 groups and, in the same manner as in Example 45, the medium described in the Figure was added. The composition of the medium is the same as in Example 45.

Culturing was continued at 5% $CO_2$/95% humidified air, 37° C. On days 6, 8, 10, the medium was each exchanged with a fresh one having the same composition.

On day 12, RNA was recovered from the cells. Real-time PCR was performed using TaqMan probes and Primers respectively specific to AdipoQ, FABP4 (mature adipocyte marker), and PPAR-γ (preadipocyte marker) gene, and mRNA was quantified.

The results (mean) (relative value) are shown in FIG. 51. AdipoQ and FABP4 were mildly induced to express by culturing with addition of ALK 5 i II alone and strongly induced to express by culturing with co-addition of ALK5 i II and Rosiglitazone. PPAR-γ was also mildly induced to express by culturing in WA medium, moderately induced to express by the addition of any of ALK5 i II and Rosiglitazone and strongly induced to express by the co-addition of ALK5 i II and Rosiglitazone.

Therefore, it is clear that culturing in a WA medium added with ALK5 inhibitor II converted human fibroblast to white adipocyte. Particularly, it is clear that ALK5 inhibitor II more strongly induced conversion of fibroblast to white adipocyte in the co-presence of Rosiglitazone.

Figure 52:
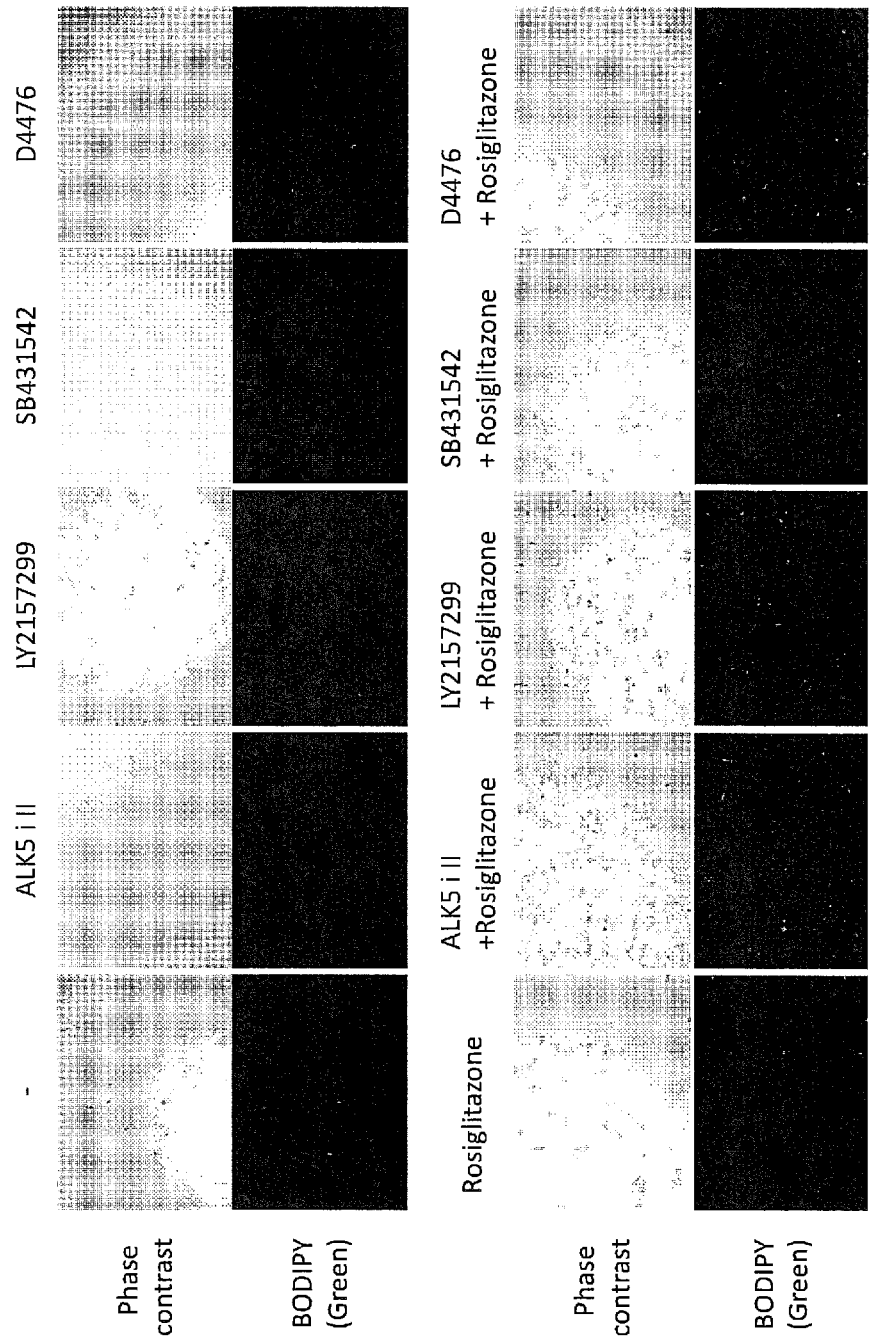
FIG. 52 shows the results of Bodipy staining (staining Figure).

Example 48 (FIG. 52)

Human normal skin-derived fibroblasts (human dermal fibroblasts; HDFs) were suspended in the Control medium. This was seeded in a 48-well plate at a concentration of $10^4$ cells/mm$^2$ (day 0), and culturing was started in 5% $CO_2$/95% humidified air at 37° C. On day 4, the culture supernatant was removed by suction and the wells were divided into 10 groups and the medium described in the Figure was added. That is,
  group 1: WA medium
  group 2: WA medium added with 16 µM ALK5 inhibitor II (ALK5 i II)
  group 3: WA medium added with 16 µM LY2157299
  group 4: WA medium added with 16 µM SB431542
  group 5: WA medium added with 16 µM D4476
  group 6: WA medium added with 1 µM Rosiglitazone
  group 7: WA medium added with 16 µM ALK5 inhibitor II (ALK5 i II) and 1 µM Rosiglitazone
  group 8: WA medium added with 16 µM LY2157299 and 1 M Rosiglitazone
  group 9: WA medium added with 16 µM SB431542 and 1 µM Rosiglitazone
  group 10: WA medium added with 16 µM D4476 and 1 µM Rosiglitazone The composition of the medium is the same as in Example 45.

Culturing was continued at 5% $CO_2$/95% humidified air, 37° C. On days 6, 8, 10, the medium was each exchanged with a fresh one having the same composition.

On day 12, in the same manner as in Example 45, the cells were stained with BODIPY, and lipid droplets were fluorescent stained and photographed with a fluorescence microscope BZ-9000 (Keyence) at ×100 magnification. The adipocyte number was calculated using BZ-II Analyzer software (Keyence, Osaka, Japan) and compared between respective groups. The results are shown in FIG. 52.

In the cells cultured in WA medium added with ALK5 inhibitor II, LY2157299, SB431542 or D4476 alone, only a few cells contained lipid droplets stained with Bodipy. However, in the group cultured in WA medium added with any of ALK5 inhibitor II, LY2157299, SB431542 and D4476, and Rosiglitazone, many cells were stained. Therefore, it is clear that culturing in a WA medium added with TGF-β pathway inhibitor converts human fibroblast to white adipocyte. In addition, it is clear that culturing in a WA medium added with both TGF-β pathway inhibitor and Rosiglitazone converted human fibroblast to white adipocyte more efficiently than with TGF-β pathway inhibitor alone. Particularly, it is clear that ALK5 inhibitor II among the TGF-β pathway inhibitors most strongly induced conversion of fibroblast to white adipocyte.

Figure 53:
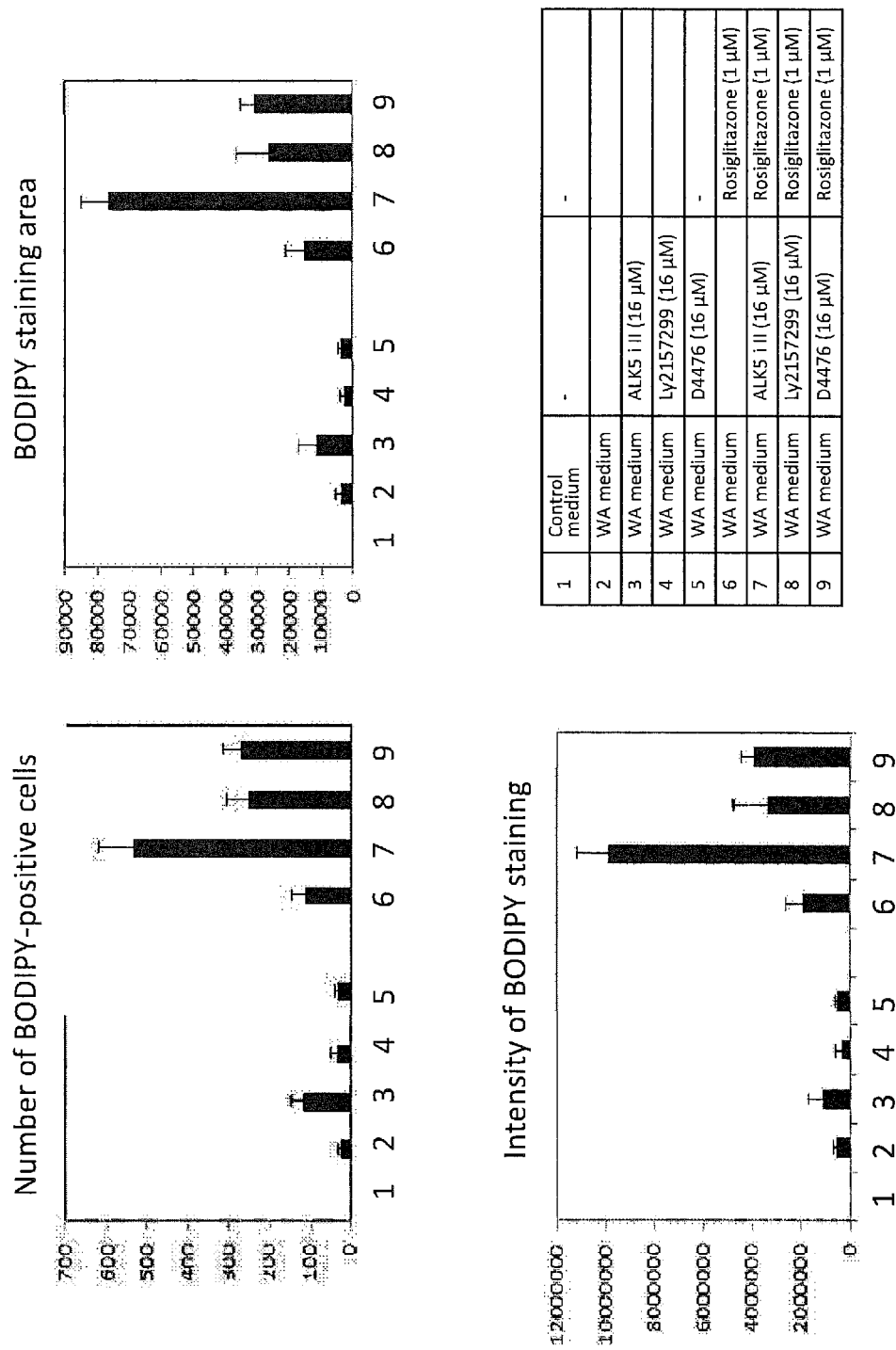
FIG. 53 shows the results of Bodipy staining (quantification).

Example 49 (FIG. 53)

Human normal skin-derived fibroblasts (human dermal fibroblasts; HDFs) were suspended in the Control medium. This was seeded in a 6-well plate at a concentration of $10^4$ cells/mm$^2$ (day 0), and culturing was started in 5% $CO_2$/95% humidified air at 37° C. On day 4, the culture supernatant was removed by suction and the wells were divided into 10 groups and, in the same manner as in Example 48, the medium described in the Figure was added. The composition of the medium is the same as in Example 45.

Culturing was continued at 5% $CO_2$/95% humidified air, 37° C. On days 6, 8, 10, the medium was each exchanged with a fresh one having the same composition.

On day 12, in the same manner as in Example 48, the cells were stained with BODIPY, and lipid droplets were fluorescent stained and photographed with a fluorescence microscope BZ-9000 (Keyence) at ×100 magnification. The number of BODIPY positive cells, area stained with BODIPY, and intensity of staining with BODIPY were calculated using BZ-II Analyzer software (Keyence, Osaka, Japan), and comparison was made between respective groups.

The results (mean±standard deviation) are shown in FIG. 53. The cells cultured in Control medium were hardly stained with BODIPY, but the cell cultured in a WA medium added with any of 1 µM Rosiglitazone and 16 µM ALK5 inhibitor II showed accumulation of a small amount of fat. By co-addition of Rosiglitazone, all of 16 µM ALK5 inhibitor II, LY2157299, SB431542 and D4476 more strongly induced fat accumulation than by the addition of Rosiglitazone alone. In the group cultured in a WA medium co-added with ALK5 inhibitor II and Rosiglitazone, a cell accumulating the largest amount of fat was found. Therefore, it is clear that human fibroblast was efficiently converted to white adipocyte by culturing in a WA medium added with TGF-β pathway inhibitor and Rosiglitazone. Particularly, it is clear that ALK5 inhibitor II among the TGF-β pathway inhibitors most strongly induced conversion of fibroblast to white adipocyte.

Figure 54:
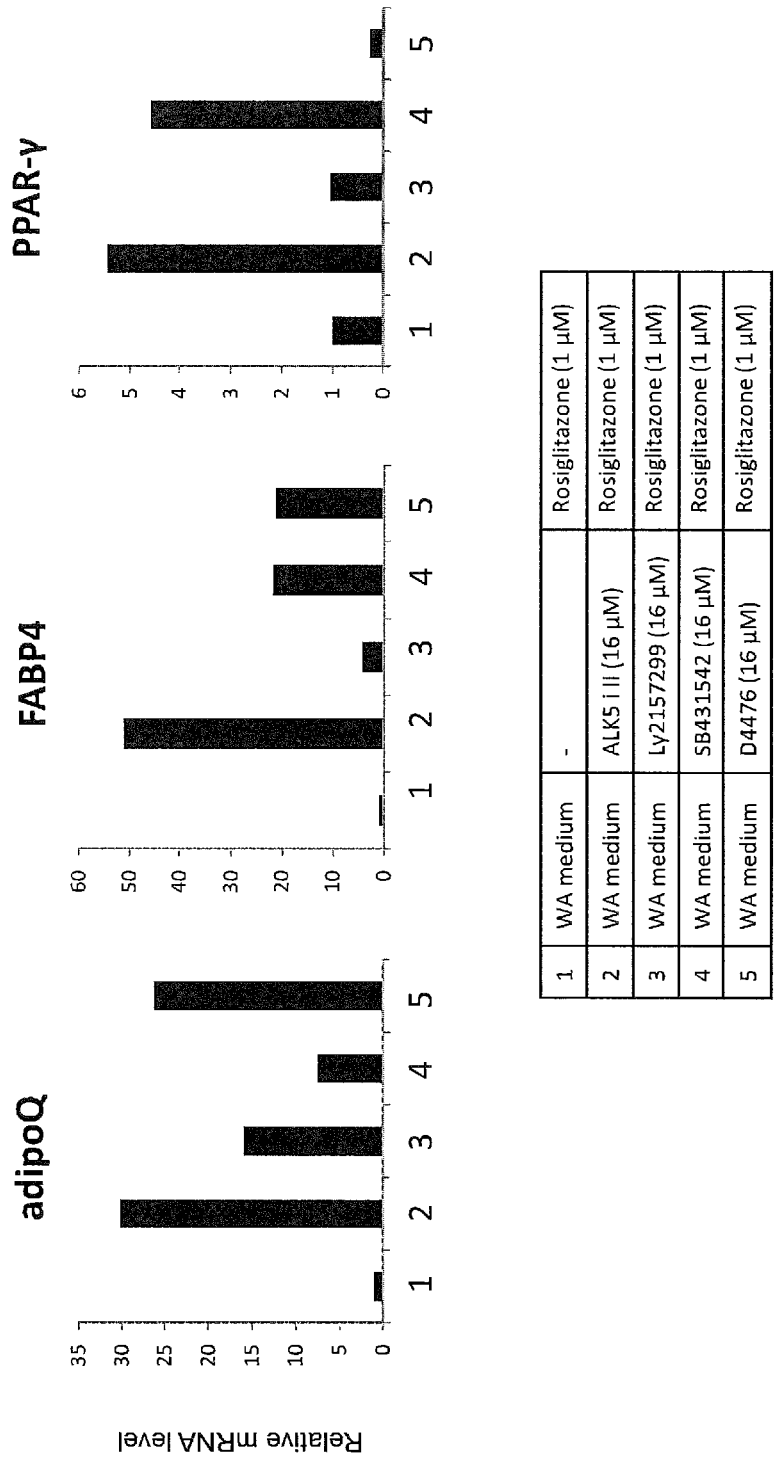
FIG. 54 shows the measurement results of a gene expression level by a real-time RT-PCR method.

Example 50 (FIG. 54)

Human normal skin-derived fibroblasts (human dermal fibroblasts; HDFs) were suspended in Control medium. This was seeded in a 6-well plate at a concentration of $10^4$ cells/mm$^2$ (day 0), and culturing was started in 5% $CO_2$/95% humidified air at 37° C. On day 4, the culture supernatant was removed by suction, the wells were divided into 5 groups and the medium described in the Figure was added. That is,
  group 1: WA medium added with 1 µM Rosiglitazone
  group 2: WA medium added with 1 µM Rosiglitazone and 16 µM ALK5 inhibitor II (ALK5 i II)
  group 3: WA medium added with 1 µM Rosiglitazone and 16 µM LY2157299(LY)
  group 4: WA medium added with 1 µM Rosiglitazone and 16 µM SB431542(SB)
  group 5: WA medium added with 1 µM Rosiglitazone and 16 M D4476(D4).

The composition of the medium is the same as in Example 45. Culturing was continued at 5% $CO_2$/95% humidified air, 37° C. On days 6, 8, 10, the medium was each exchanged with a fresh one having the same composition.

On day 12, RNA was recovered from the cells and, in the same manner as in Example 47, mRNA of AdipoQ, FABP4 (mature adipocyte marker), and PPAR-γ (preadipocyte marker) was quantified.

The results (mean) are shown in FIG. 54. The cells of groups 2-5 expressed mRNA of any one or more genes of AdipoQ, FABP4 and PPAR-γ moderately to highly. The cell added with ALK5 inhibitor II most strongly expressed all of these three genes.

Therefore, it is clear that ALK5 inhibitor II, LY2157299, SB431542 and D4476 converted human fibroblast to white adipocyte. Particularly, it is clear that ALK5 inhibitor II among the TGF-β pathway inhibitors most strongly induced conversion of fibroblast to white adipocyte.

Figure 55:
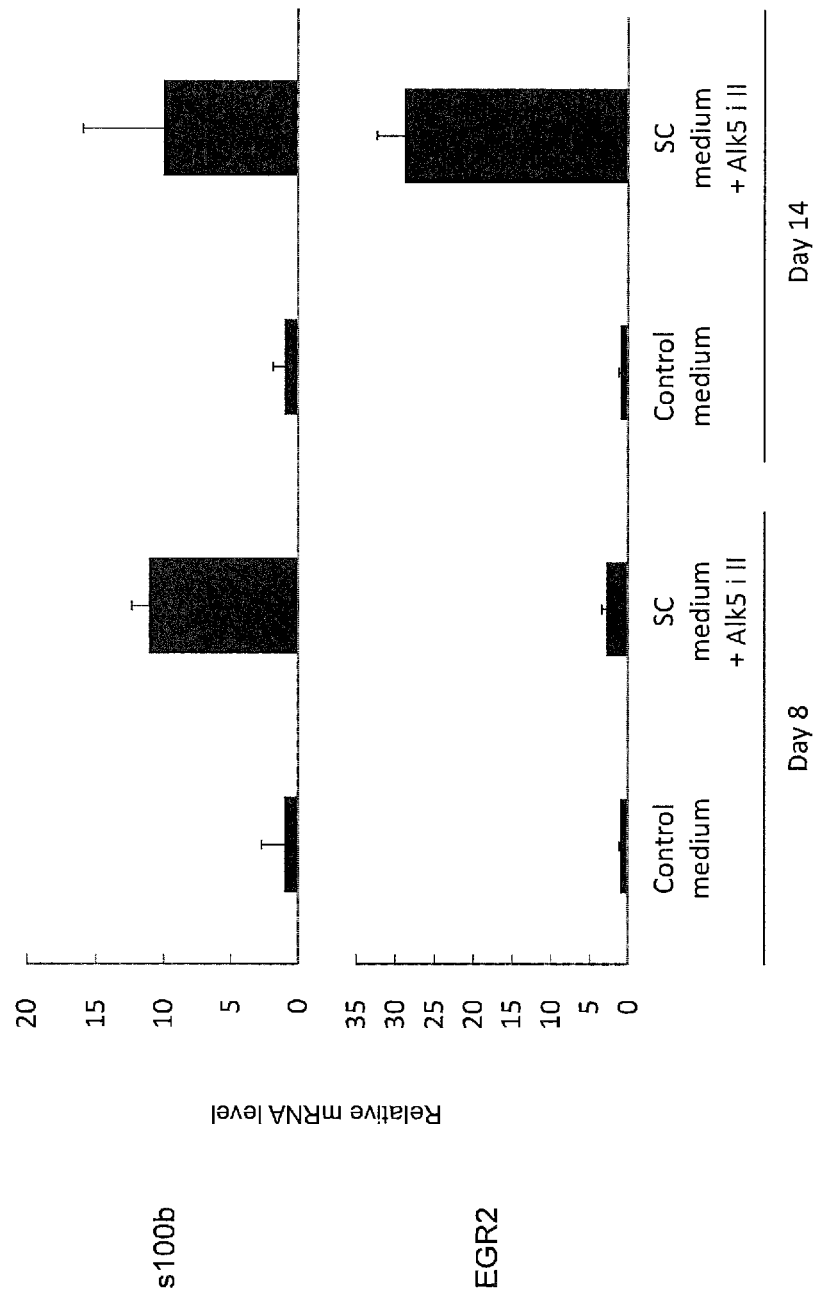
FIG. 55 shows the measurement results of a gene expression level by a real-time RT-PCR method.

Example 51 (FIG. 55)

Human fibroblast aHDF45 were seeded in a 24-well plate at $1.0 \times 10^4$ cells/500 μL/well. The next day, the wells were divided into 2 groups, the medium of one group was exchanged with the following Control medium and the medium of the other group was exchanged with the following SC medium added with 4 μM Alk5 i II. The cells were cultured at 37° C., 5% $CO_2$/95% air for 14 days. The medium was changed two time per week.
Control medium: Dulbecco's modified minimum essential medium; DMEM added with 10% FBS, 100 mM non-essential amino acids (NEAA), 1 mM Sodium Pyruvate, 100 U/ml penicillin, and 100 μg/mL streptomycin
SC (Schwann cell) medium: Dulbecco's modified minimum essential medium; DMEM added with 10% FBS, 10 ng/mL rhbFGF (basic fibroblast growth factor), 5.7 μg/mL Forskolin, 200 ng/mL rhHeregulin beta-1, 5 ng/mL rhPDGF-AA, 100 mM non-essential amino acids (NEAA), 1 mM Sodium Pyruvate, 100 U/ml penicillin, and 100 μg/mL streptomycin.

On days 8 and 14, RNA was extracted from each by using RNeasy Mini QIAcube Kit (QIAGEN), and cDNA was synthesized by a reverse transcription reaction using Rever-Tra Ace qPCR RT Master Mix (TOYOBO). Using the obtained cDNA, real-time RT-PCR analysis of mRNA expression of EGR2 and S100β genes was performed using StepOnePLUS (Applied Biosystems).

The results are shown in FIG. 55. It is clear that culturing in an SC medium added with 4 μM Alk5 i II converted human fibroblast to Schwann cell co-expressing S100β and EGR2.

Figure 56:
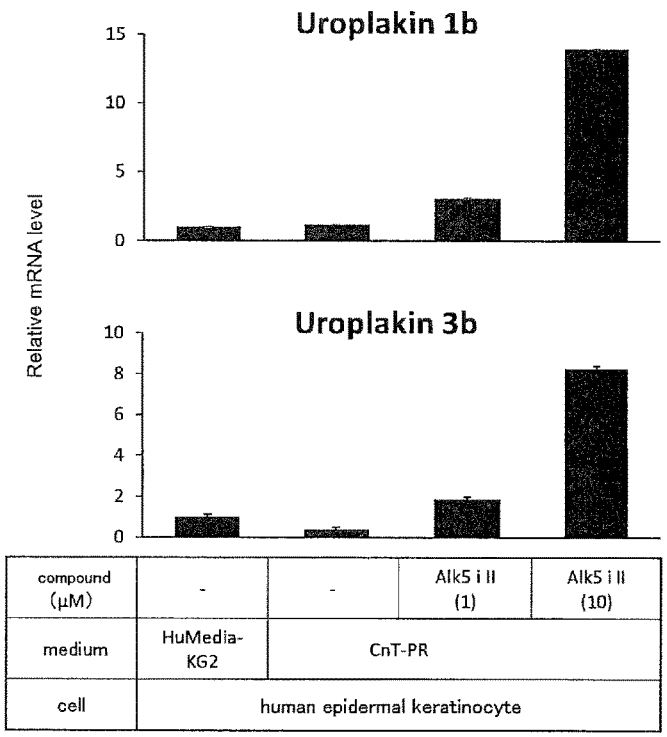
FIG. 56 shows the measurement results of a gene expression level by a real-time RT-PCR method.

Example 52 (FIG. 56)

Normal human epidermal keratinocyte (Human Epidermal Keratinocyte; NHEK (AD)) were suspended in a serum-free liquid medium for normal human epidermal keratinocyte proliferation (HuMedia-KG2; manufactured by Kurabo). This was seeded in a 12-well plate at a concentration of $3 \times 10^4$ cells/well (day 0), and culturing was started in 5% $CO_2$/95% humidified air at 37° C. The next day, the culture supernatant was removed by suction, and HuMedia-KG2 medium, a medium for human epidermal basal cell proliferation (CnT-PR; manufactured by CELLnTEC), or a medium for human epidermal basal cell growth added with ALK5 inhibitor II at a concentration 1 μM or 10 μM was added at 1 mL/well each. Once every 2 days, the culture medium was exchanged with a fresh one, and culturing was performed until day 21. On day 21, the culture medium was removed by suction from each well, washed with PBS(−) and total RNA was extracted from the cells by using RNA easy Mini Kit manufactured by Qiagen. cDNA was synthesized from the RNA by using Rever Tra Ace qPCR RT Master Mix. This cDNA was admixed with Real-time PCR Master Mix, primers specific to Uroplakin 1b gene, Uroplakin 3b gene or β actin gene and Taqman probe. qRT-PCR was performed using AB7300 Real-time PCR system. The mRNA level of Uroplakin 1b gene and Uroplakin 3b gene was quantified as a ratio to β-actin gene mRNA level, and calculated with the value of human epidermal keratinocyte cultured in the HuMedia-KG2 medium as 1. The results thereof are shown in FIG. 56. It is clear that culturing in a CnT-PR medium added with ALK5 inhibitor II converted human epidermal keratinocyte to urothelial cell expressing Uroplakin 1b gene and Uroplakin 3b gene.

Example 53

Human normal peripheral blood mononuclear cells (human peripheral blood mononuclear cells; PBMCs) were suspended in Control medium (RPMI1640 medium added with 10% FBS). This was seeded in a 12-well plate at a concentration of $2.5 \times 10^5$ cells/well (Day 0), and culturing was started in 5% $CO_2$/95% humidified air at 37° C. The next day, the culture supernatant was removed by suction, and Control medium was added to group 1 at 1 mL/well. P-adipocyte induction medium (adipocyte induction medium for peripheral blood mononuclear cell) was added to group 2 at 1 mL/well. P-adipocyte induction medium added with ALK5 inhibitor II at a concentration of 4 μM was added to group 3 at 1 mL/well. The P-adipocyte induction medium is RPMI1640 medium added with 10% FBS, 30 U/ml recombinant hIL-2, 1 nM T3, 1 μM Rosiglitazone, 0.5 mM 3-isobutyl-1-methylxanthine (IBMX), 0.5 μM dexamethasone and 1 μg/mL Insulin. Once every 2 days, 50% of the culture medium was exchanged with a fresh one.

On day 14, the culture medium was removed by suction from each well, washed with PBS(−) and total RNA was extracted from the cells by using RNA easy Mini Kit manufactured by Qiagen. cDNA was synthesized from the RNA by using Rever Tra Ace qPCR RT Master Mix. This cDNA was admixed with Real-time PCR Master Mix, primers specific to FABP4 gene or β actin gene and Taqman probe. qRT-PCR was performed using AB7300 Real-time PCR system. The mRNA level of FABP4 gene was quantified as a ratio to 3-actin gene mRNA level, and calculated with the value of human normal peripheral blood mononuclear cell cultured in the general medium as 1.

Figure 57:
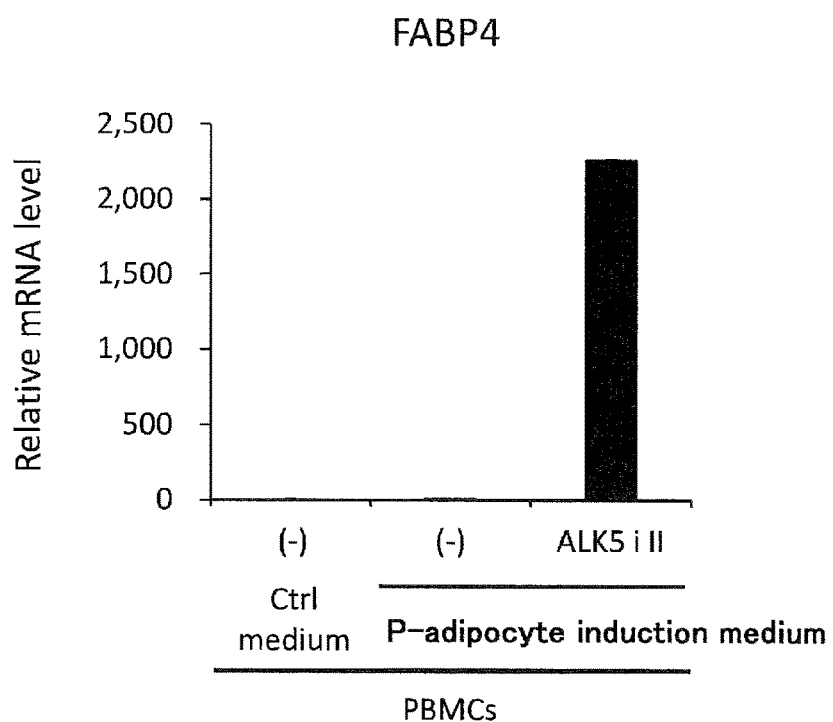
FIG. 57 shows the measurement results of a gene expression level by a real-time RT-PCR method.

The results are shown in FIG. 57. It is clear that culturing in a P-adipocyte induction medium added with ALK5 inhibitor II converts human normal peripheral blood mononuclear cell to white adipocyte expressing FABP4 gene.

The invention claimed is:
1. A method of generating a somatic cell comprising directly converting a fibroblast or keratinocyte of a mammal to an osteoblast by culturing the fibroblast or keratinocyte in a medium containing a TGF-β pathway inhibitor without introducing a gene and without converting into a pluripotent stem cell, wherein the TGF-β pathway inhibitor is an ALK5 inhibitor II.

* * * * *